United States Patent
Pardoux et al.

(10) Patent No.: US 9,845,343 B2
(45) Date of Patent: Dec. 19, 2017

(54) URANIUM-CHELATING PEPTIDES DERIVED FROM EF-HAND CALCIUM-BINDING MOTIF USEFUL FOR URANIUM BIODETECTION AND BIODECONTAMINATION

(71) Applicant: COMMISSARIAT A L'ENERGIE ATOMIQUE ET AUX ENERGIES ALTERNATIVES, Paris (FR)

(72) Inventors: Romain Pardoux, Luynes (FR); Sandrine Sauge-Merle, Pertuis (FR); David Lemaire, Manosque (FR); Catherine Berthomieu, Aix-en-Provence (FR); Philippe Guilbaud, Villeneuve-lès-Avignon (FR); Pascale Delangle, Voiron (FR); Nicolas Bremond, Aix-en-Provence (FR); Maria-Rosa Beccia, Aix-en-Provence (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 14/779,114

(22) PCT Filed: Mar. 28, 2014

(86) PCT No.: PCT/IB2014/060271
§ 371 (c)(1),
(2) Date: Sep. 22, 2015

(87) PCT Pub. No.: WO2014/155356
PCT Pub. Date: Oct. 2, 2014

(65) Prior Publication Data
US 2016/0130316 A1 May 12, 2016

(30) Foreign Application Priority Data

Mar. 28, 2013 (EP) .................................. 13305400
Apr. 23, 2013 (EP) .................................. 13305532

(51) Int. Cl.
| | | |
|---|---|---|
| *C07K 4/00* | (2006.01) | |
| *C07K 5/00* | (2006.01) | |
| *C07K 7/00* | (2006.01) | |
| *C07K 14/00* | (2006.01) | |
| *C07K 14/47* | (2006.01) | |
| *G01N 33/20* | (2006.01) | |
| *G21F 9/30* | (2006.01) | |

(52) U.S. Cl.
CPC ......... *C07K 14/4728* (2013.01); *G01N 33/20* (2013.01); *G21F 9/307* (2013.01); *C07K 2319/60* (2013.01)

(58) Field of Classification Search
CPC ............ H04B 17/318; H04W 36/0022; H04W 36/14; H04W 36/20; H04W 36/30; H04W 36/34; H04W 36/36; H04W 36/38; H04W 48/06; H04W 48/08; H04W 48/18; H04W 76/02; H04W 84/042; H04W 84/12; C07K 14/4728; C07K 2319/60; G01N 33/20; G21F 9/307
See application file for complete search history.

(56) References Cited

U.S. PATENT DOCUMENTS

| | | | |
|---|---|---|---|
| 7,888,311 B2 * | 2/2011 | Vita .................... | C07K 14/4728 514/1.1 |
| 9,321,849 B2 * | 4/2016 | Vita .................... | C07K 14/4728 |
| 2010/0015056 A1 * | 1/2010 | Vita et al. | |
| 2011/0093964 A1 | 4/2011 | Vita et al. | |

OTHER PUBLICATIONS

Tame et al. The crystal structures of the oligopeptide-binding protein OppA complexed with tripeptide and tetrapeptide ligands. Structure, 1995. vol. 3, pp. 1395-1406.*
Gavanji. Application of Recombinant DNA Technology—A review. Applied Science Reports, 2013. vol. 2, No. 2, pp. 29-31.*
Lebrun et al. Engineering Short Peptide Sequences for Uranyl Binding. Chemistry: A European Journal, 2014. vol. 20, p. 16566-16573.*
Glover et al. Structure Determination of OppA at 2.3A Resolution Using Multiple-Wavelength Anomalous Dispersion Methods. Acta Cryst. 1995, D51, p. 39-47.*
Le Clainche et al. Selective binding of uranyl cation by a novel calmodulin peptide. Environ Chem Lett, 2006. vol. 4, pp. 45-49.*
Pardoux et al., Modulating Uranium Binding Affinity in Engineered Xalmodulin EF-Hand Peptides: Effect of Phosphorylation, PLoS ONE, 7: 1-10 (2012).
Miyawaki et al., Fluorescent indicators for Ca2+ based on green fluorescent proteins and calmodulin, Nature: International Weekly Journal of Science, 388: 882-887 (1997).
Hillson et al., Caulobacter crescentus as a Whole-Cell Uranium Biosensor, Applied and Environmental Microbiology, 73: 7615-7621 (2007).
International Search Report dated Jul. 14, 2014, for International application No. PCT/IB2014/060271.

* cited by examiner

*Primary Examiner* — Marcela M Cordero Garcia
(74) *Attorney, Agent, or Firm* — Morgan, Lewis & Bockius LLP

(57) ABSTRACT

Uranium-chelating polypeptides comprising at least one helix-loop-helix calcium-binding (EF-hand) motif which comprises a deletion of at least two amino acid in the 12-amino-acid calcium-binding loop sequence, and their use for uranium biodetection and biodecontamination.

17 Claims, 10 Drawing Sheets

SEQUENCE LISTING

<160> NUMBER OF SEQ ID NOS: 93

<210> SEQ ID NO 1
<211> LENGTH: 452
<212> TYPE: DNA
<213> ORGANISM: Arabidopsis thaliana

<400> SEQUENCE: 1

```
atggcggatc agctcaccga cgatcagatc tctgagttta aggaagcttt cagcttattc    60
gacaaggatg gtgatggttg cattaccacc aaggagctgg gtactgtgat gcgttccctt   120
ggacaaaacc caaccgaagc agagcttcaa gacatgatca acgaagtgga tgctgatggt   180
aacggtacca ttgatttccc agagttcttg aaccttatgg ctcgtaagat gaaggacacc   240
gactctgagg aagagctcaa ggaagcattc cgggttttcg acaaggacca gaacggtttc   300
atctcagcag ctgagctccg ccatgtgatg acaaaccttg gcgagaagct tactgatgaa   360
gaagttgatg agatgatcaa ggaagctgat gttgatggtg atggtcagat taactacgaa   420
gagtttgtta aggtcatgat ggctaagtga ct                                 452
```

<210> SEQ ID NO 2
<211> LENGTH: 149
<212> TYPE: PRT
<213> ORGANISM: Arabidopsis thaliana

<400> SEQUENCE: 2

```
Met Ala Asp Gln Leu Thr Asp Asp Gln Ile Ser Glu Phe Lys Glu Ala
  1               5                  10                  15

Phe Ser Leu Phe Asp Lys Asp Gly Asp Gly Cys Ile Thr Thr Lys Glu
                 20                  25                  30

Leu Gly Thr Val Met Arg Ser Leu Gly Gln Asn Pro Thr Glu Ala Glu
             35                  40                  45

Leu Gln Asp Met Ile Asn Glu Val Asp Ala Asp Gly Asn Gly Thr Ile
         50                  55                  60

Asp Phe Pro Glu Phe Leu Asn Leu Met Ala Arg Lys Met Lys Asp Thr
 65                  70                  75                  80

Asp Ser Glu Glu Glu Leu Lys Glu Ala Phe Arg Val Phe Asp Lys Asp
                 85                  90                  95

Gln Asn Gly Phe Ile Ser Ala Ala Glu Leu Arg His Val Met Thr Asn
                100                 105                 110

Leu Gly Glu Lys Leu Thr Asp Glu Glu Val Asp Glu Met Ile Lys Glu
            115                 120                 125
```

Ala Asp Val Asp Gly Asp Gly Gln Ile Asn Tyr Glu Glu Phe Val Lys
    130                 135                 140

Val Met Met Ala Lys
145

<210> SEQ ID NO 3
<211> LENGTH: 12
<212> TYPE: PRT
<213> ORGANISM: artificial sequence
<220> FEATURE:
<223> OTHER INFORMATION: synthetic peptide CaM3 EF-hand1 loop

<400> SEQUENCE: 3

Asp Lys Asp Gly Asp Gly Cys Ile Thr Thr Lys Glu
1               5                   10

<210> SEQ ID NO 4
<211> LENGTH: 12
<212> TYPE: PRT
<213> ORGANISM: artificial sequence
<220> FEATURE:
<223> OTHER INFORMATION: synthetic peptide CaM3 EF-hand2 loop

<400> SEQUENCE: 4

Asp Ala Asp Gly Asn Gly Thr Ile Asp Phe Pro Glu
1               5                   10

<210> SEQ ID NO 5
<211> LENGTH: 12
<212> TYPE: PRT
<213> ORGANISM: artificial sequence
<220> FEATURE:
<223> OTHER INFORMATION: synthetic peptide CaM3 EF-hand3 loop

<400> SEQUENCE: 5

Asp Lys Asp Gln Asn Gly Phe Ile Ser Ala Ala Glu
1               5                   10

<210> SEQ ID NO 6
<211> LENGTH: 12
<212> TYPE: PRT
<213> ORGANISM: artificial sequence
<220> FEATURE:
<223> OTHER INFORMATION: synthetic peptide CaM3 EF-hand4 loop

<400> SEQUENCE: 6

Asp Val Asp Gly Asp Gly Gln Ile Asn Tyr Glu Glu
1               5                   10

<210> SEQ ID NO 7
<211> LENGTH: 10
<212> TYPE: PRT
<213> ORGANISM: artificial sequence
<220> FEATURE:
<223> OTHER INFORMATION: synthetic peptide EF-hand1 loop delta-K2D3

<400> SEQUENCE: 7

Asp Gly Asp Gly Cys Ile Thr Thr Lys Glu
1               5                   10

<210> SEQ ID NO 8
<211> LENGTH: 10
<212> TYPE: PRT
<213> ORGANISM: artificial sequence
<220> FEATURE:
<223> OTHER INFORMATION: artificial sequence EF-hand1 loop delta-K2D3/C7Y

<400> SEQUENCE: 8

Asp Gly Asp Gly Tyr Ile Thr Thr Lys Glu
1               5                   10

<210> SEQ ID NO 9
<211> LENGTH: 10
<212> TYPE: PRT
<213> ORGANISM: artificial sequence
<220> FEATURE:
<223> OTHER INFORMATION: synthetic peptide EF-hand1 loop
      delta-K2D3/C7Y/T10A/K11A

<400> SEQUENCE: 9

Asp Gly Asp Gly Tyr Ile Thr Ala Ala Glu
1               5                   10

<210> SEQ ID NO 10
<211> LENGTH: 10
<212> TYPE: PRT
<213> ORGANISM: artificial sequence
<220> FEATURE:
<223> OTHER INFORMATION: synthetic peptide EF-hand2 loop delta-A2D3

<400> SEQUENCE: 10

Asp Gly Asn Gly Thr Ile Asp Phe Pro Glu
1               5                   10

<210> SEQ ID NO 11
<211> LENGTH: 10
<212> TYPE: PRT
<213> ORGANISM: artificial sequence
<220> FEATURE:
<223> OTHER INFORMATION: synthetic peptide EF-hand2 loop delta-A2D3/T7Y

<400> SEQUENCE: 11

Asp Gly Asn Gly Tyr Ile Asp Phe Pro Glu
1               5                   10

<210> SEQ ID NO 12
<211> LENGTH: 10
<212> TYPE: PRT
<213> ORGANISM: artificial sequence
<220> FEATURE:
<223> OTHER INFORMATION: synthetic peptide EF-hand2 loop delta-A2D3/N5D

<400> SEQUENCE: 12

Asp Gly Asp Gly Thr Ile Asp Phe Pro Glu
1               5                   10

<210> SEQ ID NO 13
<211> LENGTH: 10
<212> TYPE: PRT
<213> ORGANISM: artificial sequence
<220> FEATURE:
<223> OTHER INFORMATION: synthetic peptide EF-hand2 loop
      delta-A2D3/T7Y/N5D

<400> SEQUENCE: 13

Asp Gly Asp Gly Tyr Ile Asp Phe Pro Glu
1               5                   10

<210> SEQ ID NO 14
<211> LENGTH: 10
<212> TYPE: PRT
<213> ORGANISM: artificial sequence
<220> FEATURE:
<223> OTHER INFORMATION: synthetic peptide EF-hand3 loop delta-K2D3

<400> SEQUENCE: 14

Asp Gln Asn Gly Phe Ile Ser Ala Ala Glu
1               5                   10

<210> SEQ ID NO 15
<211> LENGTH: 10
<212> TYPE: PRT
<213> ORGANISM: artificial sequence
<220> FEATURE:
<223> OTHER INFORMATION: synthetic peptide EF-hand4 loop delta-V2D3

<400> SEQUENCE: 15

Asp Gly Asp Gly Gln Ile Asn Tyr Glu Glu
1               5                   10

<210> SEQ ID NO 16
<211> LENGTH: 228
<212> TYPE: DNA
<213> ORGANISM: artificial sequence
<220> FEATURE:
<223> OTHER INFORMATION: synthetic polynucleotide encoding CaM-delta

<400> SEQUENCE: 16
tccatggcgg atcagctcac cgacgatcag atctctgagt ttaaggaagc tttcagctta      60
ttcgacggtg atggttacat taccgccgcg gagctgggta ctgtgatgcg ttcccttgga     120
caaaacccaa ccgaagcaga gcttcaagac atgatcaacg aagtggctgc tgctggtaac     180
ggtaccattg atttcccaga gttcttgaac cttatggctc gtaagtga                 228

<210> SEQ ID NO 17
<211> LENGTH: 75
<212> TYPE: PRT
<213> ORGANISM: artificial sequence
<220> FEATURE:
<223> OTHER INFORMATION: synthetic peptide CaM-delta

<400> SEQUENCE: 17

Ser Met Ala Asp Gln Leu Thr Asp Asp Gln Ile Ser Glu Phe Lys Glu
1               5                   10                  15

Ala Phe Ser Leu Phe Asp Gly Asp Gly Tyr Ile Thr Ala Ala Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Ala Ala Ala Gly Asn Gly Thr Ile Asp
    50                  55                  60

Phe Pro Glu Phe Leu Asn Leu Met Ala Arg Lys
65                  70                  75

<210> SEQ ID NO 18
<211> LENGTH: 147
<212> TYPE: PRT
<213> ORGANISM: artificial sequence
<220> FEATURE:
<223> OTHER INFORMATION: synthetic Calmodulin variant protein from
      Cameleon biosensor-delta protein

<400> SEQUENCE: 18

Met Ala Asp Gln Leu Thr Asp Asp Gln Ile Ser Glu Phe Lys Glu Ala
1               5                   10                  15

Phe Ser Leu Phe Asp Gly Asp Gly Cys Ile Thr Thr Lys Glu Leu Gly

```
            20                  25                  30
Thr Val Met Arg Ser Leu Gly Gln Asn Pro Thr Glu Ala Glu Leu Gln
             35                  40                  45
Asp Met Ile Asn Glu Val Asp Ala Asp Gly Asn Gly Thr Ile Asp Phe
         50                  55                  60
Pro Glu Phe Leu Asn Leu Met Ala Arg Lys Met Lys Asp Thr Asp Ser
 65                  70                  75                  80
Glu Glu Glu Leu Lys Glu Ala Phe Arg Val Phe Asp Lys Asp Gln Asn
                 85                  90                  95
Gly Phe Ile Ser Ala Ala Glu Leu Arg His Val Met Thr Asn Leu Gly
            100                 105                 110
Glu Lys Leu Thr Asp Glu Glu Val Asp Glu Met Ile Lys Glu Ala Asp
        115                 120                 125
Val Asp Gly Asp Gly Gln Ile Asn Tyr Glu Glu Phe Val Lys Val Met
    130                 135                 140
Met Ala Lys
145

<210> SEQ ID NO 19
<211> LENGTH: 147
<212> TYPE: PRT
<213> ORGANISM: artificial sequence
<220> FEATURE:
<223> OTHER INFORMATION: synthetic Calmodulin variant protein from
      Cameleon biosensor-delta-S2M protein

<400> SEQUENCE: 19

Met Ala Asp Gln Leu Thr Asp Asp Gln Ile Ser Glu Phe Lys Glu Ala
 1               5                  10                  15
Phe Ser Leu Phe Asp Gly Asp Gly Cys Ile Thr Thr Lys Glu Leu Gly
             20                  25                  30
Thr Val Met Arg Ser Leu Gly Gln Asn Pro Thr Glu Ala Glu Leu Gln
         35                  40                  45
Asp Met Ile Asn Glu Val Ala Ala Ala Gly Asn Gly Thr Ile Asp Phe
     50                  55                  60
Pro Glu Phe Leu Asn Leu Met Ala Arg Lys Met Lys Asp Thr Asp Ser
 65                  70                  75                  80
Glu Glu Glu Leu Lys Glu Ala Phe Arg Val Phe Asp Lys Asp Gln Asn
                 85                  90                  95
Gly Phe Ile Ser Ala Ala Glu Leu Arg His Val Met Thr Asn Leu Gly
            100                 105                 110
Glu Lys Leu Thr Asp Glu Glu Val Asp Glu Met Ile Lys Glu Ala Asp
        115                 120                 125
Val Asp Gly Asp Gly Gln Ile Asn Tyr Glu Glu Phe Val Lys Val Met
    130                 135                 140
Met Ala Lys
145

<210> SEQ ID NO 20
<211> LENGTH: 141
<212> TYPE: PRT
<213> ORGANISM: artificial sequence
<220> FEATURE:
<223> OTHER INFORMATION: synthetic calmodulin variant protein delta
      sites 1,2,3,4

<400> SEQUENCE: 20

Met Ala Asp Gln Leu Thr Asp Asp Gln Ile Ser Glu Phe Lys Glu Ala
```

```
1               5                   10                  15
Phe Ser Leu Phe Asp Gly Asp Gly Cys Ile Thr Thr Lys Glu Leu Gly
                20                  25                  30
Thr Val Met Arg Ser Leu Gly Gln Asn Pro Thr Glu Ala Glu Leu Gln
            35                  40                  45
Asp Met Ile Asn Glu Val Asp Gly Asn Gly Thr Ile Asp Phe Pro Glu
        50                  55                  60
Phe Leu Asn Leu Met Ala Arg Lys Met Lys Asp Thr Asp Ser Glu Glu
65                  70                  75                  80
Glu Leu Lys Glu Ala Phe Arg Val Phe Asp Gln Asn Gly Phe Ile Ser
                85                  90                  95
Ala Ala Glu Leu Arg His Val Met Thr Asn Leu Gly Glu Lys Leu Thr
            100                 105                 110
Asp Glu Glu Val Asp Glu Met Ile Lys Glu Ala Asp Gly Asp Gly Gln
        115                 120                 125
Ile Asn Tyr Glu Glu Phe Val Lys Val Met Met Ala Lys
    130                 135                 140

<210> SEQ ID NO 21
<211> LENGTH: 78
<212> TYPE: DNA
<213> ORGANISM: artificial sequence
<220> FEATURE:
<223> OTHER INFORMATION: synthetic polynucleotide encoding M13 peptide

<400> SEQUENCE: 21
aaacgtcgct ggaaaaaaaa ctttattgcg gtgagcgcgg ccaaccgctt taaaaaaatt     60
agctcgagcg gcgcgctg                                                  78

<210> SEQ ID NO 22
<211> LENGTH: 26
<212> TYPE: PRT
<213> ORGANISM: artificial sequence
<220> FEATURE:
<223> OTHER INFORMATION: synthetic peptide M13

<400> SEQUENCE: 22

Lys Arg Arg Trp Lys Lys Asn Phe Ile Ala Val Ser Ala Ala Asn Arg
1               5                   10                  15
Phe Lys Lys Ile Ser Ser Ser Gly Ala Leu
            20                  25

<210> SEQ ID NO 23
<211> LENGTH: 25
<212> TYPE: PRT
<213> ORGANISM: artificial sequence
<220> FEATURE:
<223> OTHER INFORMATION: synthetic peptide skMLCK

<400> SEQUENCE: 23

Lys Arg Arg Trp Lys Lys Asn Phe Ile Ala Val Ser Ala Ala Asn Arg
1               5                   10                  15
Phe Lys Lys Ile Ser Ser Ser Gly Ala
            20                  25

<210> SEQ ID NO 24
<211> LENGTH: 17
<212> TYPE: PRT
<213> ORGANISM: artificial sequence
<220> FEATURE:
<223> OTHER INFORMATION: synthetic peptide MLCKp
```

```
<400> SEQUENCE: 24

Arg Arg Lys Trp Gln Lys Thr Gly His Ala Val Arg Ala Ile Gly Arg
1               5                   10                  15

Leu

<210> SEQ ID NO 25
<211> LENGTH: 20
<212> TYPE: PRT
<213> ORGANISM: artificial sequence
<220> FEATURE:
<223> OTHER INFORMATION: synthetic peptide smMLCK

<400> SEQUENCE: 25

Ala Arg Arg Lys Trp Gln Lys Thr Gly His Ala Val Arg Ala Ile Gly
1               5                   10                  15

Arg Leu Ser Ser
            20

<210> SEQ ID NO 26
<211> LENGTH: 13
<212> TYPE: PRT
<213> ORGANISM: artificial sequence
<220> FEATURE:
<223> OTHER INFORMATION: synthetic peptide from wasp venom

<400> SEQUENCE: 26

Val Asn Trp Lys Lys Ile Gly Gln His Ile Leu Ser Val
1               5                   10

<210> SEQ ID NO 27
<211> LENGTH: 24
<212> TYPE: PRT
<213> ORGANISM: artificial sequence
<220> FEATURE:
<223> OTHER INFORMATION: synthetic peptide p21

<400> SEQUENCE: 27

Lys Arg Arg Gln Thr Ser Met Thr Asp Phe Tyr His Ser Lys Arg Arg
1               5                   10                  15

Leu Ile Phe Ser Lys Arg Lys Pro
            20

<210> SEQ ID NO 28
<211> LENGTH: 26
<212> TYPE: PRT
<213> ORGANISM: artificial sequence
<220> FEATURE:
<223> OTHER INFORMATION: synthetic peptide from melittin

<400> SEQUENCE: 28

Gln Gln Arg Lys Arg Lys Ile Trp Ser Ile Leu Ala Pro Leu Gly Thr
1               5                   10                  15

Thr Leu Val Lys Leu Val Ala Gly Ile Gly
            20                  25

<210> SEQ ID NO 29
<211> LENGTH: 24
<212> TYPE: PRT
<213> ORGANISM: artificial sequence
<220> FEATURE:
<223> OTHER INFORMATION: synthetic peptide from spectrin

<400> SEQUENCE: 29
```

```
Lys Thr Ala Ser Pro Trp Lys Ser Ala Arg Leu Met Val His Thr Val
1               5                   10                  15

Ala Thr Phe Asn Ser Ile Lys Glu
            20
```

<210> SEQ ID NO 30
<211> LENGTH: 22
<212> TYPE: PRT
<213> ORGANISM: artificial sequence
<220> FEATURE:
<223> OTHER INFORMATION: synthetic peptide CaMKI

<400> SEQUENCE: 30

```
Ala Lys Ser Lys Trp Lys Gln Ala Phe Asn Ala Thr Ala Val Val Arg
1               5                   10                  15

His Met Arg Lys Leu Gln
            20
```

<210> SEQ ID NO 31
<211> LENGTH: 25
<212> TYPE: PRT
<213> ORGANISM: artificial sequence
<220> FEATURE:
<223> OTHER INFORMATION: synthetic peptide CaMKII

<400> SEQUENCE: 31

```
Leu Lys Lys Phe Asn Ala Arg Arg Lys Leu Lys Gly Ala Ile Leu Thr
1               5                   10                  15

Thr Met Leu Ala Thr Arg Asn Phe Ser
            20                  25
```

<210> SEQ ID NO 32
<211> LENGTH: 27
<212> TYPE: PRT
<213> ORGANISM: artificial sequence
<220> FEATURE:
<223> OTHER INFORMATION: synthetic peptide CaMKK

<400> SEQUENCE: 32

```
Arg Phe Pro Asn Gly Phe Arg Lys Arg His Gly Met Ala Lys Val Leu
1               5                   10                  15

Ile Leu Thr Asp Leu Arg Pro Ile Arg Arg Val
            20                  25
```

<210> SEQ ID NO 33
<211> LENGTH: 17
<212> TYPE: PRT
<213> ORGANISM: artificial sequence
<220> FEATURE:
<223> OTHER INFORMATION: synthetic peptide1

<400> SEQUENCE: 33

```
Leu Lys Trp Lys Lys Leu Leu Lys Leu Leu Lys Lys Leu Leu Lys Leu
1               5                   10                  15

Gly
```

<210> SEQ ID NO 34
<211> LENGTH: 1953
<212> TYPE: DNA
<213> ORGANISM: artificial sequence
<220> FEATURE:
<223> OTHER INFORMATION: synthetic polynucleotide encoding
      biosensor-delta

<400> SEQUENCE: 34

```
tccatggtga gcaagggcga ggagctgttc accggggtgg tgcccatcct ggtcgagctg    60
gacggcgacg taaacggcca caggttcagc gtgtccggcg agggcgaggg cgatgccacc   120
tacggcaagc tgaccctgaa gttcatctgc accaccggca agctgcccgt gccctggccc   180
accctcgtga ccaccctgac ctggggcgtg cagtgcttca gccgctaccc cgaccacatg   240
aagcagcacg acttcttcaa gtccgccatg cccgaaggct acgtccagga gcgtaccatc   300
ttcttcaagg acgacggcaa ctacaagacc cgcgccgagg tgaagttcga gggcgacacc   360
ctggtgaacc gcatcgagct gaagggcatc gacttcaagg aggacggcaa catcctgggg   420
cacaagctgg agtacaacta catcagccac aacgtctata tcaccgccga caagcagaag   480
aacggcatca aggcccactt caagatccgc cacaacatcg aggacggcag cgtgcagctc   540
gccgaccact accagcagaa cacccccatc ggcgacggcc ccgtgctgct gcccgacaac   600
cactacctga gcacccagtc cgccctgagc aaagaccccaa acgagaagcg cgatcacatg   660
gtcctgctgg agttcgtgac cgccgccgag ctcatggcgg atcagttgac cgacgatcag   720
atctctgaat taaggaagc cttcagctta ttcgacggtg atggttgcat taccaccaag   780
gaactgggta ctgtgatgcg ttccctgggc caaaacccga ccgaagcaga gctgcaagac   840
atgatcaacg aagtggatgc ggatggtaac ggtaccattg atttcccgga attcttgaac   900
ctgatggccc gtaagatgaa agacaccgac agcgaggaag agctgaaaga gccttccgc   960 gttttcgaca agaccagaa cggtttcatc agcgcagcgg aactgcgcca tgtgatgacc  1020
aacctgggcg aaaaactgac ggatgaagaa gttgatgaga tgatcaaaga gcggatgtg  1080 gatggtgatg gtcagattaa ctacgaagag tttgttaagg tgatgatggc gaaaggcggt  1140
ggcggtagca acgtcgctg gaaaaaaaac tttattgcgg tgagcgcggc caaccgcttt  1200
aaaaaaatta gctcgagcgg cgcgctggtc gacatggtga gcaagggcga ggagctgttc  1260
accggggtgg tgcccatcct ggtcgagctg gacggcgacg taaacggcca caggttcagc  1320
gtgtccggcg agggcgaggg cgatgccacc tacggcaagc tgaccctgaa gttcatctgc  1380
accaccggca agctgcccgt gccctggccc accctcgtga ccaccttcgg ctacggcgtg  1440
cagtgcttcg cccgctaccc cgaccacatg aagcagcacg acttcttcaa gtccgccatg  1500
cccgaaggct acgtccagga gcgcaccatc ttcttcaagg acgacggcaa ctacaagacc  1560
cgcgccgagg tgaagttcga gggcgacacc ctggtgaacc gcatcgagct gaagggcatc  1620
gacttcaagg aggacggcaa catcctgggg cacaagctgg agtacaacta caacagccac  1680
aacgtctata tcatggccga caagcagaag aacggcatca aggtgaactt caagatccgc  1740
cacaacatcg aggacggcag cgtgcagctc gccgaccact accagcagaa cacccccatc  1800
ggcgacggcc ccgtgctgct gcccgacaac cactacctga gctaccagtc cgccctgagc  1860
aaagacccca acgagaagcg cgatcacatg gtcctgctgg agttcgtgac cgccgccggg  1920
atcactctcg gcatggacga gctgtacaag taa                               1953
```

<210> SEQ ID NO 35
<211> LENGTH: 650
<212> TYPE: PRT
<213> ORGANISM: artificial sequence
<220> FEATURE:
<223> OTHER INFORMATION: synthetic protein biosensor-delta

<400> SEQUENCE: 35

Ser Met Val Ser Lys Gly Glu Glu Leu Phe Thr Gly Val Val Pro Ile
1               5                   10                  15

-continued

Leu Val Glu Leu Asp Gly Asp Val Asn Gly His Arg Phe Ser Val Ser
            20                  25                  30

Gly Glu Gly Glu Gly Asp Ala Thr Tyr Gly Lys Leu Thr Leu Lys Phe
        35                  40                  45

Ile Cys Thr Thr Gly Lys Leu Pro Val Pro Trp Pro Thr Leu Val Thr
50                  55                  60

Thr Leu Thr Trp Gly Val Gln Cys Phe Ser Arg Tyr Pro Asp His Met
65                  70                  75                  80

Lys Gln His Asp Phe Phe Lys Ser Ala Met Pro Glu Gly Tyr Val Gln
                85                  90                  95

Glu Arg Thr Ile Phe Phe Lys Asp Gly Asn Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
130                 135                 140

Tyr Asn Tyr Ile Ser His Asn Val Tyr Ile Thr Ala Asp Lys Gln Lys
145                 150                 155                 160

Asn Gly Ile Lys Ala His Phe Lys Ile Arg His Asn Ile Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asn His Tyr Leu Ser Thr Gln Ser Ala
        195                 200                 205

Leu Ser Lys Asp Pro Asn Glu Lys Arg Asp His Met Val Leu Leu Glu
    210                 215                 220

Phe Val Thr Ala Ala Glu Leu Met Ala Asp Gln Leu Thr Asp Asp Gln
225                 230                 235                 240

Ile Ser Glu Phe Lys Glu Ala Phe Ser Leu Phe Asp Gly Asp Gly Cys
                245                 250                 255

Ile Thr Thr Lys Glu Leu Gly Thr Val Met Arg Ser Leu Gly Gln Asn
            260                 265                 270

Pro Thr Glu Ala Glu Leu Gln Asp Met Ile Asn Glu Val Asp Ala Asp
        275                 280                 285

Gly Asn Gly Thr Ile Asp Phe Pro Glu Phe Leu Asn Leu Met Ala Arg
290                 295                 300

Lys Met Lys Asp Thr Asp Ser Glu Glu Glu Leu Lys Glu Ala Phe Arg
305                 310                 315                 320

Val Phe Asp Lys Asp Gln Asn Gly Phe Ile Ser Ala Ala Glu Leu Arg
                325                 330                 335

His Val Met Thr Asn Leu Gly Glu Lys Leu Thr Asp Glu Glu Val Asp
            340                 345                 350

Glu Met Ile Lys Glu Ala Asp Val Asp Gly Asp Gly Gln Ile Asn Tyr
        355                 360                 365

Glu Glu Phe Val Lys Val Met Met Ala Lys Gly Gly Gly Ser Lys
    370                 375                 380

Arg Arg Trp Lys Lys Asn Phe Ile Ala Val Ser Ala Ala Asn Arg Phe
385                 390                 395                 400

Lys Lys Ile Ser Ser Ser Gly Ala Leu Val Asp Met Val Ser Lys Gly
                405                 410                 415

Glu Glu Leu Phe Thr Gly Val Val Pro Ile Leu Val Glu Leu Asp Gly
            420                 425                 430

Asp Val Asn Gly His Lys Phe Ser Val Ser Gly Glu Gly Glu Gly Asp
            435                 440                 445

Ala Thr Tyr Gly Lys Leu Thr Leu Lys Phe Ile Cys Thr Thr Gly Lys
450                 455                 460

Leu Pro Val Pro Trp Pro Thr Leu Val Thr Thr Phe Gly Tyr Gly Val
465                 470                 475                 480

Gln Cys Phe Ala Arg Tyr Pro Asp His Met Lys Gln His Asp Phe Phe
                485                 490                 495

Lys Ser Ala Met Pro Glu Gly Tyr Val Gln Glu Arg Thr Ile Phe Phe
                500                 505                 510

Lys Asp Asp Gly Asn Tyr Lys Thr Arg Ala Glu Val Lys Phe Glu Gly
            515                 520                 525

Asp Thr Leu Val Asn Arg Ile Glu Leu Lys Gly Ile Asp Phe Lys Glu
530                 535                 540

Asp Gly Asn Ile Leu Gly His Lys Leu Glu Tyr Asn Tyr Asn Ser His
545                 550                 555                 560

Asn Val Tyr Ile Met Ala Asp Lys Gln Lys Asn Gly Ile Lys Val Asn
                565                 570                 575

Phe Lys Ile Arg His Asn Ile Glu Asp Gly Ser Val Gln Leu Ala Asp
                580                 585                 590

His Tyr Gln Gln Asn Thr Pro Ile Gly Asp Gly Pro Val Leu Leu Pro
            595                 600                 605

Asp Asn His Tyr Leu Ser Tyr Gln Ser Ala Leu Ser Lys Asp Pro Asn
610                 615                 620

Glu Lys Arg Asp His Met Val Leu Leu Glu Phe Val Thr Ala Ala Gly
625                 630                 635                 640

Ile Thr Leu Gly Met Asp Glu Leu Tyr Lys
                645                 650

<210> SEQ ID NO 36
<211> LENGTH: 1953
<212> TYPE: DNA
<213> ORGANISM: artificial sequence
<220> FEATURE:
<223> OTHER INFORMATION: synthetic polynucleotide encoding cameleon
      biosensor delta-S2M

<400> SEQUENCE: 36
tccatggtga gcaagggcga ggagctgttc accggggtgg tgcccatcct ggtcgagctg      60
gacggcgacg taaacggcca caggttcagc gtgtccggcg agggcgaggg cgatgccacc     120
tacggcaagc tgaccctgaa gttcatctgc accaccggca agctgcccgt gccctggccc     180
accctcgtga ccaccctgac ctggggcgtg cagtgcttca gccgctaccc cgaccacatg     240
aagcagcaca cttcttcaa gtccgccatg cccgaaggct acgtccagga gcgtaccatc     300
ttcttcaagg acgacggcaa ctacaagacc cgcgccgagg tgaagttcga gggcgacacc     360
ctggtgaacc gcatcgagct gaagggcatc gacttcaagg aggacggcaa catcctgggg     420
cacaagctgg agtacaacta catcagccac aacgtctata tcaccgccga caagcagaag     480
aacggcatca aggcccactt caagatccgc cacaacatcg aggacggcag cgtgcagctc     540
gccgaccact accagcagaa cacccccatc ggcgacggcc ccgtgctgct gcccgacaac     600
cactacctga gcacccagtc cgccctgagc aaagacccca acgagaagcg cgatcacatg     660
gtcctgctgg agttcgtgac cgccgccgag ctcatggcgg atcagttgac cgacgatcag     720
atctctgaat taaggaagc cttcagctta ttcgacggtg atggttgcat taccaccaag     780

-continued

```
gaactgggta ctgtgatgcg ttccctgggc caaaacccga ccgaagcaga gctgcaagac    840
atgatcaacg aagtggctgc ggctggtaac ggtaccattg atttcccgga attcttgaac    900
ctgatggccc gtaagatgaa agacaccgac agcgaggaag agctgaaaga agccttccgc    960
gttttcgaca agaccagaa cggtttcatc agcgcagcgg aactgcgcca tgtgatgacc   1020
aacctgggcg aaaaactgac ggatgaagaa gttgatgaga tgatcaaaga agcggatgtg   1080
gatggtgatg gtcagattaa ctacgaagag tttgttaagg tgatgatggc gaaaggcggt   1140
ggcggtagca acgtcgctg gaaaaaaaac tttattgcgg tgagcgcggc caaccgcttt   1200
aaaaaaatta gctcgagcgg cgcgctggtc gacatggtga gcaagggcga ggagctgttc   1260
accggggtgg tgcccatcct ggtcgagctg gacggcgacg taaacggcca agttcagc    1320 gtgtccggcg agggcgaggg cgatgccacc tacggcaagc tgaccctgaa gttcatctgc   1380
accaccggca agctgcccgt gccctggccc accctcgtga ccaccttcgg ctacggcgtg   1440
cagtgcttcg cccgctaccc cgaccacatg aagcagcacg acttcttcaa gtccgccatg   1500
cccgaaggct acgtccagga gcgcaccatc ttcttcaagg acgacggcaa ctacaagacc   1560
cgcgccgagg tgaagttcga gggcgacacc ctggtgaacc gcatcgagct gaagggcatc   1620
gacttcaagg aggacggcaa catcctgggg cacaagctgg agtacaacta caacagccac   1680
aacgtctata tcatggccga caagcagaag aacggcatca aggtgaactt caagatccgc   1740
cacaacatcg aggacggcag cgtgcagctc gccgaccact accagcagaa cacccccatc   1800
ggcgacggcc ccgtgctgct gcccgacaac cactacctga gctaccagtc cgccctgagc   1860
aaagacccca cgagaagcg cgatcacatg gtcctgctgg agttcgtgac cgccgccggg   1920
atcactctcg gcatggacga gctgtacaag taa                                1953
```

```
<210> SEQ ID NO 37
<211> LENGTH: 650
<212> TYPE: PRT
<213> ORGANISM: artificial sequence
<220> FEATURE:
<223> OTHER INFORMATION: synthetic protein Cameleon biosensor delta-S2M

<400> SEQUENCE: 37
```

```
Ser Met Val Ser Lys Gly Glu Glu Leu Phe Thr Gly Val Val Pro Ile
1               5                   10                  15

Leu Val Glu Leu Asp Gly Asp Val Asn Gly His Arg Phe Ser Val Ser
            20                  25                  30

Gly Glu Gly Glu Gly Asp Ala Thr Tyr Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Trp Gly Val Gln Cys Phe Ser Arg Tyr Pro Asp His Met
65                  70                  75                  80

Lys Gln His Asp Phe Phe Lys Ser Ala Met Pro Glu Gly Tyr Val Gln
                85                  90                  95

Glu Arg Thr Ile Phe Phe Lys Asp Asp Gly Asn Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Tyr Ile Ser His Asn Val Tyr Ile Thr Ala Asp Lys Gln Lys
145                 150                 155                 160
```

```
Asn Gly Ile Lys Ala His Phe Lys Ile Arg His Asn Ile Glu Asp Gly
            165                 170                 175

Ser Val Gln Leu Ala Asp His Tyr Gln Gln Asn Thr Pro Ile Gly Asp
        180                 185                 190

Gly Pro Val Leu Leu Pro Asp Asn His Tyr Leu Ser Thr Gln Ser Ala
            195                 200                 205

Leu Ser Lys Asp Pro Asn Glu Lys Arg Asp His Met Val Leu Leu Glu
        210                 215                 220

Phe Val Thr Ala Ala Glu Leu Met Ala Asp Gln Leu Thr Asp Asp Gln
225                 230                 235                 240

Ile Ser Glu Phe Lys Glu Ala Phe Ser Leu Phe Asp Gly Asp Gly Cys
            245                 250                 255

Ile Thr Thr Lys Glu Leu Gly Thr Val Met Arg Ser Leu Gly Gln Asn
            260                 265                 270

Pro Thr Glu Ala Glu Leu Gln Asp Met Ile Asn Glu Val Ala Ala Ala
        275                 280                 285

Gly Asn Gly Thr Ile Asp Phe Pro Glu Phe Leu Asn Leu Met Ala Arg
        290                 295                 300

Lys Met Lys Asp Thr Asp Ser Glu Glu Glu Leu Lys Glu Ala Phe Arg
305                 310                 315                 320

Val Phe Asp Lys Asp Gln Asn Gly Phe Ile Ser Ala Ala Glu Leu Arg
            325                 330                 335

His Val Met Thr Asn Leu Gly Glu Lys Leu Thr Asp Glu Glu Val Asp
            340                 345                 350

Glu Met Ile Lys Glu Ala Asp Val Asp Gly Asp Gly Gln Ile Asn Tyr
        355                 360                 365

Glu Glu Phe Val Lys Val Met Met Ala Lys Gly Gly Gly Gly Ser Lys
        370                 375                 380

Arg Arg Trp Lys Lys Asn Phe Ile Ala Val Ser Ala Ala Asn Arg Phe
385                 390                 395                 400

Lys Lys Ile Ser Ser Ser Gly Ala Leu Val Asp Met Val Ser Lys Gly
            405                 410                 415

Glu Glu Leu Phe Thr Gly Val Val Pro Ile Leu Val Glu Leu Asp Gly
            420                 425                 430

Asp Val Asn Gly His Lys Phe Ser Val Ser Gly Glu Gly Glu Gly Asp
        435                 440                 445

Ala Thr Tyr Gly Lys Leu Thr Leu Lys Phe Ile Cys Thr Thr Gly Lys
        450                 455                 460

Leu Pro Val Pro Trp Pro Thr Leu Val Thr Thr Phe Gly Tyr Gly Val
465                 470                 475                 480

Gln Cys Phe Ala Arg Tyr Pro Asp His Met Lys Gln His Asp Phe Phe
            485                 490                 495

Lys Ser Ala Met Pro Glu Gly Tyr Val Gln Glu Arg Thr Ile Phe Phe
            500                 505                 510

Lys Asp Asp Gly Asn Tyr Lys Thr Arg Ala Glu Val Lys Phe Glu Gly
        515                 520                 525

Asp Thr Leu Val Asn Arg Ile Glu Leu Lys Gly Ile Asp Phe Lys Glu
530                 535                 540

Asp Gly Asn Ile Leu Gly His Lys Leu Glu Tyr Asn Tyr Asn Ser His
545                 550                 555                 560

Asn Val Tyr Ile Met Ala Asp Lys Gln Lys Asn Gly Ile Lys Val Asn
            565                 570                 575
```

```
Phe Lys Ile Arg His Asn Ile Glu Asp Gly Ser Val Gln Leu Ala Asp
                580                 585                 590
His Tyr Gln Gln Asn Thr Pro Ile Gly Asp Gly Pro Val Leu Leu Pro
            595                 600                 605
Asp Asn His Tyr Leu Ser Tyr Gln Ser Ala Leu Ser Lys Asp Pro Asn
        610                 615                 620
Glu Lys Arg Asp His Met Val Leu Leu Glu Phe Val Thr Ala Ala Gly
625                 630                 635                 640
Ile Thr Leu Gly Met Asp Glu Leu Tyr Lys
                645                 650

<210> SEQ ID NO 38
<211> LENGTH: 644
<212> TYPE: PRT
<213> ORGANISM: artificial sequence
<220> FEATURE:
<223> OTHER INFORMATION: synthetic protein Cameleon biosensor
      delta-delta-delta-delta

<400> SEQUENCE: 38

Ser Met Val Ser Lys Gly Glu Glu Leu Phe Thr Gly Val Val Pro Ile
1               5                   10                  15
Leu Val Glu Leu Asp Gly Asp Val Asn Gly His Arg Phe Ser Val Ser
                20                  25                  30
Gly Glu Gly Glu Gly Asp Ala Thr Tyr Gly Lys Leu Thr Leu Lys Phe
            35                  40                  45
Ile Cys Thr Thr Gly Lys Leu Pro Val Pro Trp Pro Thr Leu Val Thr
        50                  55                  60
Thr Leu Thr Trp Gly Val Gln Cys Phe Ser Arg Tyr Pro Asp His Met
65                  70                  75                  80
Lys Gln His Asp Phe Phe Lys Ser Ala Met Pro Glu Gly Tyr Val Gln
                85                  90                  95
Glu Arg Thr Ile Phe Phe Lys Asp Asp Gly Asn Tyr Lys Thr Arg Ala
            100                 105                 110
Glu Val Lys Phe Glu Gly Asp Thr Leu Val Asn Arg Ile Glu Leu Lys
        115                 120                 125
Gly Ile Asp Phe Lys Glu Asp Gly Asn Ile Leu Gly His Lys Leu Glu
    130                 135                 140
Tyr Asn Tyr Ile Ser His Asn Val Tyr Ile Thr Ala Asp Lys Gln Lys
145                 150                 155                 160
Asn Gly Ile Lys Ala His Phe Lys Ile Arg His Asn Ile Glu Asp Gly
                165                 170                 175
Ser Val Gln Leu Ala Asp His Tyr Gln Gln Asn Thr Pro Ile Gly Asp
            180                 185                 190
Gly Pro Val Leu Leu Pro Asp Asn His Tyr Leu Ser Thr Gln Ser Ala
        195                 200                 205
Leu Ser Lys Asp Pro Asn Glu Lys Arg Asp His Met Val Leu Leu Glu
    210                 215                 220
Phe Val Thr Ala Ala Glu Leu Met Ala Asp Gln Leu Thr Asp Asp Gln
225                 230                 235                 240
Ile Ser Glu Phe Lys Glu Ala Phe Ser Leu Phe Asp Gly Asp Gly Cys
                245                 250                 255
Ile Thr Thr Lys Glu Leu Gly Thr Val Met Arg Ser Leu Gly Gln Asn
            260                 265                 270
Pro Thr Glu Ala Glu Leu Gln Asp Met Ile Asn Glu Val Asp Gly Asn
        275                 280                 285
```

Gly Thr Ile Asp Phe Pro Glu Phe Leu Asn Leu Met Ala Arg Lys Met
        290                 295                 300

Lys Asp Thr Asp Ser Glu Glu Leu Lys Glu Ala Phe Arg Val Phe
305                 310                 315                 320

Asp Gln Asn Gly Phe Ile Ser Ala Ala Glu Leu Arg His Val Met Thr
                325                 330                 335

Asn Leu Gly Glu Lys Leu Thr Asp Glu Glu Val Asp Glu Met Ile Lys
            340                 345                 350

Glu Ala Asp Gly Asp Gly Gln Ile Asn Tyr Glu Glu Phe Val Lys Val
        355                 360                 365

Met Met Ala Lys Gly Gly Gly Ser Lys Arg Arg Trp Lys Lys Asn
370                 375                 380

Phe Ile Ala Val Ser Ala Ala Asn Arg Phe Lys Lys Ile Ser Ser Ser
385                 390                 395                 400

Gly Ala Leu Val Asp Met Val Ser Lys Gly Glu Glu Leu Phe Thr Gly
                405                 410                 415

Val Val Pro Ile Leu Val Glu Leu Asp Gly Asp Val Asn Gly His Lys
                420                 425                 430

Phe Ser Val Ser Gly Glu Gly Glu Gly Asp Ala Thr Tyr Gly Lys Leu
            435                 440                 445

Thr Leu Lys Phe Ile Cys Thr Thr Gly Lys Leu Pro Val Pro Trp Pro
450                 455                 460

Thr Leu Val Thr Thr Phe Gly Tyr Gly Val Gln Cys Phe Ala Arg Tyr
465                 470                 475                 480

Pro Asp His Met Lys Gln His Asp Phe Phe Lys Ser Ala Met Pro Glu
                485                 490                 495

Gly Tyr Val Gln Glu Arg Thr Ile Phe Phe Lys Asp Asp Gly Asn Tyr
                500                 505                 510

Lys Thr Arg Ala Glu Val Lys Phe Glu Gly Asp Thr Leu Val Asn Arg
            515                 520                 525

Ile Glu Leu Lys Gly Ile Asp Phe Lys Glu Asp Gly Asn Ile Leu Gly
530                 535                 540

His Lys Leu Glu Tyr Asn Tyr Asn Ser His Asn Val Tyr Ile Met Ala
545                 550                 555                 560

Asp Lys Gln Lys Asn Gly Ile Lys Val Asn Phe Lys Ile Arg His Asn
                565                 570                 575

Ile Glu Asp Gly Ser Val Gln Leu Ala Asp His Tyr Gln Gln Asn Thr
            580                 585                 590

Pro Ile Gly Asp Gly Pro Val Leu Leu Pro Asp Asn His Tyr Leu Ser
        595                 600                 605

Tyr Gln Ser Ala Leu Ser Lys Asp Pro Asn Glu Lys Arg Asp His Met
610                 615                 620

Val Leu Leu Glu Phe Val Thr Ala Ala Gly Ile Thr Leu Gly Met Asp
625                 630                 635                 640

Glu Leu Tyr Lys

<210> SEQ ID NO 39
<211> LENGTH: 234
<212> TYPE: DNA
<213> ORGANISM: artificial sequence
<220> FEATURE:
<223> OTHER INFORMATION: synthetic polynucleotide encoding CaM1

<400> SEQUENCE: 39

```
tccatggcgg atcagctcac cgacgatcag atctctgagt ttaaggaagc tttcagctta      60
ttcgacaagg atggtgatgg ttacattacc gccgcggagc tgggtactgt gatgcgttcc     120
cttggacaaa acccaaccga agcagagctt caagacatga tcaacgaagt ggctgctgct     180
ggtaacggta ccattgattt cccagagttc ttgaacctta tggctcgtaa gtga           234
```

```
<210> SEQ ID NO 40
<211> LENGTH: 77
<212> TYPE: PRT
<213> ORGANISM: artificial sequence
<220> FEATURE:
<223> OTHER INFORMATION: synthetic peptide CaM1

<400> SEQUENCE: 40
```

```
Ser Met Ala Asp Gln Leu Thr Asp Asp Gln Ile Ser Glu Phe Lys Glu
1               5                   10                  15

Ala Phe Ser Leu Phe Asp Lys Asp Gly Asp Gly Tyr Ile Thr Ala Ala
            20                  25                  30

Glu Leu Gly Thr Val Met Arg Ser Leu Gly Gln Asn Pro Thr Glu Ala
        35                  40                  45

Glu Leu Gln Asp Met Ile Asn Glu Val Ala Ala Ala Gly Asn Gly Thr
    50                  55                  60

Ile Asp Phe Pro Glu Phe Leu Asn Leu Met Ala Arg Lys
65                  70                  75
```

```
<210> SEQ ID NO 41
<211> LENGTH: 45
<212> TYPE: DNA
<213> ORGANISM: artificial sequence
<220> FEATURE:
<223> OTHER INFORMATION: synthetic oligonucleotide primer DGD S

<400> SEQUENCE: 41
gaagctttca gcttattcga cggtgatggt tacattaccg ccgcg                      45
```

```
<210> SEQ ID NO 42
<211> LENGTH: 45
<212> TYPE: DNA
<213> ORGANISM: artificial sequence
<220> FEATURE:
<223> OTHER INFORMATION: synthetic oligonucleotide primer DGD AS

<400> SEQUENCE: 42
cgcggcggta atgtaaccat caccgtcgaa taagctgaaa gcttc                      45
```

```
<210> SEQ ID NO 43
<211> LENGTH: 52
<212> TYPE: DNA
<213> ORGANISM: artificial sequence
<220> FEATURE:
<223> OTHER INFORMATION: synthetic oligonucleotide primer S-TEV-eCFP-
      BamHI

<400> SEQUENCE: 43
gagaggatcc gagaacctgt acttccagtc catggtgagc aagggcgagg ag              52
```

```
<210> SEQ ID NO 44
<211> LENGTH: 33
<212> TYPE: DNA
<213> ORGANISM: artificial sequence
<220> FEATURE:
<223> OTHER INFORMATION: synthetic oligonucleotide primer AS-eCFP-SacI

<400> SEQUENCE: 44
```

-continued

```
taaagagctc ggcggcggtc acgaactcca gca                                     33
```

<210> SEQ ID NO 45
<211> LENGTH: 31
<212> TYPE: DNA
<213> ORGANISM: artificial sequence
<220> FEATURE:
<223> OTHER INFORMATION: synthetic oligonucleotide primer S-eYFP-SalI

<400> SEQUENCE: 45

```
tatagtcgac atggtgagca agggcgagga g                                       31
```

<210> SEQ ID NO 46
<211> LENGTH: 35
<212> TYPE: DNA
<213> ORGANISM: artificial sequence
<220> FEATURE:
<223> OTHER INFORMATION: synthetic oligonucleotide primer
      AS-eYFP-HindIII

<400> SEQUENCE: 46

```
gggcaagctt ttacttgtac agctcgtcca tgccg                                   35
```

<210> SEQ ID NO 47
<211> LENGTH: 1959
<212> TYPE: DNA
<213> ORGANISM: artificial sequence
<220> FEATURE:
<223> OTHER INFORMATION: synthetic polynucleotide encoding Cameleon
      biosensor WT

<400> SEQUENCE: 47

```
tccatggtga gcaagggcga ggagctgttc accggggtgg tgcccatcct ggtcgagctg       60
gacggcgacg taaacggcca caggttcagc gtgtccggcg agggcgaggg cgatgccacc      120
tacggcaagc tgaccctgaa gttcatctgc accaccggca agctgcccgt gccctggccc      180
accctcgtga ccaccctgac ctggggcgtg cagtgcttca gccgctaccc cgaccacatg      240
aagcagcacg acttcttcaa gtccgccatg cccgaaggct acgtccagga gcgtaccatc      300
ttcttcaagg acgacggcaa ctacaagacc cgcgccgagg tgaagttcga gggcgacacc      360
ctggtgaacc gcatcgagct gaagggcatc gacttcaagg aggacggcaa catcctgggg      420
cacaagctgg agtacaacta catcagccac aacgtctata tcaccgccga caagcagaag      480
aacggcatca aggcccactt caagatccgc cacaacatcg aggacggcag cgtgcagctc      540
gccgaccact accagcagaa cacccccatc ggcgacggcc ccgtgctgct gcccgacaac      600
cactacctga gcacccagtc cgccctgagc aaagacccca acgagaagcg cgatcacatg      660
gtcctgctgg agttcgtgac cgccgccgag ctcatggcgg atcagttgac cgacgatcag      720
atctctgaat taaggaagc cttcagctta ttcgacaaag atggtgatgg ttgcattacc      780
accaaggaac tgggtactgt gatgcgttcc ctgggccaaa acccgaccga agcagagctg      840
caagacatga tcaacgaagt ggatgcggat ggtaacggta ccattgattt cccggaattc      900
ttgaacctga tggcccgtaa gatgaaagac accgacagcg aggaagagct gaaagaagcc      960
ttccgcgttt tcgacaaaga ccagaacggt ttcatcagcg cagcggaact gcgccatgtg     1020
atgaccaacc tgggcgaaaa actgacggat gaagaagttg atgagatgat caagaagcg     1080
gatgtggatg gtgatggtca gattaactac aagagtttg ttaaggtgat gatggcgaaa     1140
ggcggtggcg gtagcaaacg tcgctggaaa aaaaacttta ttgcggtgag cgcggccaac     1200
```

```
cgctttaaaa aaattagctc gagcggcgcg ctggtcgaca tggtgagcaa gggcgaggag    1260
ctgttcaccg gggtggtgcc catcctggtc gagctggacg gcgacgtaaa cggccacaag    1320
ttcagcgtgt ccggcgaggg cgagggcgat gccacctacg gcaagctgac cctgaagttc    1380
atctgcacca ccggcaagct gcccgtgccc tggcccaccc tcgtgaccac cttcggctac    1440
ggcgtgcagt gcttcgcccg ctaccccgac cacatgaagc agcacgactt cttcaagtcc    1500
gccatgcccg aaggctacgt ccaggagcgc accatcttct tcaaggacga cggcaactac    1560
aagacccgcg ccgaggtgaa gttcgagggc gacaccctgg tgaaccgcat cgagctgaag    1620
ggcatcgact tcaaggagga cggcaacatc ctggggcaca gctggagta caactacaac    1680
agccacaacg tctatatcat ggccgacaag cagaagaacg gcatcaaggt gaacttcaag    1740
atccgccaca acatcgagga cggcagcgtg cagctcgccg accactacca gcagaacacc    1800
cccatcggcg acggccccgt gctgctgccc gacaaccact acctgagcta ccagtccgcc    1860
ctgagcaaag accccaacga gaagcgcgat cacatggtcc tgctggagtt cgtgaccgcc    1920
gccgggatca ctctcggcat ggacgagctg tacaagtaa                           1959
```

<210> SEQ ID NO 48
<211> LENGTH: 652
<212> TYPE: PRT
<213> ORGANISM: artificial sequence
<220> FEATURE:
<223> OTHER INFORMATION: synthetic protein Cameleon biosensor WT

<400> SEQUENCE: 48

```
Ser Met Val Ser Lys Gly Glu Glu Leu Phe Thr Gly Val Val Pro Ile
1               5                   10                  15

Leu Val Glu Leu Asp Gly Asp Val Asn Gly His Arg Phe Ser Val Ser
            20                  25                  30

Gly Glu Gly Glu Gly Asp Ala Thr Tyr Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Trp Gly Val Gln Cys Phe Ser Arg Tyr Pro Asp His Met
65                  70                  75                  80

Lys Gln His Asp Phe Phe Lys Ser Ala Met Pro Glu Gly Tyr Val Gln
                85                  90                  95

Glu Arg Thr Ile Phe Phe Lys Asp Asp Gly Asn Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Tyr Ile Ser His Asn Val Tyr Ile Thr Ala Asp Lys Gln Lys
145                 150                 155                 160

Asn Gly Ile Lys Ala His Phe Lys Ile Arg His Asn Ile Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asn His Tyr Leu Ser Thr Gln Ser Ala
        195                 200                 205

Leu Ser Lys Asp Pro Asn Glu Lys Arg Asp His Met Val Leu Leu Glu
    210                 215                 220

Phe Val Thr Ala Ala Glu Leu Met Ala Asp Gln Leu Thr Asp Asp Gln
```

```
              225                 230                 235                 240
        Ile Ser Glu Phe Lys Glu Ala Phe Ser Leu Phe Asp Lys Asp Gly Asp
                        245                 250                 255
        Gly Cys Ile Thr Thr Lys Glu Leu Gly Thr Val Met Arg Ser Leu Gly
                        260                 265                 270
        Gln Asn Pro Thr Glu Ala Glu Leu Gln Asp Met Ile Asn Glu Val Asp
                        275                 280                 285
        Ala Asp Gly Asn Gly Thr Ile Asp Phe Pro Glu Phe Leu Asn Leu Met
            290                 295                 300
        Ala Arg Lys Met Lys Asp Thr Asp Ser Glu Glu Leu Lys Glu Ala
        305                 310                 315                 320
        Phe Arg Val Phe Asp Lys Asp Gln Asn Gly Phe Ile Ser Ala Ala Glu
                        325                 330                 335
        Leu Arg His Val Met Thr Asn Leu Gly Glu Lys Leu Thr Asp Glu Glu
                        340                 345                 350
        Val Asp Glu Met Ile Lys Glu Ala Asp Val Asp Gly Asp Gly Gln Ile
                        355                 360                 365
        Asn Tyr Glu Glu Phe Val Lys Val Met Met Ala Lys Gly Gly Gly
            370                 375                 380
        Ser Lys Arg Arg Trp Lys Lys Asn Phe Ile Ala Val Ser Ala Ala Asn
        385                 390                 395                 400
        Arg Phe Lys Lys Ile Ser Ser Ser Gly Ala Leu Val Asp Met Val Ser
                        405                 410                 415
        Lys Gly Glu Glu Leu Phe Thr Gly Val Val Pro Ile Leu Val Glu Leu
                        420                 425                 430
        Asp Gly Asp Val Asn Gly His Lys Phe Ser Val Ser Gly Glu Gly Glu
                        435                 440                 445
        Gly Asp Ala Thr Tyr Gly Lys Leu Thr Leu Lys Phe Ile Cys Thr Thr
            450                 455                 460
        Gly Lys Leu Pro Val Pro Trp Pro Thr Leu Val Thr Thr Phe Gly Tyr
        465                 470                 475                 480
        Gly Val Gln Cys Phe Ala Arg Tyr Pro Asp His Met Lys Gln His Asp
                        485                 490                 495
        Phe Phe Lys Ser Ala Met Pro Glu Gly Tyr Val Gln Glu Arg Thr Ile
                        500                 505                 510
        Phe Phe Lys Asp Asp Gly Asn Tyr Lys Thr Arg Ala Glu Val Lys Phe
                        515                 520                 525
        Glu Gly Asp Thr Leu Val Asn Arg Ile Glu Leu Lys Gly Ile Asp Phe
            530                 535                 540
        Lys Glu Asp Gly Asn Ile Leu Gly His Lys Leu Glu Tyr Asn Tyr Asn
        545                 550                 555                 560
        Ser His Asn Val Tyr Ile Met Ala Asp Lys Gln Lys Asn Gly Ile Lys
                        565                 570                 575
        Val Asn Phe Lys Ile Arg His Asn Ile Glu Asp Gly Ser Val Gln Leu
                        580                 585                 590
        Ala Asp His Tyr Gln Gln Asn Thr Pro Ile Gly Asp Gly Pro Val Leu
                        595                 600                 605
        Leu Pro Asp Asn His Tyr Leu Ser Tyr Gln Ser Ala Leu Ser Lys Asp
                        610                 615                 620
        Pro Asn Glu Lys Arg Asp His Met Val Leu Leu Glu Phe Val Thr Ala
        625                 630                 635                 640
        Ala Gly Ile Thr Leu Gly Met Asp Glu Leu Tyr Lys
                        645                 650
```

<210> SEQ ID NO 49
<211> LENGTH: 40
<212> TYPE: DNA
<213> ORGANISM: artificial sequence
<220> FEATURE:
<223> OTHER INFORMATION: synthetic oligonucleotide primer S-delta

<400> SEQUENCE: 49
ggaagccttc agcttattcg acggtgatgg ttgcattacc          40

<210> SEQ ID NO 50
<211> LENGTH: 40
<212> TYPE: DNA
<213> ORGANISM: artificial sequence
<220> FEATURE:
<223> OTHER INFORMATION: synthetic oligonucleotide primer AS-delta

<400> SEQUENCE: 50
ggtaatgcaa ccatcaccgt cgaataagct gaaggcttcc          40

<210> SEQ ID NO 51
<211> LENGTH: 34
<212> TYPE: DNA
<213> ORGANISM: artificial sequence
<220> FEATURE:
<223> OTHER INFORMATION: synthetic oligonucleotide primer S-S2M

<400> SEQUENCE: 51
ggtaccgtta ccagcagcag ccacttcgtt gatc               34

<210> SEQ ID NO 52
<211> LENGTH: 34
<212> TYPE: DNA
<213> ORGANISM: artificial sequence
<220> FEATURE:
<223> OTHER INFORMATION: synthetic oligonucleotide primer AS-S2M

<400> SEQUENCE: 52
gatcaacgaa gtggctgctg ctggtaacgg tacc               34

<210> SEQ ID NO 53
<211> LENGTH: 1959
<212> TYPE: DNA
<213> ORGANISM: artificial sequence
<220> FEATURE:
<223> OTHER INFORMATION: synthetic polynucleotide encoding Cameleon
      biosensor WT-S2M

<400> SEQUENCE: 53
tccatggtga gcaagggcga ggagctgttc accggggtgg tgcccatcct ggtcgagctg     60
gacggcgacg taaacggcca caggttcagc gtgtccggcg agggcgaggg cgatgccacc    120
tacggcaagc tgaccctgaa gttcatctgc accaccggca agctgcccgt gccctggccc    180
accctcgtga ccaccctgac ctggggcgtg cagtgcttca gccgctaccc cgaccacatg    240
aagcagcacg acttcttcaa gtccgccatg cccgaaggct acgtccagga gcgtaccatc    300
ttcttcaagg acgacggcaa ctacaagacc cgcgccgagg tgaagttcga gggcgacacc    360
ctggtgaacc gcatcgagct gaagggcatc gacttcaagg aggacggcaa catcctgggg    420
cacaagctgg agtacaacta catcagccac aacgtctata tcaccgccga caagcagaag    480
aacggcatca aggcccactt caagatccgc cacaacatcg aggacggcag cgtgcagctc    540
gccgaccact accagcagaa cacccccatc ggcgacggcc ccgtgctgct gcccgacaac    600

```
cactacctga gcacccagtc cgccctgagc aaagacccca acgagaagcg cgatcacatg    660
gtcctgctgg agttcgtgac cgccgccgag ctcatggcgg atcagttgac cgacgatcag    720
atctctgaat taaggaagc cttcagctta ttcgacaaag atggtgatgg ttgcattacc    780
accaaggaac tgggtactgt gatgcgttcc ctgggccaaa acccgaccga agcagagctg    840
caagacatga tcaacgaagt ggctgcggct ggtaacggta ccattgattt cccggaattc    900
ttgaacctga tggcccgtaa gatgaaagac accgacagcg aggaagagct gaaagaagcc    960
ttccgcgttt tcgacaaaga ccagaacggt tcatcagcg cagcggaact cgccatgtg   1020 atgaccaacc tgggcgaaaa actgacggat gaagaagttg atgagatgat caaagaagcg   1080
gatgtggatg gtgatggtca gattaactac gaagagtttg ttaaggtgat gatggcgaaa   1140
ggcggtggcg gtagcaaacg tcgctggaaa aaaaacttta ttgcggtgag cgcggccaac   1200
cgctttaaaa aaattagctc gagcggcgcg ctggtcgaca tggtgagcaa gggcgaggag   1260
ctgttcaccg ggtggtgcc catcctggtc gagctggacg gcgacgtaaa cggccacaag   1320
ttcagcgtgt ccggcgaggg cgaggcgat gccacctacg gcaagctgac cctgaagttc   1380
atctgcacca ccggcaagct gcccgtgccc tggcccaccc tcgtgaccac cttcggctac   1440
ggcgtgcagt gcttcgcccg ctaccccgac cacatgaagc agcacgactt cttcaagtcc   1500
gccatgcccg aaggctacgt ccaggagcgc accatcttct tcaaggacga cggcaactac   1560
aagacccgcg ccgaggtgaa gttcgagggc gacaccctgg tgaaccgcat cgagctgaag   1620
ggcatcgact tcaaggagga cggcaacatc ctggggcaca gctggagta caactacaac   1680 agccacaacg tctatatcat ggccgacaag cagaagaacg gcatcaaggt gaacttcaag   1740
atccgccaca acatcgagga cggcagcgtg cagctcgccg accactacca gcagaacacc   1800
cccatcggcg acggccccgt gctgctgccc gacaaccact acctgagcta ccagtccgcc   1860
ctgagcaaag accccaacga gaagcgcgat cacatggtcc tgctggagtt cgtgaccgcc   1920
gccgggatca ctctcggcat ggacgagctg tacaagtaa                         1959
```

<210> SEQ ID NO 54
<211> LENGTH: 652
<212> TYPE: PRT
<213> ORGANISM: artificial sequence
<220> FEATURE:
<223> OTHER INFORMATION: synthetic protein Cameleon biosensor WT-S2M

<400> SEQUENCE: 54

```
Ser Met Val Ser Lys Gly Glu Glu Leu Phe Thr Gly Val Val Pro Ile
1               5                  10                  15

Leu Val Glu Leu Asp Gly Asp Val Asn Gly His Arg Phe Ser Val Ser
            20                  25                  30

Gly Glu Gly Glu Gly Asp Ala Thr Tyr Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Trp Gly Val Gln Cys Phe Ser Arg Tyr Pro Asp His Met
65                  70                  75                  80

Lys Gln His Asp Phe Phe Lys Ser Ala Met Pro Glu Gly Tyr Val Gln
                85                  90                  95

Glu Arg Thr Ile Phe Phe Lys Asp Asp Gly Asn Tyr Lys Thr Arg Ala
            100                 105                 110

Glu Val Lys Phe Glu Gly Asp Thr Leu Val Asn Arg Ile Glu Leu Lys
```

```
              115                 120                 125
Gly Ile Asp Phe Lys Glu Asp Gly Asn Ile Leu Gly His Lys Leu Glu
130                 135                 140

Tyr Asn Tyr Ile Ser His Asn Val Tyr Ile Thr Ala Asp Lys Gln Lys
145                 150                 155                 160

Asn Gly Ile Lys Ala His Phe Lys Ile Arg His Asn Ile Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asn His Tyr Leu Ser Thr Gln Ser Ala
        195                 200                 205

Leu Ser Lys Asp Pro Asn Glu Lys Arg Asp His Met Val Leu Leu Glu
210                 215                 220

Phe Val Thr Ala Ala Glu Leu Met Ala Asp Gln Leu Thr Asp Asp Gln
225                 230                 235                 240

Ile Ser Glu Phe Lys Glu Ala Phe Ser Leu Phe Asp Lys Asp Gly Asp
                245                 250                 255

Gly Cys Ile Thr Thr Lys Glu Leu Gly Thr Val Met Arg Ser Leu Gly
            260                 265                 270

Gln Asn Pro Thr Glu Ala Glu Leu Gln Asp Met Ile Asn Glu Val Ala
        275                 280                 285

Ala Ala Gly Asn Gly Thr Ile Asp Phe Pro Glu Phe Leu Asn Leu Met
290                 295                 300

Ala Arg Lys Met Lys Asp Thr Asp Ser Glu Glu Leu Lys Glu Ala
305                 310                 315                 320

Phe Arg Val Phe Asp Lys Asp Gln Asn Gly Phe Ile Ser Ala Ala Glu
                325                 330                 335

Leu Arg His Val Met Thr Asn Leu Gly Glu Lys Leu Thr Asp Glu Glu
            340                 345                 350

Val Asp Glu Met Ile Lys Glu Ala Asp Val Asp Gly Asp Gly Gln Ile
        355                 360                 365

Asn Tyr Glu Glu Phe Val Lys Val Met Met Ala Lys Gly Gly Gly Gly
370                 375                 380

Ser Lys Arg Arg Trp Lys Lys Asn Phe Ile Ala Val Ser Ala Ala Asn
385                 390                 395                 400

Arg Phe Lys Lys Ile Ser Ser Ser Gly Ala Leu Val Asp Met Val Ser
                405                 410                 415

Lys Gly Glu Glu Leu Phe Thr Gly Val Val Pro Ile Leu Val Glu Leu
            420                 425                 430

Asp Gly Asp Val Asn Gly His Lys Phe Ser Val Ser Gly Glu Gly Glu
        435                 440                 445

Gly Asp Ala Thr Tyr Gly Lys Leu Thr Leu Lys Phe Ile Cys Thr Thr
450                 455                 460

Gly Lys Leu Pro Val Pro Trp Pro Thr Leu Val Thr Thr Phe Gly Tyr
465                 470                 475                 480

Gly Val Gln Cys Phe Ala Arg Tyr Pro Asp His Met Lys Gln His Asp
                485                 490                 495

Phe Phe Lys Ser Ala Met Pro Glu Gly Tyr Val Gln Glu Arg Thr Ile
            500                 505                 510

Phe Phe Lys Asp Asp Gly Asn Tyr Lys Thr Arg Ala Glu Val Lys Phe
        515                 520                 525

Glu Gly Asp Thr Leu Val Asn Arg Ile Glu Leu Lys Gly Ile Asp Phe
530                 535                 540
```

Lys Glu Asp Gly Asn Ile Leu Gly His Lys Leu Glu Tyr Asn Tyr Asn
545                 550                 555                 560

Ser His Asn Val Tyr Ile Met Ala Asp Lys Gln Lys Asn Gly Ile Lys
                565                 570                 575

Val Asn Phe Lys Ile Arg His Asn Ile Glu Asp Gly Ser Val Gln Leu
            580                 585                 590

Ala Asp His Tyr Gln Gln Asn Thr Pro Ile Gly Asp Gly Pro Val Leu
        595                 600                 605

Leu Pro Asp Asn His Tyr Leu Ser Tyr Gln Ser Ala Leu Ser Lys Asp
    610                 615                 620

Pro Asn Glu Lys Arg Asp His Met Val Leu Leu Glu Phe Val Thr Ala
625                 630                 635                 640

Ala Gly Ile Thr Leu Gly Met Asp Glu Leu Tyr Lys
                645                 650

<210> SEQ ID NO 55
<211> LENGTH: 231
<212> TYPE: DNA
<213> ORGANISM: artificial sequence
<220> FEATURE:
<223> OTHER INFORMATION: synthetic nucleotide encoding CaM-delta3
      polypeptide

<400> SEQUENCE: 55
tccatggcgg atcagctcac cgacgatcag atctctgagt ttaaggaagc tttcagctta     60
ttcgacaagg gtgatggtta cattaccgcc gcggagctgg gtactgtgat gcgttccctt    120
ggacaaaacc caaccgaagc agagcttcaa gacatgatca cgaagtggc tgctgctggt     180 aacggtacca ttgatttccc agagttcttg aaccttatgg ctcgtaagtg a             231

<210> SEQ ID NO 56
<211> LENGTH: 76
<212> TYPE: PRT
<213> ORGANISM: artificial sequence
<220> FEATURE:
<223> OTHER INFORMATION: synthetic polypeptide CaM-delta3

<400> SEQUENCE: 56

Ser Met Ala Asp Gln Leu Thr Asp Asp Gln Ile Ser Glu Phe Lys Glu
1               5                   10                  15

Ala Phe Ser Leu Phe Asp Lys Gly Asp Gly Tyr Ile Thr Ala Ala Glu
                20                  25                  30

Leu Gly Thr Val Met Arg Ser Leu Gly Gln Asn Pro Thr Glu Ala Glu
            35                  40                  45

Leu Gln Asp Met Ile Asn Glu Val Ala Ala Gly Asn Gly Thr Ile
        50                  55                  60

Asp Phe Pro Glu Phe Leu Asn Leu Met Ala Arg Lys
65                  70                  75

<210> SEQ ID NO 57
<211> LENGTH: 36
<212> TYPE: DNA
<213> ORGANISM: artificial sequence
<220> FEATURE:
<223> OTHER INFORMATION: synthetic primer S-delta3Y

<400> SEQUENCE: 57
ttcagcttat tcgacaaggg tgatggttac attacc                                36

<210> SEQ ID NO 58
<211> LENGTH: 36
<212> TYPE: DNA
<213> ORGANISM: artificial sequence
<220> FEATURE:
<223> OTHER INFORMATION: synthetic primer AS-delta3Y

<400> SEQUENCE: 58
ggtaatgtaa ccatcaccct tgtcgaataa gctgaa                                36

<210> SEQ ID NO 59
<211> LENGTH: 228
<212> TYPE: DNA
<213> ORGANISM: artificial sequence
<220> FEATURE:
<223> OTHER INFORMATION: synthetic polynucleotide encoding polypeptide
      CaM-delta-WT

<400> SEQUENCE: 59
tccatggcgg atcagctcac cgacgatcag atctctgagt ttaaggaagc tttcagctta      60
ttcgacggtg atggttacat taccaccaag gagctgggta ctgtgatgcg ttcccttgga     120
caaaacccaa ccgaagcaga gcttcaagac atgatcaacg aagtggctgc tgctggtaac    180
ggtaccattg atttcccaga gttcttgaac cttatggctc gtaagtga                 228

<210> SEQ ID NO 60
<211> LENGTH: 75
<212> TYPE: PRT
<213> ORGANISM: artificial sequence
<220> FEATURE:
<223> OTHER INFORMATION: synthetic polypeptide CaM-delta-WT

<400> SEQUENCE: 60

Ser Met Ala Asp Gln Leu Thr Asp Asp Gln Ile Ser Glu Phe Lys Glu
1               5                   10                  15

Ala Phe Ser Leu Phe Asp Gly Asp Gly Tyr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Ala Ala Ala Gly Asn Gly Thr Ile Asp
    50                  55                  60

Phe Pro Glu Phe Leu Asn Leu Met Ala Arg Lys
65                  70                  75

<210> SEQ ID NO 61
<211> LENGTH: 648
<212> TYPE: PRT
<213> ORGANISM: artificial sequence
<220> FEATURE:
<223> OTHER INFORMATION: synthetic protein Cameleon biosensor
      delta1-delta3

<400> SEQUENCE: 61

Ser Met Val Ser Lys Gly Glu Glu Leu Phe Thr Gly Val Val Pro Ile
1               5                   10                  15

Leu Val Glu Leu Asp Gly Asp Val Asn Gly His Arg Phe Ser Val Ser
            20                  25                  30

Gly Glu Gly Glu Gly Asp Ala Thr Tyr Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Trp Gly Val Gln Cys Phe Ser Arg Tyr Pro Asp His Met

```
            65                  70                  75                  80
Lys Gln His Asp Phe Phe Lys Ser Ala Met Pro Glu Gly Tyr Val Gln
                    85                  90                  95

Glu Arg Thr Ile Phe Phe Lys Asp Asp Gly Asn Tyr Lys Thr Arg Ala
                100                 105                 110

Glu Val Lys Phe Glu Gly Asp Thr Leu Val Asn Arg Ile Glu Leu Lys
                115                 120                 125

Gly Ile Asp Phe Lys Glu Asp Gly Asn Ile Leu Gly His Lys Leu Glu
130                 135                 140

Tyr Asn Tyr Ile Ser His Asn Val Tyr Ile Thr Ala Asp Lys Gln Lys
145                 150                 155                 160

Asn Gly Ile Lys Ala His Phe Lys Ile Arg His Asn Ile Glu Asp Gly
                165                 170                 175

Ser Val Gln Leu Ala Asp His Tyr Gln Gln Asn Thr Pro Ile Gly Asp
                180                 185                 190

Gly Pro Val Leu Leu Pro Asp Asn His Tyr Leu Ser Thr Gln Ser Ala
                195                 200                 205

Leu Ser Lys Asp Pro Asn Glu Lys Arg Asp His Met Val Leu Leu Glu
210                 215                 220

Phe Val Thr Ala Ala Glu Leu Met Ala Asp Gln Leu Thr Asp Asp Gln
225                 230                 235                 240

Ile Ser Glu Phe Lys Glu Ala Phe Ser Leu Phe Asp Gly Asp Gly Cys
                245                 250                 255

Ile Thr Thr Lys Glu Leu Gly Thr Val Met Arg Ser Leu Gly Gln Asn
                260                 265                 270

Pro Thr Glu Ala Glu Leu Gln Asp Met Ile Asn Glu Val Asp Ala Asp
                275                 280                 285

Gly Asn Gly Thr Ile Asp Phe Pro Glu Phe Leu Asn Leu Met Ala Arg
                290                 295                 300

Lys Met Lys Asp Thr Asp Ser Glu Glu Glu Leu Lys Glu Ala Phe Arg
305                 310                 315                 320

Val Phe Asp Gln Asn Gly Phe Ile Ser Ala Ala Glu Leu Arg His Val
                325                 330                 335

Met Thr Asn Leu Gly Glu Lys Leu Thr Asp Glu Glu Val Asp Glu Met
                340                 345                 350

Ile Lys Glu Ala Asp Val Asp Gly Asp Gly Gln Ile Asn Tyr Glu Glu
                355                 360                 365

Phe Val Lys Val Met Met Ala Lys Gly Gly Gly Ser Lys Arg Arg
                370                 375                 380

Trp Lys Lys Asn Phe Ile Ala Val Ser Ala Ala Asn Arg Phe Lys Lys
385                 390                 395                 400

Ile Ser Ser Ser Gly Ala Leu Val Asp Met Val Ser Lys Gly Glu Glu
                405                 410                 415

Leu Phe Thr Gly Val Val Pro Ile Leu Val Glu Leu Asp Gly Asp Val
                420                 425                 430

Asn Gly His Lys Phe Ser Val Ser Gly Glu Gly Glu Gly Asp Ala Thr
                435                 440                 445

Tyr Gly Lys Leu Thr Leu Lys Phe Ile Cys Thr Thr Gly Lys Leu Pro
                450                 455                 460

Val Pro Trp Pro Thr Leu Val Thr Thr Phe Gly Tyr Gly Val Gln Cys
465                 470                 475                 480

Phe Ala Arg Tyr Pro Asp His Met Lys Gln His Asp Phe Phe Lys Ser
                485                 490                 495
```

```
Ala Met Pro Glu Gly Tyr Val Gln Glu Arg Thr Ile Phe Phe Lys Asp
            500                 505                 510

Asp Gly Asn Tyr Lys Thr Arg Ala Glu Val Lys Phe Glu Gly Asp Thr
        515                 520                 525

Leu Val Asn Arg Ile Glu Leu Lys Gly Ile Asp Phe Lys Glu Asp Gly
    530                 535                 540

Asn Ile Leu Gly His Lys Leu Glu Tyr Asn Tyr Asn Ser His Asn Val
545                 550                 555                 560

Tyr Ile Met Ala Asp Lys Gln Lys Asn Gly Ile Lys Val Asn Phe Lys
                565                 570                 575

Ile Arg His Asn Ile Glu Asp Gly Ser Val Gln Leu Ala Asp His Tyr
            580                 585                 590

Gln Gln Asn Thr Pro Ile Gly Asp Gly Pro Val Leu Leu Pro Asp Asn
        595                 600                 605

His Tyr Leu Ser Tyr Gln Ser Ala Leu Ser Lys Asp Pro Asn Glu Lys
    610                 615                 620

Arg Asp His Met Val Leu Leu Glu Phe Val Thr Ala Ala Gly Ile Thr
625                 630                 635                 640

Leu Gly Met Asp Glu Leu Tyr Lys
                645

<210> SEQ ID NO 62
<211> LENGTH: 1947
<212> TYPE: DNA
<213> ORGANISM: artificial sequence
<220> FEATURE:
<223> OTHER INFORMATION: synthetic polynucleotide encoding protein
      cameleon biosensor delta1-delta3

<400> SEQUENCE: 62
tccatggtga gcaagggcga ggagctgttc accggggtgg tgcccatcct ggtcgagctg      60
gacggcgacg taaacggcca caggttcagc gtgtccggcg agggcgaggg cgatgccacc     120
tacggcaagc tgaccctgaa gttcatctgc accaccggca agctgcccgt gccctggccc     180
accctcgtga ccaccctgac ctggggcgtg cagtgcttca gccgctaccc cgaccacatg     240
aagcagcacg acttcttcaa gtccgccatg cccgaaggct acgtccagga gcgtaccatc     300
ttcttcaagg acgacggcaa ctacaagacc cgcgccgagg tgaagttcga gggcgacacc     360
ctggtgaacc gcatcgagct gaagggcatc gacttcaagg aggacggcaa catcctgggg     420
cacaagctgg agtacaacta catcagccac aacgtctata tcaccgccga caagcagaag     480
aacggcatca aggcccactt caagatccgc cacaacatcg aggacggcag cgtgcagctc     540
gccgaccact accagcagaa cacccccatc ggcgacggcc ccgtgctgct gcccgacaac     600
cactacctga gcacccagtc cgccctgagc aaagacccca acgagaagcg cgatcacatg     660
gtcctgctgg agttcgtgac cgccgccgag ctcatggcgg atcagttgac cgacgatcag     720
atctctgaat taaggaagc cttcagctta ttcgacggtg atggttgcat taccaccaag      780
gaactgggta ctgtgatgcg ttccctgggc caaaacccga ccgaagcaga gctgcaagac     840
atgatcaacg aagtggatgc ggatggtaac ggtaccattg atttcccgga attcttgaac     900
ctgatggccc gtaagatgaa agacaccgac agcgaggaag agctgaaaga agccttccgc     960
gttttcgacc agaacggttt catcagcgca gcggaactgc gccatgtgat gaccaacctg    1020
ggcgaaaaac tgacggatga agaagttgat gagatgatca agaagcgga tgtggatggt    1080 gatggtcaga ttaactacga agagtttgtt aaggtgatga tggcgaaagg cggtggcggt    1140
```

-continued

```
agcaaacgtc gctggaaaaa aaactttatt gcggtgagcg cggccaaccg ctttaaaaaa    1200
attagctcga gcggcgcgct ggtcgacatg gtgagcaagg gcgaggagct gttcaccggg    1260
gtggtgccca tcctggtcga gctggacggc gacgtaaacg gccacaagtt cagcgtgtcc    1320
ggcgagggcg agggcgatgc cacctacggc aagctgaccc tgaagttcat ctgcaccacc    1380
ggcaagctgc ccgtgccctg gcccaccctc gtgaccacct tcggctacgg cgtgcagtgc    1440
ttcgcccgct accccgacca catgaagcag cacgacttct tcaagtccgc catgcccgaa    1500
ggctacgtcc aggagcgcac catcttcttc aaggacgacg gcaactacaa gacccgcgcc    1560
gaggtgaagt tcgagggcga cacccctggtg aaccgcatcg agctgaaggg catcgacttc    1620
aaggaggacg gcaacatcct ggggcacaag ctggagtaca actacaacag ccacaacgtc    1680
tatatcatgg ccgacaagca gaagaacggc atcaaggtga acttcaagat ccgccacaac    1740
atcgaggacg gcagcgtgca gctcgccgac cactaccagc agaacacccc catcggcgac    1800
ggccccgtgc tgctgcccga caaccactac ctgagctacc agtccgccct gagcaaagac    1860
cccaacgaga gcgcgatca catggtcctg ctggagttcg tgaccgccgc cgggatcact    1920
ctcggcatgg acgagctgta caagtaa                                        1947
```

<210> SEQ ID NO 63
<211> LENGTH: 646
<212> TYPE: PRT
<213> ORGANISM: artificial sequence
<220> FEATURE:
<223> OTHER INFORMATION: synthetic protein Cameleon biosensor delta1-delta2-delta3

<400> SEQUENCE: 63

```
Ser Met Val Ser Lys Gly Glu Glu Leu Phe Thr Gly Val Val Pro Ile
1               5                   10                  15

Leu Val Glu Leu Asp Gly Asp Val Asn Gly His Arg Phe Ser Val Ser
            20                  25                  30

Gly Glu Gly Glu Gly Asp Ala Thr Tyr Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Trp Gly Val Gln Cys Phe Ser Arg Tyr Pro Asp His Met
65                  70                  75                  80

Lys Gln His Asp Phe Phe Lys Ser Ala Met Pro Glu Gly Tyr Val Gln
                85                  90                  95

Glu Arg Thr Ile Phe Phe Lys Asp Asp Gly Asn Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Tyr Ile Ser His Asn Val Tyr Ile Thr Ala Asp Lys Gln Lys
145                 150                 155                 160

Asn Gly Ile Lys Ala His Phe Lys Ile Arg His Asn Ile Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asn His Tyr Leu Ser Thr Gln Ser Ala
        195                 200                 205
```

```
Leu Ser Lys Asp Pro Asn Glu Lys Arg Asp His Met Val Leu Glu
    210                 215                 220
Phe Val Thr Ala Ala Glu Leu Met Ala Asp Gln Leu Thr Asp Asp Gln
225                 230                 235                 240
Ile Ser Glu Phe Lys Glu Ala Phe Ser Leu Phe Asp Gly Asp Gly Cys
                245                 250                 255
Ile Thr Thr Lys Glu Leu Gly Thr Val Met Arg Ser Leu Gly Gln Asn
                260                 265                 270
Pro Thr Glu Ala Glu Leu Gln Asp Met Ile Asn Glu Val Asp Gly Asn
            275                 280                 285
Gly Thr Ile Asp Phe Pro Glu Phe Leu Asn Leu Met Ala Arg Lys Met
    290                 295                 300
Lys Asp Thr Asp Ser Glu Glu Glu Leu Lys Glu Ala Phe Arg Val Phe
305                 310                 315                 320
Asp Gln Asn Gly Phe Ile Ser Ala Ala Glu Leu Arg His Val Met Thr
                325                 330                 335
Asn Leu Gly Glu Lys Leu Thr Asp Glu Glu Val Asp Glu Met Ile Lys
                340                 345                 350
Glu Ala Asp Val Asp Gly Asp Gly Gln Ile Asn Tyr Glu Glu Phe Val
            355                 360                 365
Lys Val Met Met Ala Lys Gly Gly Gly Ser Lys Arg Arg Trp Lys
    370                 375                 380
Lys Asn Phe Ile Ala Val Ser Ala Ala Asn Arg Phe Lys Lys Ile Ser
385                 390                 395                 400
Ser Ser Gly Ala Leu Val Asp Met Val Ser Lys Gly Glu Glu Leu Phe
                405                 410                 415
Thr Gly Val Val Pro Ile Leu Val Glu Leu Asp Gly Asp Val Asn Gly
            420                 425                 430
His Lys Phe Ser Val Ser Gly Glu Gly Glu Gly Asp Ala Thr Tyr Gly
            435                 440                 445
Lys Leu Thr Leu Lys Phe Ile Cys Thr Thr Gly Lys Leu Pro Val Pro
    450                 455                 460
Trp Pro Thr Leu Val Thr Thr Phe Gly Tyr Gly Val Gln Cys Phe Ala
465                 470                 475                 480
Arg Tyr Pro Asp His Met Lys Gln His Asp Phe Phe Lys Ser Ala Met
                485                 490                 495
Pro Glu Gly Tyr Val Gln Glu Arg Thr Ile Phe Phe Lys Asp Asp Gly
                500                 505                 510
Asn Tyr Lys Thr Arg Ala Glu Val Lys Phe Glu Gly Asp Thr Leu Val
            515                 520                 525
Asn Arg Ile Glu Leu Lys Gly Ile Asp Phe Lys Glu Asp Gly Asn Ile
530                 535                 540
Leu Gly His Lys Leu Glu Tyr Asn Tyr Asn Ser His Asn Val Tyr Ile
545                 550                 555                 560
Met Ala Asp Lys Gln Lys Asn Gly Ile Lys Val Asn Phe Lys Ile Arg
                565                 570                 575
His Asn Ile Glu Asp Gly Ser Val Gln Leu Ala Asp His Tyr Gln Gln
                580                 585                 590
Asn Thr Pro Ile Gly Asp Gly Pro Val Leu Leu Pro Asp Asn His Tyr
            595                 600                 605
Leu Ser Tyr Gln Ser Ala Leu Ser Lys Asp Pro Asn Glu Lys Arg Asp
    610                 615                 620
His Met Val Leu Leu Glu Phe Val Thr Ala Ala Gly Ile Thr Leu Gly
```

Met Asp Glu Leu Tyr Lys
            645

<210> SEQ ID NO 64
<211> LENGTH: 1941
<212> TYPE: DNA
<213> ORGANISM: artificial sequence
<220> FEATURE:
<223> OTHER INFORMATION: synthetic polynucleotide encoding protein
      cameleon biosensor delta1-delta2-delta3

<400> SEQUENCE: 64

| | |
|---|---|
| tccatggtga gcaagggcga ggagctgttc accggggtgg tgcccatcct ggtcgagctg | 60 |
| gacggcgacg taaacggcca caggttcagc gtgtccggcg agggcgaggg cgatgccacc | 120 |
| tacggcaagc tgaccctgaa gttcatctgc accaccggca agctgcccgt gccctggccc | 180 |
| accctcgtga ccaccctgac ctggggcgtg cagtgcttca gccgctaccc cgaccacatg | 240 |
| aagcagcacg acttcttcaa gtccgccatg cccgaaggct acgtccagga cgtaccatc | 300 |
| ttcttcaagg acgacggcaa ctacaagacc cgcgccgagg tgaagttcga gggcgacacc | 360 |
| ctggtgaacc gcatcgagct gaagggcatc gacttcaagg aggacggcaa catcctgggg | 420 |
| cacaagctgg agtacaacta catcagccac aacgtctata tcaccgccga caagcagaag | 480 |
| aacggcatca aggcccactt caagatccgc cacaacatcg aggacggcag cgtgcagctc | 540 |
| gccgaccact accagcagaa caccccatc ggcgacggcc ccgtgctgct gcccgacaac | 600 |
| cactacctga gcacccagtc cgccctgagc aagaccccca cgagaagcg cgatcacatg | 660 |
| gtcctgctgg agttcgtgac cgccgccgag ctcatggcgg atcagttgac cgacgatcag | 720 |
| atctctgaat ttaaggaagc cttcagctta ttcgacggtg atggttgcat taccaccaag | 780 |
| gaactgggta ctgtgatgcg ttccctgggc caaaacccga ccgaagcaga gctgcaagac | 840 |
| atgatcaacg aagtggatgg taacggtacc attgatttcc cggaattctt gaacctgatg | 900 |
| gcccgtaaga tgaaagacac cgacagcgag gaagagctga agaagccttt ccgcgttttc | 960 |
| gaccagaacg gtttcatcag cgcagcggaa ctgcgccatg tgatgaccaa cctgggcgaa | 1020 |
| aaactgacgg atgaagaagt tgatgagatg atcaaagaag cggatgtgga tggtgatggt | 1080 |
| cagattaact acgaagagtt tgttaaggtg atgatggcga aaggcggtgg cggtagcaaa | 1140 |
| cgtcgctgga aaaaaacttt tattgcggtg agcgcggcca accgctttaa aaaaattagc | 1200 |
| tcgagcggcg cgctggtcga catggtgagc aagggcgagg agctgttcac cggggtggtg | 1260 |
| cccatcctgg tcgagctgga cggcgacgta aacggccaca gttcagcgt gtccggcgag | 1320 |
| ggcgagggcg atgccaccta cggcaagctg accctgaagt tcatctgcac caccggcaag | 1380 |
| ctgcccgtgc cctggcccac cctcgtgacc accttcggct acggcgtgca gtgcttcgcc | 1440 |
| cgctaccccg accacatgaa gcagcacgac ttcttcaagt ccgccatgcc cgaaggctac | 1500 |
| gtccaggagc gcaccatctt cttcaaggac gacggcaact acaagacccg cgccgaggtg | 1560 |
| aagttcgagg gcgacaccct ggtgaaccgc atcgagctga agggcatcga cttcaaggag | 1620 |
| gacggcaaca tcctgggca agctggagta caactacaca gccacaacgt ctatatc | 1680 |
| atggccgaca agcagaagaa cggcatcaag gtgaacttca gatccgcca caacatcgag | 1740 |
| gacggcagcg tgcagctcgc cgaccactac cagcagaaca ccccatcgg cgacggcccc | 1800 |
| gtgctgctgc ccgacaacca ctacctgagc taccagtccg ccctgagcaa agaccccaac | 1860 |
| gagaagcgcg atcacatggt cctgctggag ttcgtgaccg ccgccgggat cactctcggc | 1920 | atggacgagc tgtacaagta a 1941

<210> SEQ ID NO 65
<211> LENGTH: 550
<212> TYPE: PRT
<213> ORGANISM: artificial sequence
<220> FEATURE:
<223> OTHER INFORMATION: synthetic protein cameleon biosensor N-ter

<400> SEQUENCE: 65

| Ser | Met | Val | Ser | Lys | Gly | Glu | Glu | Leu | Phe | Thr | Gly | Val | Val | Pro | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Val | Glu | Leu | Asp | Gly | Asp | Val | Asn | Gly | His | Arg | Phe | Ser | Val | Ser |
|     |     |     | 20  |     |     |     |     | 25  |     |     |     |     | 30  |     |     |

| Gly | Glu | Gly | Glu | Gly | Asp | Ala | Thr | Tyr | Gly | Lys | Leu | Thr | Leu | Lys | Phe |
|     |     |     | 35  |     |     |     |     | 40  |     |     |     |     | 45  |     |     |

| Ile | Cys | Thr | Thr | Gly | Lys | Leu | Pro | Val | Pro | Trp | Pro | Thr | Leu | Val | Thr |
|     | 50  |     |     |     |     | 55  |     |     |     |     | 60  |     |     |     |     |

| Thr | Leu | Thr | Trp | Gly | Val | Gln | Cys | Phe | Ser | Arg | Tyr | Pro | Asp | His | Met |
| 65  |     |     |     |     | 70  |     |     |     |     | 75  |     |     |     |     | 80  |

| Lys | Gln | His | Asp | Phe | Phe | Lys | Ser | Ala | Met | Pro | Glu | Gly | Tyr | Val | Gln |
|     |     |     |     | 85  |     |     |     |     | 90  |     |     |     |     | 95  |     |

| Glu | Arg | Thr | Ile | Phe | Phe | Lys | Asp | Asp | Gly | Asn | Tyr | Lys | Thr | Arg | Ala |
|     |     |     | 100 |     |     |     |     | 105 |     |     |     |     | 110 |     |     |

| Glu | Val | Lys | Phe | Glu | Gly | Asp | Thr | Leu | Val | Asn | Arg | Ile | Glu | Leu | Lys |
|     |     |     | 115 |     |     |     |     | 120 |     |     |     |     | 125 |     |     |

| Gly | Ile | Asp | Phe | Lys | Glu | Asp | Gly | Asn | Ile | Leu | Gly | His | Lys | Leu | Glu |
|     |     |     | 130 |     |     |     |     | 135 |     |     |     |     | 140 |     |     |

| Tyr | Asn | Tyr | Ile | Ser | His | Asn | Val | Tyr | Ile | Thr | Ala | Asp | Lys | Gln | Lys |
| 145 |     |     |     |     | 150 |     |     |     |     | 155 |     |     |     |     | 160 |

| Asn | Gly | Ile | Lys | Ala | His | Phe | Lys | Ile | Arg | His | Asn | Ile | Glu | Asp | Gly |
|     |     |     |     | 165 |     |     |     |     | 170 |     |     |     |     | 175 |     |

| Ser | Val | Gln | Leu | Ala | Asp | His | Tyr | Gln | Gln | Asn | Thr | Pro | Ile | Gly | Asp |
|     |     |     | 180 |     |     |     |     | 185 |     |     |     |     | 190 |     |     |

| Gly | Pro | Val | Leu | Leu | Pro | Asp | Asn | His | Tyr | Leu | Ser | Thr | Gln | Ser | Ala |
|     |     |     | 195 |     |     |     |     | 200 |     |     |     |     | 205 |     |     |

| Leu | Ser | Lys | Asp | Pro | Asn | Glu | Lys | Arg | Asp | His | Met | Val | Leu | Leu | Glu |
|     |     |     | 210 |     |     |     |     | 215 |     |     |     |     | 220 |     |     |

| Phe | Val | Thr | Ala | Ala | Glu | Leu | Pro | Met | Ala | Asp | Gln | Leu | Thr | Asp | Asp |
| 225 |     |     |     |     | 230 |     |     |     |     | 235 |     |     |     |     | 240 |

| Gln | Ile | Ser | Glu | Phe | Lys | Glu | Ala | Phe | Ser | Leu | Phe | Asp | Lys | Asp | Gly |
|     |     |     |     | 245 |     |     |     |     | 250 |     |     |     |     | 255 |     |

| Asp | Gly | Cys | Ile | Thr | Thr | Lys | Glu | Leu | Gly | Thr | Val | Met | Arg | Ser | Leu |
|     |     |     | 260 |     |     |     |     | 265 |     |     |     |     | 270 |     |     |

| Gly | Gln | Asn | Pro | Thr | Glu | Ala | Glu | Leu | Gln | Asp | Met | Ile | Asn | Glu | Val |
|     |     |     | 275 |     |     |     |     | 280 |     |     |     |     | 285 |     |     |

| Asp | Ala | Asp | Gly | Asn | Gly | Thr | Ile | Asp | Phe | Pro | Glu | Phe | Leu | Asn | Leu |
|     |     |     | 290 |     |     |     |     | 295 |     |     |     |     | 300 |     |     |

| Met | Ala | Arg | Lys | Pro | Val | Asp | Met | Val | Ser | Lys | Gly | Glu | Glu | Leu | Phe |
| 305 |     |     |     |     | 310 |     |     |     |     | 315 |     |     |     |     | 320 |

| Thr | Gly | Val | Val | Pro | Ile | Leu | Val | Glu | Leu | Asp | Gly | Asp | Val | Asn | Gly |
|     |     |     |     | 325 |     |     |     |     | 330 |     |     |     |     | 335 |     |

| His | Lys | Phe | Ser | Val | Ser | Gly | Glu | Gly | Glu | Gly | Asp | Ala | Thr | Tyr | Gly |
|     |     |     |     | 340 |     |     |     |     | 345 |     |     |     |     | 350 |     |

```
Lys Leu Thr Leu Lys Phe Ile Cys Thr Thr Gly Lys Leu Pro Val Pro
            355                 360                 365

Trp Pro Thr Leu Val Thr Thr Phe Gly Tyr Gly Val Gln Cys Phe Ala
        370                 375                 380

Arg Tyr Pro Asp His Met Lys Gln His Asp Phe Phe Lys Ser Ala Met
385                 390                 395                 400

Pro Glu Gly Tyr Val Gln Glu Arg Thr Ile Phe Phe Lys Asp Asp Gly
                405                 410                 415

Asn Tyr Lys Thr Arg Ala Glu Val Lys Phe Glu Gly Asp Thr Leu Val
            420                 425                 430

Asn Arg Ile Glu Leu Lys Gly Ile Asp Phe Lys Glu Asp Gly Asn Ile
        435                 440                 445

Leu Gly His Lys Leu Glu Tyr Asn Tyr Asn Ser His Asn Val Tyr Ile
    450                 455                 460

Met Ala Asp Lys Gln Lys Asn Gly Ile Lys Val Asn Phe Lys Ile Arg
465                 470                 475                 480

His Asn Ile Glu Asp Gly Ser Val Gln Leu Ala Asp His Tyr Gln Gln
                485                 490                 495

Asn Thr Pro Ile Gly Asp Gly Pro Val Leu Leu Pro Asp Asn His Tyr
            500                 505                 510

Leu Ser Tyr Gln Ser Ala Leu Ser Lys Asp Pro Asn Glu Lys Arg Asp
        515                 520                 525

His Met Val Leu Leu Glu Phe Val Thr Ala Ala Gly Ile Thr Leu Gly
    530                 535                 540

Met Asp Glu Leu Tyr Lys
545                 550

<210> SEQ ID NO 66
<211> LENGTH: 1653
<212> TYPE: DNA
<213> ORGANISM: artificial sequence
<220> FEATURE:
<223> OTHER INFORMATION: synthetic polynucleotide encoding protein
      cameleon biosensor N-ter

<400> SEQUENCE: 66
tccatggtga gcaagggcga ggagctgttc accggggtgg tgcccatcct ggtcgagctg     60
gacggcgacg taaacggcca caggttcagc gtgtccggcg agggcgaggg cgatgccacc    120
tacggcaagc tgaccctgaa gttcatctgc accaccggca agctgcccgt gccctggccc    180
accctcgtga ccaccctgac ctggggcgtg cagtgcttca gccgctaccc cgaccacatg    240
aagcagcacg acttcttcaa gtccgccatg cccgaaggct acgtccagga gcgtaccatc    300
ttcttcaagg acgacggcaa ctacaagacc cgcgccgagg tgaagttcga gggcgacacc    360
ctggtgaacc gcatcgagct gaagggcatc gacttcaagg aggacggcaa catcctgggg    420
cacaagctgg agtacaacta catcagccac aacgtctata tcaccgccga caagcagaag    480
aacggcatca aggcccactt caagatccgc cacaacatcg aggacggcag cgtgcagctc    540
gccgaccact accagcagaa cacccccatc ggcgacggcc ccgtgctgct gcccgacaac    600
cactacctga gcacccagtc cgccctgagc aaagacccca acgagaagcg cgatcacatg    660
gtcctgctgg agttcgtgac cgccgccgag ctcccgatgg cggatcagtt gaccgacgat    720
cagatctctg aatttaagga agccttcagc ttattcgaca aggatggtga tggttgcatt    780
accaccaagg aactgggtac tgtgatgcgt tccctgggcc aaaacccgac cgaagcagag    840
ctgcaagaca tgatcaacga agtggatgcg gatggtaacg gtaccattga tttcccggaa    900
```

```
ttcttgaacc tgatggcccg taagccggtc gacatggtga gcaagggcga ggagctgttc    960
accggggtgg tgcccatcct ggtcgagctg acggcgacg taaacggcca caagttcagc   1020
gtgtccggcg agggcgaggg cgatgccacc tacggcaagc tgaccctgaa gttcatctgc   1080
accaccggca agctgcccgt gccctggccc accctcgtga ccaccttcgg ctacggcgtg   1140
cagtgcttcg cccgctaccc cgaccacatg aagcagcacg acttcttcaa gtccgccatg   1200
cccgaaggct acgtccagga gcgcaccatc ttcttcaagg acgacggcaa ctacaagacc   1260
cgcgccgagg tgaagttcga gggcgacacc ctggtgaacc gcatcgagct gaagggcatc   1320
gacttcaagg aggacggcaa catcctgggg cacaagctgg agtacaacta caacagccac   1380
aacgtctata tcatggccga caagcagaag aacggcatca aggtgaactt caagatccgc   1440
cacaacatcg aggacggcag cgtgcagctc gccgaccact accagcagaa cacccccatc   1500
ggcgacggcc ccgtgctgct gcccgacaac cactacctga gctaccagtc cgccctgagc   1560
aaagacccca acgagaagcg cgatcacatg gtcctgctgg agttcgtgac cgccgccggg   1620
atcactctcg gcatggacga gctgtacaag taa                               1653
```

<210> SEQ ID NO 67
<211> LENGTH: 648
<212> TYPE: PRT
<213> ORGANISM: artificial sequence
<220> FEATURE:
<223> OTHER INFORMATION: synthetic protein Cameleon biosensor
      delta1-delta2

<400> SEQUENCE: 67

```
Ser Met Val Ser Lys Gly Glu Glu Leu Phe Thr Gly Val Val Pro Ile
1               5                   10                  15

Leu Val Glu Leu Asp Gly Asp Val Asn Gly His Arg Phe Ser Val Ser
            20                  25                  30

Gly Glu Gly Glu Gly Asp Ala Thr Tyr Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Trp Gly Val Gln Cys Phe Ser Arg Tyr Pro Asp His Met
65                  70                  75                  80

Lys Gln His Asp Phe Phe Lys Ser Ala Met Pro Glu Gly Tyr Val Gln
                85                  90                  95

Glu Arg Thr Ile Phe Phe Lys Asp Asp Gly Asn Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Tyr Ile Ser His Asn Val Tyr Ile Thr Ala Asp Lys Gln Lys
145                 150                 155                 160

Asn Gly Ile Lys Ala His Phe Lys Ile Arg His Asn Ile Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asn His Tyr Leu Ser Thr Gln Ser Ala
        195                 200                 205

Leu Ser Lys Asp Pro Asn Glu Lys Arg Asp His Met Val Leu Leu Glu
    210                 215                 220
```

```
Phe Val Thr Ala Ala Glu Leu Met Ala Asp Gln Leu Thr Asp Gln
225                 230                 235                 240

Ile Ser Glu Phe Lys Glu Ala Phe Ser Leu Phe Asp Gly Asp Gly Cys
            245                 250                 255

Ile Thr Thr Lys Glu Leu Gly Thr Val Met Arg Ser Leu Gly Gln Asn
            260                 265                 270

Pro Thr Glu Ala Glu Leu Gln Asp Met Ile Asn Glu Val Asp Gly Asn
            275                 280                 285

Gly Thr Ile Asp Phe Pro Glu Phe Leu Asn Leu Met Ala Arg Lys Met
            290                 295                 300

Lys Asp Thr Asp Ser Glu Glu Leu Lys Glu Ala Phe Arg Val Phe
305                 310                 315                 320

Asp Lys Asp Gln Asn Gly Phe Ile Ser Ala Ala Glu Leu Arg His Val
                325                 330                 335

Met Thr Asn Leu Gly Glu Lys Leu Thr Asp Glu Glu Val Asp Glu Met
            340                 345                 350

Ile Lys Glu Ala Asp Val Asp Gly Asp Gly Gln Ile Asn Tyr Glu Glu
            355                 360                 365

Phe Val Lys Val Met Met Ala Lys Gly Gly Gly Ser Lys Arg Arg
370                 375                 380

Trp Lys Lys Asn Phe Ile Ala Val Ser Ala Ala Asn Arg Phe Lys Lys
385                 390                 395                 400

Ile Ser Ser Ser Gly Ala Leu Val Asp Met Val Ser Lys Gly Glu Glu
                405                 410                 415

Leu Phe Thr Gly Val Val Pro Ile Leu Val Glu Leu Asp Gly Asp Val
            420                 425                 430

Asn Gly His Lys Phe Ser Val Ser Gly Glu Gly Glu Gly Asp Ala Thr
            435                 440                 445

Tyr Gly Lys Leu Thr Leu Lys Phe Ile Cys Thr Thr Gly Lys Leu Pro
450                 455                 460

Val Pro Trp Pro Thr Leu Val Thr Thr Phe Gly Tyr Gly Val Gln Cys
465                 470                 475                 480

Phe Ala Arg Tyr Pro Asp His Met Lys Gln His Asp Phe Phe Lys Ser
                485                 490                 495

Ala Met Pro Glu Gly Tyr Val Gln Glu Arg Thr Ile Phe Phe Lys Asp
            500                 505                 510

Asp Gly Asn Tyr Lys Thr Arg Ala Glu Val Lys Phe Glu Gly Asp Thr
            515                 520                 525

Leu Val Asn Arg Ile Glu Leu Lys Gly Ile Asp Phe Lys Glu Asp Gly
            530                 535                 540

Asn Ile Leu Gly His Lys Leu Glu Tyr Asn Tyr Asn Ser His Asn Val
545                 550                 555                 560

Tyr Ile Met Ala Asp Lys Gln Lys Asn Gly Ile Lys Val Asn Phe Lys
                565                 570                 575

Ile Arg His Asn Ile Glu Asp Gly Ser Val Gln Leu Ala Asp His Tyr
            580                 585                 590

Gln Gln Asn Thr Pro Ile Gly Asp Gly Pro Val Leu Leu Pro Asp Asn
            595                 600                 605

His Tyr Leu Ser Tyr Gln Ser Ala Leu Ser Lys Asp Pro Asn Glu Lys
            610                 615                 620

Arg Asp His Met Val Leu Leu Glu Phe Val Thr Ala Ala Gly Ile Thr
625                 630                 635                 640
```

Leu Gly Met Asp Glu Leu Tyr Lys
              645

<210> SEQ ID NO 68
<211> LENGTH: 1947
<212> TYPE: DNA
<213> ORGANISM: artificial sequence
<220> FEATURE:
<223> OTHER INFORMATION: synthetic polynucleotide encoding cameleon
     biosensor delta1-delta2

<400> SEQUENCE: 68

```
tccatggtga gcaagggcga ggagctgttc accggggtgg tgcccatcct ggtcgagctg      60
gacggcgacg taaacggcca caggttcagc gtgtccggcg agggcgaggg cgatgccacc     120
tacggcaagc tgaccctgaa gttcatctgc accaccggca agctgcccgt gccctggccc     180
accctcgtga ccaccctgac ctggggcgtg cagtgcttca gccgctaccc cgaccacatg     240
aagcagcacg acttcttcaa gtccgccatg cccgaaggct acgtccagga gcgtaccatc     300
ttcttcaagg acgacggcaa ctacaagacc cgcgccgagg tgaagttcga gggcgacacc     360
ctggtgaacc gcatcgagct gaagggcatc gacttcaagg aggacggcaa catcctgggg     420
cacaagctgg agtacaacta catcagccac aacgtctata tcaccgccga caagcagaag     480
aacggcatca aggcccactt caagatccgc cacaacatcg aggacggcag cgtgcagctc     540
gccgaccact accagcagaa cacccccatc ggcgacggcc ccgtgctgct gcccgacaac     600
cactacctga gcacccagtc cgccctgagc aaagacccca cgagaagcg cgatcacatg     660
gtcctgctgg agttcgtgac cgccgccgag ctcatggcgg atcagttgac cgacgatcag     720
atctctgaat taaggaagc cttcagctta ttcgacggtg atggttgcat taccaccaag     780
gaactgggta ctgtgatgcg ttccctgggc aaaaacccga ccgaagcaga gctgcaagac     840
atgatcaacg aagtggatgg taacggtacc attgatttcc cggaattctt gaacctgatg     900
gcccgtaaga tgaaagacac cgacagcgag gaagagctga agaagccctt ccgcgttttc     960
gacaaagacc agaacggttt catcagcgca gcggaactgc gccatgtgat gaccaacctg    1020
ggcgaaaaac tgacggatga agaagttgat gagatgatca agaagcgga tgtggatggt    1080
gatggtcaga ttaactacga agagtttgtt aaggtgatga tggcgaaagg cggtggcggt    1140
agcaaacgtc gctggaaaaa aaactttatt gcggtgagcg cggccaaccg ctttaaaaaa    1200
attagctcga gcggcgcgct ggtcgacatg gtgagcaagg gcgaggagct gttcaccggg    1260
gtggtgccca tcctggtcga gctggacggc gacgtaaacg gccacaagtt cagcgtgtcc    1320
ggcgagggcg agggcgatgc cacctacggc aagctgaccc tgaagttcat ctgcaccacc    1380
ggcaagctgc ccgtgcccctg gcccaccctc gtgaccacct cggctacgg cgtgcagtgc    1440
ttcgcccgct accccgacca catgaagcag cacgacttct tcaagtccgc catgcccgaa    1500
ggctacgtcc aggagcgcac catcttcttc aaggacgacg gcaactacaa gacccgcgcc    1560
gaggtgaagt tcgagggcga caccctggtg aaccgcatcg agctgaaggg catcgacttc    1620
aaggaggacg gcaacatcct ggggcacaag ctggagtaca actacaacag ccacaacgtc    1680
tatatcatgg ccgacaagca gaagaacggc atcaaggtga acttcaagat ccgccacaac    1740
atcgaggacg gcagcgtgca gctcgccgac cactaccagc agaacacccc catcggcgac    1800
ggccccgtgc tgctgcccga caaccactac ctgagctacc agtccgccct gagcaaagac    1860
cccaacgaga gcgcgatca catggtcctg ctggagttcg tgaccgccgc cgggatcact    1920
ctcggcatgg acgagctgta caagtaa                                        1947
```

<210> SEQ ID NO 69
<211> LENGTH: 12
<212> TYPE: PRT
<213> ORGANISM: artificial sequence
<220> FEATURE:
<223> OTHER INFORMATION: synthetic peptide EF-hand1 loop +C7Y+T10A+K11A

<400> SEQUENCE: 69

Asp Lys Asp Gly Asp Gly Tyr Ile Thr Ala Ala Glu
1               5                   10

<210> SEQ ID NO 70
<211> LENGTH: 10
<212> TYPE: PRT
<213> ORGANISM: artificial sequence
<220> FEATURE:
<223> OTHER INFORMATION: synthetic peptide EF-hand1 loop deltaD1T10

<400> SEQUENCE: 70

Lys Asp Gly Asp Gly Cys Ile Thr Lys Glu
1               5                   10

<210> SEQ ID NO 71
<211> LENGTH: 10
<212> TYPE: PRT
<213> ORGANISM: artificial sequence
<220> FEATURE:
<223> OTHER INFORMATION: synthetic peptide EF-hand1 loop deltaD1K11

<400> SEQUENCE: 71

Lys Asp Gly Asp Gly Cys Ile Thr Thr Glu
1               5                   10

<210> SEQ ID NO 72
<211> LENGTH: 10
<212> TYPE: PRT
<213> ORGANISM: artificial sequence
<220> FEATURE:
<223> OTHER INFORMATION: synthetic peptide EF-hand1 loop deltaD3T10

<400> SEQUENCE: 72

Asp Lys Gly Asp Gly Cys Ile Thr Lys Glu
1               5                   10

<210> SEQ ID NO 73
<211> LENGTH: 10
<212> TYPE: PRT
<213> ORGANISM: artificial sequence
<220> FEATURE:
<223> OTHER INFORMATION: synthetic peptide EF-hand1 loop delta D3K11

<400> SEQUENCE: 73

Asp Lys Gly Asp Gly Cys Ile Thr Thr Glu
1               5                   10

<210> SEQ ID NO 74
<211> LENGTH: 9
<212> TYPE: PRT
<213> ORGANISM: artificial sequence
<220> FEATURE:
<223> OTHER INFORMATION: synthetic peptide EF-hand1 loop delta D1T10K11

<400> SEQUENCE: 74

Lys Asp Gly Asp Gly Cys Ile Thr Glu
1               5

<210> SEQ ID NO 75
<211> LENGTH: 9
<212> TYPE: PRT
<213> ORGANISM: artificial sequence
<220> FEATURE:
<223> OTHER INFORMATION: synthetic peptide EF-hand1 loop delta D3T10K11

<400> SEQUENCE: 75

Asp Lys Gly Asp Gly Cys Ile Thr Glu
1               5

<210> SEQ ID NO 76
<211> LENGTH: 10
<212> TYPE: PRT
<213> ORGANISM: artificial sequence
<220> FEATURE:
<223> OTHER INFORMATION: synthetic peptide EF-hand2 loop delta-D1F10

<400> SEQUENCE: 76

Ala Asp Gly Asn Gly Thr Ile Asp Pro Glu
1               5                   10

<210> SEQ ID NO 77
<211> LENGTH: 10
<212> TYPE: PRT
<213> ORGANISM: artificial sequence
<220> FEATURE:
<223> OTHER INFORMATION: synthetic peptide EF-hand2 loop deltaD1P11

<400> SEQUENCE: 77

Ala Asp Gly Asn Gly Thr Ile Asp Phe Glu
1               5                   10

<210> SEQ ID NO 78
<211> LENGTH: 10
<212> TYPE: PRT
<213> ORGANISM: artificial sequence
<220> FEATURE:
<223> OTHER INFORMATION: synthetic peptide EF-hand2 loop delta D3F10

<400> SEQUENCE: 78

Asp Ala Gly Asn Gly Thr Ile Asp Pro Glu
1               5                   10

<210> SEQ ID NO 79
<211> LENGTH: 10
<212> TYPE: PRT
<213> ORGANISM: artificial sequence
<220> FEATURE:
<223> OTHER INFORMATION: synthetic peptide EF-hand2 loop delta D3P11

<400> SEQUENCE: 79

Asp Ala Gly Asn Gly Thr Ile Asp Phe Glu
1               5                   10

<210> SEQ ID NO 80
<211> LENGTH: 9
<212> TYPE: PRT
<213> ORGANISM: artificial sequence
<220> FEATURE:
<223> OTHER INFORMATION: synthetic peptide EF-hand2 loop delta D1F10P11

<400> SEQUENCE: 80

Ala Asp Gly Asn Gly Thr Ile Asp Glu
1               5

```
<210> SEQ ID NO 81
<211> LENGTH: 9
<212> TYPE: PRT
<213> ORGANISM: artificial sequence
<220> FEATURE:
<223> OTHER INFORMATION: synthetic peptide EF-hand2 loop delta D3F10P11

<400> SEQUENCE: 81

Asp Ala Gly Asn Gly Thr Ile Asp Glu
1               5

<210> SEQ ID NO 82
<211> LENGTH: 10
<212> TYPE: PRT
<213> ORGANISM: artificial sequence
<220> FEATURE:
<223> OTHER INFORMATION: synthetic peptide EF-hand3 loop delta D1A10

<400> SEQUENCE: 82

Lys Asp Gln Asn Gly Phe Ile Ser Ala Glu
1               5                   10

<210> SEQ ID NO 83
<211> LENGTH: 10
<212> TYPE: PRT
<213> ORGANISM: artificial sequence
<220> FEATURE:
<223> OTHER INFORMATION: synthetic peptide EF-hand3 loop delta D1A11

<400> SEQUENCE: 83

Lys Asp Gln Asn Gly Phe Ile Ser Ala Glu
1               5                   10

<210> SEQ ID NO 84
<211> LENGTH: 10
<212> TYPE: PRT
<213> ORGANISM: artificial sequence
<220> FEATURE:
<223> OTHER INFORMATION: synthetic peptide EF-hand3 loop delta D3A10

<400> SEQUENCE: 84

Asp Lys Gln Asn Gly Phe Ile Ser Ala Glu
1               5                   10

<210> SEQ ID NO 85
<211> LENGTH: 10
<212> TYPE: PRT
<213> ORGANISM: artificial sequence
<220> FEATURE:
<223> OTHER INFORMATION: synthetic peptide EF-hand3 loop delta D3A11

<400> SEQUENCE: 85

Asp Lys Gln Asn Gly Phe Ile Ser Ala Glu
1               5                   10

<210> SEQ ID NO 86
<211> LENGTH: 9
<212> TYPE: PRT
<213> ORGANISM: artificial sequence
<220> FEATURE:
<223> OTHER INFORMATION: synthetic peptide EF-hand3 loop delta D1A10A11

<400> SEQUENCE: 86

Lys Asp Gln Asn Gly Phe Ile Ser Glu
1               5

<210> SEQ ID NO 87
```

```
<211> LENGTH: 9
<212> TYPE: PRT
<213> ORGANISM: artificial sequence
<220> FEATURE:
<223> OTHER INFORMATION: synthetic peptide EF-hand3 loop delta D3A10A11

<400> SEQUENCE: 87

Asp Lys Gln Asn Gly Phe Ile Ser Glu
1               5

<210> SEQ ID NO 88
<211> LENGTH: 10
<212> TYPE: PRT
<213> ORGANISM: artificial sequence
<220> FEATURE:
<223> OTHER INFORMATION: synthetic peptide EF-hand4 loop delta D1Y10

<400> SEQUENCE: 88

Val Asp Gly Asp Gly Gln Ile Asn Glu Glu
1               5                   10

<210> SEQ ID NO 89
<211> LENGTH: 10
<212> TYPE: PRT
<213> ORGANISM: artificial sequence
<220> FEATURE:
<223> OTHER INFORMATION: synthetic peptide EF-hand4 loop delta D1E11

<400> SEQUENCE: 89

Val Asp Gly Asp Gly Gln Ile Asn Tyr Glu
1               5                   10

<210> SEQ ID NO 90
<211> LENGTH: 10
<212> TYPE: PRT
<213> ORGANISM: artificial sequence
<220> FEATURE:
<223> OTHER INFORMATION: synthetic peptide EF-hand4 loop delta D3Y10

<400> SEQUENCE: 90

Asp Val Gly Asp Gly Gln Ile Asn Glu Glu
1               5                   10

<210> SEQ ID NO 91
<211> LENGTH: 10
<212> TYPE: PRT
<213> ORGANISM: artificial sequence
<220> FEATURE:
<223> OTHER INFORMATION: synthetic peptide EF-hand4 loop delta D3E11

<400> SEQUENCE: 91

Asp Val Gly Asp Gly Gln Ile Asn Tyr Glu
1               5                   10

<210> SEQ ID NO 92
<211> LENGTH: 9
<212> TYPE: PRT
<213> ORGANISM: artificial sequence
<220> FEATURE:
<223> OTHER INFORMATION: synthetic peptide EF-hand4 loop delta D1Y10E11

<400> SEQUENCE: 92

Val Asp Gly Asp Gly Gln Ile Asn Glu
1               5

<210> SEQ ID NO 93
<211> LENGTH: 9
```

```
<212> TYPE: PRT
<213> ORGANISM: artificial sequence
<220> FEATURE:
<223> OTHER INFORMATION: synthetic peptide EF-hand4 loop delta D3Y10E11

<400> SEQUENCE: 93

Asp Val Gly Asp Gly Gln Ile Asn Glu
1               5
```

URANIUM-CHELATING PEPTIDES DERIVED FROM EF-HAND CALCIUM-BINDING MOTIF USEFUL FOR URANIUM BIODETECTION AND BIODECONTAMINATION

SEQUENCE LISTING SUBMISSION VIA EFS WEB

A computer readable text file, entitled "045636-5285_SequenceListing.txt," created on or about Jan. 19, 2016 with a file size of about 97 KB contains the sequence listing for this application and is hereby incorporated by reference in its entirety.

The present relates to new uranium-chelating peptides derived from EF-hand calcium-binding motif, useful for uranium biodetection and biodecontamination.

Uranium is a radioactive heavy metal, which is naturally present in varying concentrations in the environment. However, the wide use of uranium for industrial and military applications increases the risk of its distribution in the environment, which is aggravated by such factors as mining activities, uranium processing, or leaching of radioactive wastes.

Uranium presents radiological and chemical toxicity to living organisms. The linear dioxo uranyl form ($UO_2^{2+}$) which corresponds to uranium in its hexavalent oxidation state U(VI) is the prevalent form of uranium in the presence of oxygen and the most stable chemical form of uranium in water. It is soluble, bioavailable, and thus potentially toxic.

Therefore, it is of high interest to develop systems allowing uranyl detection in the environment as well as molecules allowing its complexation in various environments with high affinity and selectivity. In particular, sensitive and easy to use systems allowing the detection of uranyl content in waters at the concentration levels defined by World Health Organization (WHO)(inferior to 0.03 mg/L, i.e. 126 nM; Guidelines for drinking-water quality, Fourth Edition, 2011, World Health Organization, WHO Press, Geneva) would be of great help for the water level monitoring.

Among these systems, molecules derived from peptides are advantageous in that they are non toxic, and can be easily produced either synthetically or using recombinant techniques. Similarly, the development of organisms bearing uranyl biosensors, capable of detecting the uranyl fraction that is bioavailable and thus potentially toxic, is needed to assess water quality on a long term basis.

Finally, bioremediation is an emerging technique that would allow the decontamination of large areas of contaminated water and/or soils.

The helix-loop-helix calcium-binding motif (EF-hand motif) is the most prevalent $Ca^{2+}$-binding site in proteins. The canonical EF-hand motif of about 30 amino acids in length is structured by two alpha-helices bridged by a flexible metal-binding loop (also referred to as calcium-binding loop, calcium-binding site, loop or site) composed of 12 highly conserved residues, with calcium coordinating positions at 1 (+X), 3 (+Y), 5 (+Z), 7 (−Y), 9 (−X) and 12 (−Z). The residues at the ligand positions 1, 3, 5 and 12 and also at the non-ligand positions 6 and 8 are highly conserved. The calcium ion is coordinated in a pentagonal bipyramidal configuration with a coordination number of 7 to side-chain oxygen bearing groups at positions 1, 3, and 5, a water molecule hydrogen bonded to residue at position 9, and the main chain carbonyl group of residue 7. The pentagonal bipyramidal configuration arises from two additional ligands provided by a bidenate glutamic or a monodentate aspartic acid which stabilizes a water ligand, in position 12. The residue at position 1 of the loop is most frequently occupied by an aspartate (D); two residues are found at position 3: aspartic acid (D) or asparagine (N), but most frequently D; position 5 is most often occupied by aspartic acid (D), serine (S) or asparagine (N); the residue at position 7 is variable; position 9 shows a preference for residues with a side-chain oxygen (D, N, E, S, T), and the residues more frequently found at position 12 are glutamate (E) and aspartate (D), most frequently E. The highly conserved residues at the non ligand positions 6 and 8 are Gly (G) and Ile (I), respectively. The majority of the known EF-hand Calcium-Binding proteins (CaBPs) contain paired EF-hand motifs.

Functionally, the EF-hand proteins can be divided into two classes: 1) signaling proteins and 2) buffering/transport proteins. The first group is the largest and includes the most well-known members of the family such as calmodulin, troponin C and S100B. These proteins typically undergo a calcium-dependent conformational change which opens a target-binding site. The latter group is represented by calbindin D9k which remains in a closed conformation upon calcium binding.

Calmodulin (CaM) is the most studied representative of the ubiquitous EF-hand protein family and a calcium-binding protein involved in the regulation of a wide range of target enzymes. The calmodulin structure (PDB code 1EXR) includes two pairs of EF-hand motifs (EF-hands 1 and 2; EF-hands 3 and 4) in two domains (domain 1 and 2) separated by a flexible α-helix (FIG. 1A). In EF-hand1, calcium ligands are provided by three monodentate aspartate (D) at positions 1, 3, 5 of the metal-binding loop (D1, D3, D5), a bidentate glutamate at position 12 (E12), a main chain carbonyl at position 7 and a water molecule stabilized by threonine 9 (T9) side chain, as schematized in FIG. 1B.

Fluorescent sensors for calcium, called cameleons, have been constructed based on green fluorescent proteins and calmodulin (Miyawaki et al., Nature, 1997, 388, 882-887; Nagai et al., PNAS, 2004, 101, 10554-10559). They are chimeric proteins composed of a short-wavelength variant of GFP, CaM, a glycylglycine linker, the CaM-binding peptide of myosin light-chain kinase (M13), and a long-wavelength variant of GFP. $Ca^{2+}$ binding to CaM initiates an intramolecular interaction between CaM and M13, which changes the chimeric protein from an extended to a more compact conformation, thereby increasing the efficiency of Fluorescence Resonance Energy Transfer (FRET) from the shorter to the longer-wavelength variant of GFP. Yellow cameleons (YCs) have cyan and yellow fluorescent proteins (CFP and GFP) as the FRET donor and acceptor, respectively.

Synthetic cyclic-peptide variants of calmodulin site 1 (CaM-Mc peptides), consisting of a 33 amino acid sequence in which one, two or three of the aspartic acid residues in positions 1, 3 and 5 of the calcium-binding loop (D1, D3, D5) are substituted with neutral amino acids (T, N or S) and a tyrosine residue is introduced in position 7 of the loop to monitor metal binding using tyrosine fluorescence, bind uranyl with an apparent dissociation constant in the micromolar range ($K_d$ of 9.8 to $54.10^{-6}$ M) while they don't bind calcium (WO 2005/012336). However, uranyl biosensors with detection limits in the nanomolar range or below are required to detect uranium content in waters at the maximum concentration levels defined by WHO.

A recombinant phosphorylated variant of calmodulin domain 1, CaM1P, in which the threonine at position 9 of the EF-hand1 loop is phosphorylated, was shown to bind uranyl with a dissociation constant in the subnanomolar range, at pH 7 ($K_d$ of $3.10^{-10}$ M; Pardoux et al., 2012 PLoS ONE, 2012, 7, e41922). CaM1P is derived from CaM1 which consists of a 77 amino acids sequence, in which: (i) the $T_9TKE_{12}$ sequence of EF-hand1 loop is substituted by the CK2 recognition sequence TAAE to allow phosphorylation of the threonine 9, in vitro, using recombinant catalytic subunit of protein kinase CK2, (ii) a tyrosine residue is introduced in position 7 of the EF-hand 1 loop so that uranyl and calcium-binding affinities could be determined by following tyrosine fluorescence emission at 302 nm, and (iii) the metal-binding ability of site 2 is impaired by substituting the two aspartate residues in positions 1 and 3 of the loop with alanine residues.

Phosphorylation of the threonine at position 9 of the metal-binding loop increased uranyl-binding affinity by a factor of 5 at pH 6, while increasing the pH to 7 led to a further enhancement in uranyl affinity by a factor of 15.6. Analysis of the infrared modes of the phosphoryl group indicated that this group was deprotonated at pH 7 and directly involved in uranyl coordination.

However, CaM1P affinity for calcium ($\sim 20.10^{-6}$ M) is similar to that of CaM domain 1 so that its selectivity for uranyl over calcium is low ($4.10^3$ at pH 6 and $6.10^4$ at pH 7).

In addition CaM1P cannot be expressed in a recombinant cell, microorganism or plant, which is then used for the in situ biodetection or bioremediation of uranyl because the phosphorylation of the Threonine 9 is performed in vitro.

In this context, new sensitive and specific metal biosensors and/or chelators would be useful for the development of cost-effective uranium biodetection and bioremediation strategies.

The inventors have determined a structural model of the complex formed by the phosphorylated CaM1 peptide (CaM1P) with uranyl using a molecular dynamics approach. This structural model suggested that at least two residues of the calcium-binding loop are not necessary to bind uranyl in the complex: at least one of the calcium-ligating residues (aspartate at position 3 or D3) and its directly adjacent residue (Lysine at position 2 or K2; FIG. 2A). This result encouraged the inventors to produce a variant CaMΔ by the deletion of these two residues of the loop (K2 and D3) formerly to analyse the resulting properties of the phosphorylated peptide CaMΔ-P (FIGS. 1C and 2B). They also analyzed, the non phosphorylated peptide CaMΔ(FIG. 2D), which showed a very high affinity for uranyl, and a low affinity for calcium, as demonstrated in the examples of the present application (FIGS. 3 and 4). The rationale of this high affinity for uranyl on one hand and for high specificity for uranyl as compared to calcium on the other hand resides in that less ligands are necessary to complete the coordination sphere of uranyl (i.e. 5 to 6 ligands disposed in the equatorial plane) than to coordinate calcium (7 to 8 ligands, 7 ligands in site 1 of calmodulin) and in that the binding loop containing 12 residues in site 1 is too large to accommodate uranyl, i.e. to optimally dispose the uranyl ligands in an equatorial plane around the uranyl $UO_2$ axis. These latter findings were obtained from the molecular dynamics simulations on phosphorylated CaM1P peptide (FIG. 2A) but they were also observed on the non-phosphorylated peptide CaM1 (FIG. 2C). In particular, according to the structural model of the CaM1-U complex, Asp at position 1 of the loop is not a uranyl ligand and it is situated below the uranyl equatorial plane (FIG. 2C). In addition, the loop arrangement in the model structure of the CaM1-U complex is not ideal as compared to the structural model of CaMΔ(FIG. 2D), in that the distance is too long between the Asp ligand and the Glu ligand, and the structure involves a carbonyl ligand (the carbonyl group of Tyr7) that is considered as a weaker ligand as compared to the side chain of aspartate.

Therefore, the present invention concerns the optimisation of uranyl binding sites in EF-hand motifs by decreasing the size of the binding loop by two amino acids, and by suppressing at least one calcium ligand, to obtain affine and specific uranyl binding sites. As shown in the examples by the comparison of uranyl binding affinities of CaMΔ and CaMΔ3 (where only the aspartate at position 3 was deleted), two deletions are necessary to increase uranyl affinity. For the EF-hand1 of calmodulin, as demonstrated in the examples, deletion of the amino acids at positions 1 and 2 or 2 and 3 is highly efficient to increase uranyl affinity and specificity. More generally for other EF-hand motifs, the position of the deletions may depend on the sequence of these motifs. This is illustrated for site 2 by showing different possibilities to increase uranyl affinity and specificity, obtained using structure prediction by molecular dynamics simulations (FIG. 10).

One aspect of the present invention relates to a polypeptide comprising at least one helix-loop-helix calcium-binding (EF-hand) motif, which comprises a deletion of at least two amino acid residues in the 12-amino-acid calcium-binding loop sequence, and wherein said polypeptide binds uranyl.

The polypeptide of the invention which is an isolated recombinant or synthetic polypeptide, has a signicantly higher binding affinity for uranyl and a significantly lower binding affinity for calcium than the corresponding peptide without said deletion. In the present application, "significant" means that the binding affinity is different with P<0.01. Binding affinity for metals can be measured by any standard technique which is known by those skilled in the art such as those described in the examples of the present application.

Preferably, the polypeptide of the invention has a binding affinity for uranyl which is increased by a factor of at least 2, more preferably at least 5, 10, 30, 100 or more and a binding affinity for calcium which is decreased by a factor of at least 2, more preferably at least 5, 10, 30, 100, 300 or more, compared to the corresponding peptide without the deletion in the calcium-binding loop. Preferably, the polypeptide of the invention has a selectivity for uranyl over calcium which is of at least $10^3$, more preferably at least $10^4$, $10^5$, $10^6$, $10^7$ or more.

For example, the CaMΔ peptide of the example has a binding affinity for uranyl which is increased by a factor of at least 100 and a binding affinity for calcium which is decreased by a factor of at least 500 compared to the corresponding peptide CaM1 which does not have the deletion in the calcium-binding loop. Therefore the selectivity of CaMΔ for uranyl over calcium is of the order of $10^7$ whereas that of CaM1 is only of the order of $10^3$.

The polypeptide of the invention and its derivatives like the cameleon-based biosensors, have the following advantages:

they have a high binding affinity for uranyl combined with a low binding affinity for calcium, which means that they are highly sensitive and selective for uranyl. Therefore, they can detect low uranium concentration in complex media containing divalent cations like $Ca^{2+}$ (for example, biological media, calcium-rich water). Uranyl detection in a sample to analyze can be performed in vitro using the isolated polypeptide or cameleon-based biosensor, as well as in situ in recombinant cells (whole-cell biosensors) or non-human transgenic organisms expressing the cameleon protein derived from the polypeptide of the invention. Their affinity and selectivity for uranium are higher than those of all calmodulin-derived uranium biosensors.

the cameleon biosensors derived from the polypeptide of the invention can also be used as imaging biosensors to visualize uranyl in situ in recombinant cells or non-human transgenic organisms expressing the cameleon protein derived from the polypeptide of the invention, the recombinant cells and non-human transgenic organisms expressing the polypeptide or its derivatives can be used for the biodecontamination and the bioremediation of uranium contamination in an environment, as well as for the production of large quantities of the polypeptide of the invention and its derivatives (cameleon-based biosensors).

as recombinant proteins, their production and use are easy, fast not-toxic, and cost-effective, and they are designed for in vitro and in vivo uses.

In the following description, the standard one letter amino acid code is used. The expression "EF-hand motif" refers to the canonical EF-hand calcium-binding motif as described just before.

In one embodiment, the deletion includes at least one calcium-ligating residue (residue in position 1, 3, 5, 7, 9, 12 of the calcium-binding loop sequence). Preferably, the deletion includes at least one of the calcium-ligating residues in positions 1, 3, and/or 5 of the calcium-binding loop sequence, more preferably in positions 1 and/or 3. Even more preferably, the deletion includes at least the calcium-ligating residue in position 1 or 3 of the calcium-binding loop.

In an advantageous arrangement of said embodiment, the polypeptide comprises a deletion of at least one calcium-ligating residue and its directly adjacent residue (i.e., residue in position +1 or −1 relative to the calcium-ligating residue). Preferably, the polypeptide comprises a deletion of at least one of the following pairs of residues: positions 1 and 2, 2 and 3, 3 and 4, 4 and 5, 5 and 6 of the calcium-binding loop. More preferably, the polypeptide comprises a deletion of at least the pair of residues in positions 1 and 2 or 2 and 3 of the calcium-binding loop.

In another advantageous arrangement of said embodiment, the polypeptide comprises a deletion of at least one calcium-ligating residue and at least one of the residues in positions 10 and/or 11 of the calcium-binding loop. Preferably, the polypeptide comprises a deletion of at least one calcium-ligating residue in position 1 or 3 and at least one of the residues in positions 10 and/or 11 of the calcium-binding loop. More preferably, the polypeptide comprises a deletion of at least the residues chosen from positions 3 and 10 and positions 3, 10 and 11.

In another preferred embodiment, the polypeptide comprises at least two EF-hand motifs, wherein at least one EF-hand motif comprises said deletion in the loop sequence and the other EF-hand motif(s) comprise(s) said deletion in the loop sequence or not. Preferably, the polypeptide comprises two to four EF-hand motifs. More preferably, the polypeptide comprises two or four EF-hand motifs.

In another preferred embodiment, the polypeptide comprises further alterations in said EF-hand motif(s) which comprise said deletion or not, such as for example the substitution and/or the modification of one or more amino acid residues. Said alterations are introduced when the amino acid residues of interest are not naturally present at the appropriate positions in said EF-hand motif(s). Preferably, said further alterations are in the loop sequence.

In a first advantageous arrangement of said embodiment, the polypeptide comprises a fluorescent residue, preferably a tyrosine or tryptophan residue. The fluorescent residue is advantageously in the loop from said at least one EF-hand motif which comprises said deletion or not, or in close proximity to said loop. It is preferably in position 7 of said loop, by reference to the numbering of the 12-amino-acid loop sequence. Preferably, the fluorescence residue is in the loop from said at least one EF-hand motif which comprises said deletion. More preferably, the polypeptide comprises a tyrosine residue in position 7 of the loop from said at least one EF-hand motif which comprises said deletion. The fluorescent residue allows the monitoring of uranyl and/or calcium binding and the determination of their binding affinities, by following tyrosine fluorescence emission at 302 nm. The fluorescent residue is an amino acid residue naturally present in the EF-hand motif(s) or substituted.

In a second advantageous arrangement of said embodiment, the polypeptide comprises at least two aspartic acid residues in positions 1, 3 and/or 5 of the loop from said at least one EF-hand motif which comprises said deletion, by reference to the numbering of the 12-amino-acid loop sequence. The aspartic acid residues are amino acid residues naturally present in the EF-hand motif(s) or substituted.

In a third advantageous arrangement of said embodiment, the polypeptide comprises a glycine residue in position 4 of the loop from said at least one EF-hand motif which comprises said deletion or not, by reference to the numbering of the 12-amino-acid loop sequence. Preferably, the glycine residue is in the loop from said at least one EF-hand motif which comprises said deletion. The glycine residue is an amino acid residue naturally present in the EF-hand motif(s) or substituted.

In another advantageous arrangement of said embodiment, the polypeptide comprises at least one phosphorylated serine or threonine residue. The phosphorylated serine or threonine residues are advantageously in the loop from said EF-hand motif(s) which comprise said deletion or not, preferably in position 9 and/or 12 of the loop from said EF-hand motif(s), by reference to the numbering of the 12-amino-acid loop sequence. The phosphorylation of said residue(s) increases the uranyl binding affinity of the polypeptide. The residues in positions+1 to +3 relative to the phosphorylated threonine are advantageously modified to provide a CK2 recognition sequence TXXE, in which X is a neutral or acidic amino acid different from T, for example XX is AA or AE. Phosphorylation of the threonine may be performed in vitro, using recombinant catalytic subunit of protein kinase CK2. Preferably, the polypeptide comprises a phosphorylated threonine residue in position 9 of the loop from said EF-hand motif(s) which comprise(s) said deletion or not and further comprises alanine residues in positions 10 and 11 of said loop, by reference to the numbering of the 12-amino-acid loop sequence. These alanine residues provide a CK2 recognition sequence TAAE to allow phosphorylation of the Threonine 9. The phosphorylated serine or threonine residues are advantageously in the loop from said at least one EF-hand motif which comprises said deletion. The serine and threonine residues of the EF-hand motif(s) which are modified by phosphorylation and the adjacent residues which are substituted to provide a CK2 recognition site are naturally present in the EF-hand motif(s) or substituted.

In another advantageous arrangement of said embodiment, the polypeptide comprises at least two EF-hand motifs, at least one comprising said deletion in the loop sequence and at least another one not comprising said deletion, wherein at least one of said EF-hand motif(s) not comprising the deletion comprises at least one mutation in the loop sequence which impairs calcium binding. Preferably, said mutation is the substitution with alanine residues of the residues in positions 1 and 3 of the loop by reference to the numbering of the 12-amino-acid loop sequence.

The EF-hand motif sequence is modified by standard mutagenesis technique on the polypeptide coding sequence. The phosphorylation of the serine and/or threonine residues is performed using standard methods which are known from those skilled in the art.

The amino acid-sequence of the EF-hand motif(s) of the polypeptide of the invention is that of the corresponding wild-type EF-hand protein(s) except at said amino acid position(s) which are altered in the present invention.

The polypeptide of the invention may be derived from EF-hand motif(s) of any proteins of the EF-hand family (EF-hand protein) having a canonical EF-hand motif as above described. Preferably, the polypeptide of the invention is derived from EF-hand protein(s) from the class of EF-hand signaling proteins, i.e., the EF-hand proteins which undergo a calcium-dependent conformational change. More preferably, it is derived from EF-hand signaling protein(s) of the calmodulin superfamily. Even more preferably, from EF-hand signaling protein(s) of the calmodulin superfamily selected from the group consisting of calmodulin and troponin C. It is advantageously derived from EF-hand1, 2, 3 and/or 4 of calmodulin protein(s).

In an advantageous arrangement of said embodiment, the polypeptide is derived from *Arabidopsis thaliana* calmodulin 3 (amino acid sequence SEQ ID NO: 2 encoded by the cDNA of SEQ ID NO: 1).

The calmodulin EF-hand1, 2, 3 and 4 correspond respectively to positions 12 to 41, 48 to 76, 85 to 114, and 121 to 149, by reference to the amino acid numbering of *Arabidopsis thaliana* calmodulin 3 (SEQ ID NO: 2). The calcium-binding loop of EF-hand1, 2, 3 and 4 correspond respectively to positions 21 to 32, 57 to 68, 94 to 105, and 130 to 141, by reference to the amino acid numbering of SEQ ID NO: 2. The calmodulin domain 1 and 2 correspond respectively to positions 1 to 76 and 77 to 149, by reference to the amino acid numbering of SEQ ID NO: 2.

In another advantageous arrangement of said embodiment, the polypeptide comprises a EF-hand motif derived from a calmodulin EF-hand1 having a 12 amino-acid loop of sequence (I):

$X_1$-$X_2$-$X_3$-$X_4$-$X_5$-$X_6$-$X_7$-$X_8$-$X_9$-$X_1$-$X_{11}$-$X_{12}$, in which: $X_1$ is D; $X_2$ is K or R, preferably K; $X_3$ is D; $X_4$ is G, N, Q, preferably G; $X_5$ is D or N, preferably D; $X_6$ is G; $X_7$ is T, C, S or N, preferably, T; $X_8$ is I; $X_9$ is T or S, preferably T; $X_{10}$ is T or S, preferably T; $X_{11}$ is K, S, M or N, preferably K, and $X_{12}$ is E. More preferably, said EF-hand1 has a 12 amino-acid loop of sequence DKDGDGCITTKE (SEQ ID NO: 3).

In another advantageous arrangement of said embodiment, the polypeptide comprises a EF-hand motif derived from a calmodulin EF-hand2 having a 12 amino-acid loop of sequence (II):

$X_1$-$X_2$-$X_3$-$X_4$-$X_5$-$X_6$-$X_7$-$X_8$-$X_9$-$X_{10}$-$X_{11}$-$X_{12}$, in which: $X_1$ is D; $X_2$ is A, V or Q, preferably A; $X_3$ is D; $X_4$ is G, N; $X_5$ is N, D or S, preferably N; $X_6$ is G or H, preferably, G; $X_7$ is T, N or Q, preferably, T; $X_8$ is I; $X_9$ is D or E, preferably D; $X_{10}$ is F; $X_{11}$ is P, T or S, preferably P, and $X_{12}$ is E. More preferably, said EF-hand2 has a 12 amino-acid loop of sequence DADGNGTIDFPE (SEQ ID NO: 4).

In another advantageous arrangement of said embodiment, the polypeptide comprises a EF-hand motif derived from a calmodulin EF-hand3 having a 12 amino-acid loop of sequence DKDQNGFISAAE (SEQ ID NO: 5)

In another advantageous arrangement of said embodiment, the polypeptide comprises a EF-hand motif derived from a calmodulin EF-hand4 having a 12 amino-acid loop of sequence DVDGDGQINYEE (SEQ ID NO: 6).

A more preferred polypeptide of the invention is derived from calmodulin EF-hand1, EF-hand2, EF-hand3 and/or EF-hand 4 and comprises a calcium-binding loop sequence having a deletion of at least two amino acids, which is selected from the group consisting of the sequences: DGDGCITTKE (SEQ ID NO: 7), DGDGYITTKE (SEQ ID NO: 8), DGDGYITAAE (SEQ ID NO: 9), DGNGTIDFPE (SEQ ID NO: 10), DGNGYIDFPE (SEQ ID NO: 11), DGDGTIDFPE (SEQ ID NO: 12) DGDGYIDFPE (SEQ ID NO: 13), DQNGFISAAE (SEQ ID NO: 14) and DGDGQ-INYEE (SEQ ID NO: 15), KDGDGCITKE (SEQ ID NO: 70), KDGDGCITTE (SEQ ID NO: 71), DKGDGCITKE (SEQ ID NO: 72), DKGDGCITTE (SEQ ID NO: 73), KDGDGCITE (SEQ ID NO: 74), DKGDGCITE (SEQ ID NO: 75), ADGNGTIDPE (SEQ ID NO: 76), ADGNGTIDFE (SEQ ID NO: 77), DAGNGTIDPE (SEQ ID NO: 78), DAGNGTIDFE (SEQ ID NO: 79), ADGNGTIDE (SEQ ID NO: 80), DAGNGTIDE (SEQ ID NO: 81), KDQNGFISAE (SEQ ID NO: 82), KDQNGFI-SAE (SEQ ID NO: 83), DKQNGFISAE (SEQ ID NO: 84), DKQNGFISAE (SEQ ID NO: 85), KDQNGFISE (SEQ ID NO: 86), DKQNGFISE (SEQ ID NO: 87), VDGDGQINEE (SEQ ID NO: 88), VDGDGQINYE (SEQ ID NO: 89), DVGDGQINEE (SEQ ID NO: 90), DVGDGQINYE (SEQ ID NO: 91), VDGDGQINE (SEQ ID NO: 92), DVGDGQ-INE (SEQ ID NO: 93). Preferably from the group consisting of the sequences SEQ ID NO: 7 to 15, 72, 75, 78, 81, 84, 87, 90 and 93.

In another advantageous arrangement of said embodiment, the polypeptide of the invention is a calmodulin domain 1 variant comprising two EF-hand motifs, respectively from EF-hand1 and EF-hand2 of calmodulin protein(s).

A preferred calmodulin domain 1 variant polypeptide comprises a EF-hand1 comprising the deletion of the amino acid residues in positions 1 and 2 or 2 and 3 and a EF-hand2 comprising the substitution of the residues in positions 1 and 3 of the loop with alanine residues, which impairs metal binding in site 2. Advantageously, the EF-hand1 further comprises a tyrosine residue in position 7 and/or neutral or acidic residues different from T in positions 10 and 11 of the loop, for example AA or AE. More preferably, said calmodulin domain 1 variant polypeptide comprises or consists of the sequence SEQ ID NO: 17 or 60, which correspond to the peptides referred to as CaMΔ and CaMΔ-WT in the examples of the present application. CaMΔ and CaMΔ-WT are variants of the domain 1 from *Arabidopsis thaliana* calmodulin 3.

Another preferred calmodulin domain 1 variant polypeptide comprises a EF-hand1 comprising the deletion of the amino acid residues in positions 1 and 2 or 2 and 3 and a EF-hand2 comprising the deletion of at least one calcium-ligating residue in position 1 or 3 and at least one of the residues in positions 10 and/or 11 of the calcium-binding loop, preferably the residues in positions 3 and 10 or 3, 10 and 11.

Another preferred calmodulin domain 1 variant polypeptide comprises a EF-hand1 and EF-hand2, each comprising the deletion of the amino acid residues in positions 1 and 2 or 2 and 3 of the calcium-binding loop.

In another advantageous arrangement of said embodiment, the polypeptide of the invention is a calmodulin variant comprising four EF-hand motifs, respectively from EF-hand1, 2, 3 and 4 of calmodulin protein(s).

In a preferred calmodulin variant polypeptide, the EF-hand1 comprises the deletion of the amino acid residues in positions 1 and 2 or 2 and 3 and the EF-hand2, EF-hand3 and EF-hand4 comprise no deletion. More preferably, said polypeptide comprises or consists of the sequence SEQ ID NO: 18 derived from *Arabidopsis thaliana* calmodulin 3.

In another preferred calmodulin variant polypeptide, the EF-hand1 comprises the deletion of the amino acid residues in positions 1 and 2 or 2 and 3, the EF-hand2 comprises the deletion of at least one calcium-ligating residue in position 1 or 3 and at least one of the residues in positions 10 and/or 11 of the calcium-binding loop, preferably the residues in positions 3 and 10 or 3, 10 and 11, and the EF-hand3 and EF-hand4 comprise no deletion.

In another preferred calmodulin variant polypeptide, each of the EF-hand1 and EF-hand2 comprise the deletion of the amino acid residues in positions 1 and 2 or 2 and 3 and the EF-hand3 and EF-hand4 comprise no deletion.

In another preferred calmodulin variant polypeptide, each of the EF-hand1, 2 and 3 comprise the deletion of the amino acid residues in positions 1 and 2 or 2 and 3 and the EF-hand4 comprises no deletion.

In another preferred calmodulin variant polypeptide, each of the EF-hand1, 2, 3 and 4 comprise the deletion of the amino acid residues in positions 1 and 2 or 2 and 3. Even more preferably, said polypeptide comprises or consists of the sequence SEQ ID NO: 20 which is derived from *Arabidopsis thaliana* calmodulin 3.

In another preferred calmodulin variant polypeptide, each of the EF-hand1 and EF-hand3 comprise the deletion of the amino acid residues in positions 1 and 2 or 2 and 3 and the EF-hand2 and EF-hand4 comprise no deletion.

In another preferred embodiment, the polypeptide is coupled to a labeling agent which produces a detectable and/or quantifiable signal, in particular a radioactive, magnetic or luminescent (radioluminescent, chemiluminescent, bioluminescent, fluorescent or phosphorescent) agent. The labeled polypeptide may be labeled directly or indirectly, via covalent or non-covalent bonds, using standard conjugation techniques that are well-known to those skilled in the art.

Another aspect of the present invention relates to a fusion or chimeric protein comprising the polypeptide fused to another protein moiety, directly or through a peptide spacer. The protein/peptide moieties include those which allow the purification, detection, immobilization, and/or cellular targeting of the polypeptide of the invention, and/or which increase the affinity for uranyl, the bioavailability, and/or the production in expression systems of said polypeptide. These moieties may be selected from: (i) a labeling moiety such as a fluorescent protein (GFP and its derivatives, BlueFP, CyanFP, YellowFP, GreenFP and red-shifted GFP), (ii) a reporter moiety such as an enzyme tag (luciferase, alkaline phosphatase, glutathione-S-transferase (GST), β-galactosidase), (iii) a binding moiety such as an epitope tag (poly-His6, FLAG, HA, myc.), a DNA-binding domain, a hormone-binding domain, a poly-lysine tag for immobilization onto a support, and (iv) a targeting moiety for addressing the chimeric protein to a specific cell type or cell compartment. In addition, the sequence(s) advantageously comprise a linker which is long enough to avoid inhibiting interactions between said sequence(s) and the polypeptide sequence. The linker may also comprise a recognition site for a protease, for example, for removing affinity tags from the purified chimeric protein according to the present invention.

In a preferred embodiment the chimeric protein is a cameleon protein comprising tandem fusions of (1) the polypeptide of the invention, (2) a EF-hand protein-binding peptide that binds a complex between the polypeptide in (1) and calcium and/or uranyl, (3) a fluorescence-donor protein, and (4) a fluorescence-acceptor protein, wherein the fluorescence donor and acceptor proteins are at each end of the cameleon protein.

In some arrangements of said embodiment, the EF-hand protein-binding peptide is absent; in these arrangements, the polypeptide of the invention usually comprises two EF-hand motifs. Cameleon proteins without EF-hand protein-binding peptide may be derived from the sequence SEQ ID NO: 65.

In other arrangements of said embodiment, the cameleon protein further comprises a linker between the fluorescence donor and/or acceptor and the polypeptide of the invention, between the polypeptide of the invention and the EF-hand protein-binding peptide, and/or between the EF-hand protein-binding peptide and the fluorescence acceptor.

The fluorescence donor and acceptor proteins which are advantageously at each end of the cameleon protein are chosen from any protein capable of producing FRET such as with no limitation: Alexa proteins and GFP variants such as those disclosed for exampla in Shaner et al., Nature Methods, 2005, 12, 905-909; Erard et al., Molecular Biosystems, 2013, 9, 258-267; Fredj et al., PLOS ONE, 2012, 7, e49149 and PCT Application WO/2012/172095.

The fluorescence donor and acceptor proteins are advantageously chosen from a short-wavelength variant of GFP such as CyanFP or BlueFP, Turquoise, Turquoise 2, Aquamarine, Cerulean, Cerulean3, TFP1 and a long wave-length variant of GFP such as YellowFP, GreenFP and red-shifted GFP, Citrine, Venus and circularly permuted fluorescent proteins.

The polypeptide of the invention comprises advantageously four EF-hand motifs from EF-hand signaling protein(s) as defined above. Preferably said EF-hand motifs are from EF-hand signaling protein(s) of the calmodulin superfamily selected from the group consisting of calmodulin and troponin C.

In an advantageous arrangement of said embodiment, the cameleon protein is derived from calmodulin.

Many peptides which bind calmodulin in complex with calcium are known in the art (see for example Carafoli et al., Proc. Natl. Acad. Sci. USA., 2002, 99:1115-1122). Any of these peptides can be used in the cameleon protein of the invention, including with no limitations: the peptides M13 (amino acid sequence SEQ ID NO: 22 encoded by the nucleotide sequence SEQ ID NO: 21) and skMLCK (SEQ ID NO: 23) from skeletal myosin light chain kinase; the peptides MLCKp (SEQ ID NO: 24) and smMLCK (SEQ ID NO: 25) from myosin light chain kinase; the peptide named wasp venom or polistes mastoparan (SEQ ID NO: 26); the peptide p21 (SEQ ID NO: 27); the peptides disclosed in Shifman J. M. and Mayo, L., PNAS, 2003, 100, 13274-such as melittin (SEQ ID NO: 28), spectrin (SEQ ID NO: 29), CaMKI (SEQ ID NO: 30), CaMKII (SEQ ID NO: 31), CaMKK (SEQ ID NO: 32) and peptide1 (SEQ ID NO: 33); the peptides from cyclic nucleotide phosphodiesterase (Olwin & Storm, 1985); the peptides from caldesmon (Yazawa et al., 1987) and the synthetic peptide derived from the plasma membrane $Ca^{2+}$ pump (Yazawa et al., 1992).

Preferably, the cameleon protein comprises a short-wavelength variant of GFP such as CyanFP or BlueFP, a polypeptide of the invention derived from calmodulin, a linker, the calmodulin-binding peptide of myosin light chain kinase (peptide M13), and a long wave-length variant of GFP such as YellowFP, GreenFP and red-shifted GFP.

Preferred cameleon proteins are derived from the calmodulin variant polypeptides as defined above. Examples of preferred calmodulin-derived cameleon proteins of the invention comprise or consist of an amino acid sequence selected from the group consisting of the sequences SEQ ID NO: 35, 38, 61, 63 and 67.

Alternatively, the four elements of the cameleon protein as described above can be divided in two separate fusion proteins, which are then combined together to obtain a functional biosensor capable of detecting uranium: a first fusion protein with the fluorescence donor fused to one of the polypeptide or the polypeptide-binding peptide, and a second fusion protein with the fluorescence acceptor fused to the polypeptide or polypeptide-binding peptide which is not fused to the fluorescence donor. These types of cameleon proteins are described for example in Miyawaki et al., Proc. Natl. Acad. Sci. USA., 1999, 96, 2135-40.

The cameleon protein is a uranyl biosensor that can be used in vitro as uranyl analysis reagent for the detection of uranyl in an environment (water, soil, effluents) or in biological samples from individuals (biological fluids). It is also used as cell imaging reagent or diagnostic reagent for the detection of uranyl in situ in recombinant cells (whole-cell biosensor) or non-human transgenic organisms expressing the cameleon protein.

The invention encompasses polypeptides and derived fusion proteins comprising or consisting of natural amino acids (20 gene-encoded amino acids in a L- and/or D-configuration) linked via a peptide bond as well as peptidomimetics of such protein where the amino acid(s) and/or peptide bond(s) have been replaced by functional analogues. Such functional analogues include all known amino acids other than said 20 gene-encoded amino acids. A non-limitative list of non-coded amino acids is provided in Table 1A of US 2008/0234183 which is incorporated herein by reference. The invention also encompasses modified polypeptides/fusion proteins derived from the above polypeptides/fusion proteins by introduction of any modification into one or more amino acid residues, peptide bonds, N- and/or C-terminal ends of the protein, as long as the uranyl-binding activity is maintained in the modified polypeptide/protein. These modifications which are introduced into the polypeptide/protein by the conventional methods known to those skilled in the art, include, in a non-limiting manner: the substitution of a natural amino acid with a non-proteinogenic amino acid (D amino acid or amino acid analog); the modification of the peptide bond, in particular with a bond of the retro or retro-inverso type or a bond different from the peptide bond; the cyclization, and the addition of a chemical group to the side chain or the end(s) of the protein, in particular for coupling an agent of interest to the polypeptide/fusion protein of the invention.

In another preferred embodiment, the polypeptide or fusion protein is immobilized on the surface of a solid support, such as with no limitation, a plate, a slide, a strip, a fiber, a gel, a felt support, wells, microparticles, or biologically modified ceramics (biocers; Bottcher et al., J. Mater. Chem., 2004, 14, 2176-2188).

Another aspect of the invention relates to an isolated polynucleotide encoding a polypeptide or chimeric protein of the invention. The synthetic or recombinant polynucleotide may be DNA, RNA or combination thereof, either single- and/or double-stranded. Preferably the polynucleotide comprises a coding sequence which is optimized for the host in which the polypeptide or chimeric protein is expressed. In a preferred embodiment, the polynucleotide comprises or consists of a sequence selected from the group consisting of the sequences SEQ ID NO: 16, 34, 59, 62, 64 and 68.

Another aspect of the invention relates to a recombinant vector comprising said polynucleotide. Preferably, said recombinant vector is an expression vector capable of expressing said polynucleotide when transfected or transformed into a host cell such as a eukaryotic or prokaryotic cell like a mammalian, bacterial or fungal cell. The polynucleotide is inserted into the expression vector in proper orientation and correct reading frame for expression. Preferably, the polynucleotide is operably linked to at least one transcriptional regulatory sequence and, optionally to at least one translational regulatory sequence. In a preferred embodiment, the polynucleotide is under the control of a promoter which is upregulated in response to uranium such as for example Caulobacter urc-A promoter (Hillson et al., Applied and Environmental Microbiology, 2007, 73, 7615-7621). Recombinant vectors include usual vectors used in genetic engineering and gene therapy including for example plasmids and viral vectors.

Another aspect of the invention provides a host cell or a non-human organism transformed with said polynucleotide or recombinant vector. Preferably, said modified host cell or non-human transgenic organism is resistant to radiations, and/or pollutants such as for example nitrates and toxic metals. The non-human transgenic organism is obtained from a unicellular or pluricellular microorganism or a higher eukaryotic organism. In a preferred embodiment said modified host cell is a prokaryotic cell such as a bacteria. In another embodiment, said non-human transgenic organism is a transgenic plant, nematode, zebrafish or algae.

The polynucleotide, vector, cell, and non-human transgenic organism of the invention are useful for the production of the polypeptide/chimeric protein of the invention using well-known recombinant DNA techniques.

Another aspect of the invention relates to the use of the polypeptide, fusion protein, host cell, non-human transgenic organism, in vitro or in vivo, as uranyl chelating agent. The chelating agent is useful for the detection, the decontamination, and/or the bioremediation of uranium contamination in an environment (water, soil, effluents, . . . ) or in individuals.

The labelled polypeptide/fusion protein such as the polypeptide comprising a fluorescent residue like a tyrosine residue in position 7 of the loop or the cameleon protein, is a uranyl biosensor. It can be used in vitro as uranyl analysis or diagnostic reagent for the detection of uranyl in an environment (water, soil, effluents, . . . ) or in biological samples from individuals (biological fluids, . . . ). In addition, the cameleon protein is also used as cell imaging reagent, diagnostic reagent and bioindicator for the detection of uranyl in situ in modified cells (for example recombinant cells) or non-human transgenic organisms expressing the cameleon protein.

The polynucleotide according to the invention is prepared by the conventional methods known in the art. For example, it is produced by amplification of a nucleic sequence by PCR or RT-PCR, by screening genomic DNA libraries by hybridization with a homologous probe, or else by total or partial chemical synthesis. The recombinant vectors are constructed and introduced into host cells by the conventional recombinant DNA and genetic engineering techniques, which are known in the art.

The polypeptide/chimeric protein is prepared by the conventional techniques known to those skilled in the art, in particular by solid-phase or liquid-phase synthesis or by expression of a recombinant DNA in a suitable cell system (eukaryotic or prokaryotic). More specifically, the polypeptide can be solid-phase synthesized, according to the Fmoc technique, originally described by Merrifield et al. (J. Am. Chem. Soc., 1964, 85: 2149-), and purified by reverse-phase high performance liquid chromatography; the polypeptide/chimeric protein can be produced from the corresponding cDNAs, obtained by any means known to those skilled in the art; the cDNA is cloned into a eukaryotic or prokaryotic expression vector and the protein produced in the cells modified with the recombinant vector is purified by any suitable means, in particular by affinity chromatography.

The practice of the present invention will employ, unless otherwise indicated, conventional techniques which are within the skill of the art. Such techniques are explained fully in the literature.

In addition to the above arrangements, the invention also comprises other arrangements, which will emerge from the description which follows, which refers to exemplary embodiments of the subject of the present invention, with reference to the attached drawings in which:

FIG. 1 is a schematic of calmodulin. A. Schematic of domain 1 of Paramecium tetraurelia calmodulin (PDB code 1EXR) which comprises two calcium-binding sites (site 1 and site 2) which are part of a canonical EF-hand motif (EF-hand1 and EF-hand2, respectively for site 1 and site 2). B. Structural model of the calcium-binding site 1 of *Arabidopsis thaliana* calmodulin showing the coordinating amino acids. C. Amino acid sequence of calmodulin site 1 from *Arabidopsis thaliana* (CaM-WT) and from the peptide CaM1 and CaMΔ analysed in the present study. In the CaM1 and CaMΔ peptides, the metal-binding ability of site 2 was impaired by replacing the aspartate residues in positions 57 and 59 of calmodulin (positions 58 and 60 of CaM1) with alanines. In addition, the threonine residue in position 31 and the lysine residue in position 32 of CaM1 (positions 10 and 11 of site 1) have each been substituted with an alanine residue to obtain an efficient CK2 consensus sequence that targets phosphorylation of threonine 9 (T9) of the metal-binding loop (T30 in the peptide) and a tyrosine was introduced at position 28 of peptide CaM1 (position 7 of the metal-binding loop) to allow the monitoring of uranyl and calcium-binding and the determination of their binding affinities, by following tyrosine fluorescence emission at 302 nm.

FIG. 2 represents Structural models obtained by molecular dynamics of the CaM1P-U (A), CaMΔP-U (B) CaM1-U (C) and CaMΔ-U (D) complexes. E=glutamic acid, D=aspartic acid, Y=tyrosine, T=threonine, Tp=Phosphothreonine.

FIG. 3 shows the binding thermograms of the CaMΔ and CaMΔP peptides with uranyl at pH 6 (A) and pH 7 (B). Conditions: 10 μM CaMΔ or CaMΔP, 100 μM IDA, 20 mM MES and 100 mM KCl. Full square: CaMΔP. Full circle: CaMΔ.

FIG. 4 shows the binding thermograms of the CaMΔ with uranyl in the absence (empty triangle) and in presence (empty circle) of 10 mM $CaCl_2$. Conditions: 10 μM CaMΔ, 100 μM IDA, 20 mM MES and 100 mM KCl.

FIG. 5 shows the growth curve of three *E. coli* strains transformed with respectively, the expression vector without insert (as a control) or vectors expressing recombinant CaM1 or CaMΔ peptide, in the presence or absence of uranyl acetate (U). Control (empty circle). Control+U (full circle). CaM1 (empty triangle). CaM1+U (full triangle). CaMΔ(empty square). CaMΔ+U (full square). IPTG was added at t=105 min; 50 μM uranyl acetate (U) or 100 μM sodium acetate were added at t=135 min.

FIG. 6 shows the emission spectra of cameleon biosensor WT protein (excited at 440 nM) at varying $CaCl_2$ concentrations between 0 μM to 10 μM. 0 μM Ca (full diamond). 2 μM Ca (empty circle). 4 μM Ca (empty triangle). 6 μM Ca (full circle). 8 μM Ca (cross). 10 μM Ca (empty square). Vertical arrow indicates an increase in FRET detection with increasing Ca concentrations.

FIG. 7 shows the emission spectra of cameleon biosensor WT protein (excited at 440 nM) at varying uranyl nitrate concentrations between 0 μM to 10 μM. 0 μM $UO_2$ (full black circle). 2 μM $UO_2$ (empty square). 4 μM $UO_2$ (full triangle). 6 μM $UO_2$ (empty circle). 8 μM $UO_2$ (full grey circle). 10 μM $UO_2$ (empty diamond). Vertical arrow indicates an increase in FRET detection with increasing uranyl concentrations.

EXAMPLE 1

Figure 1:
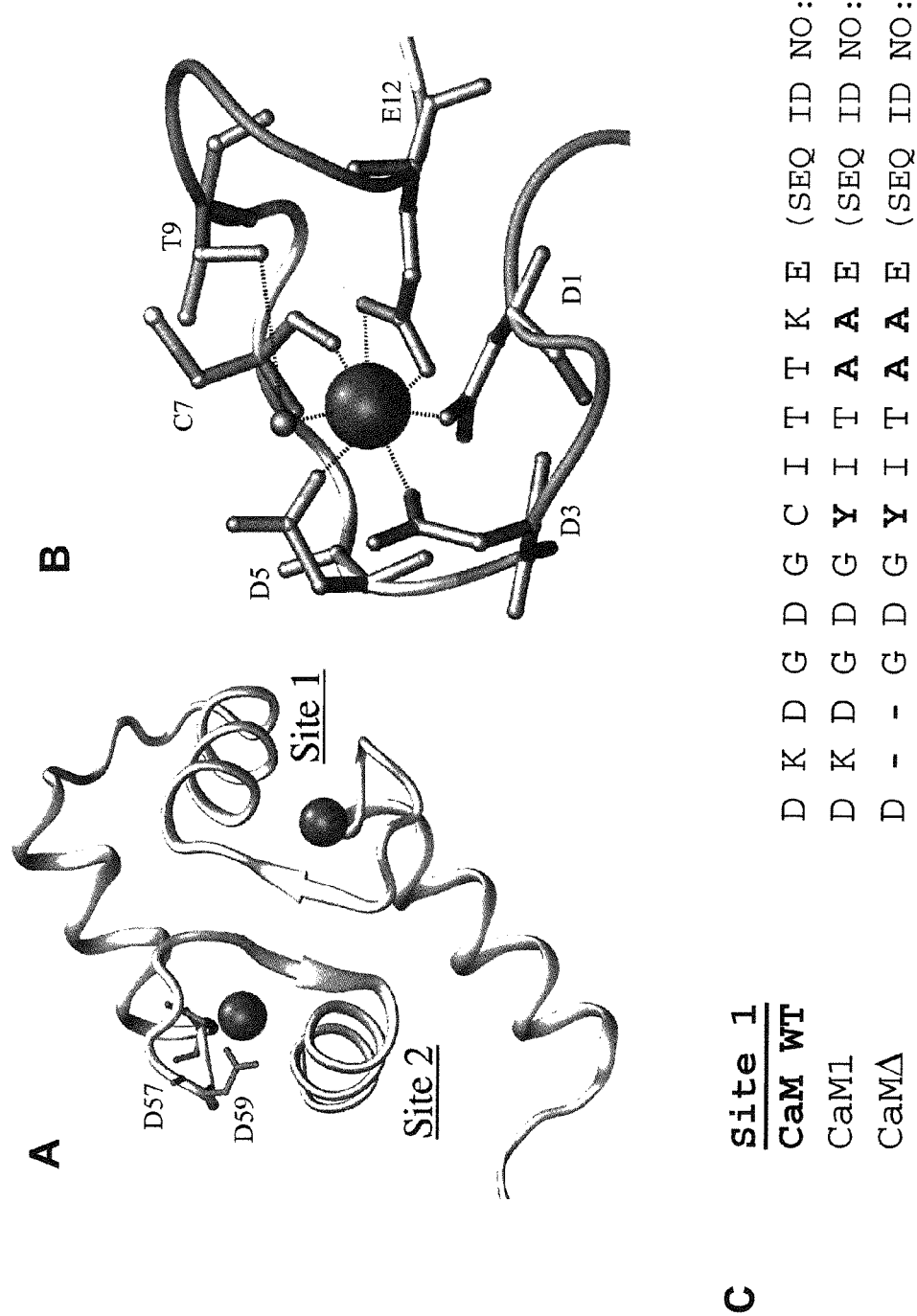
Figure 2:
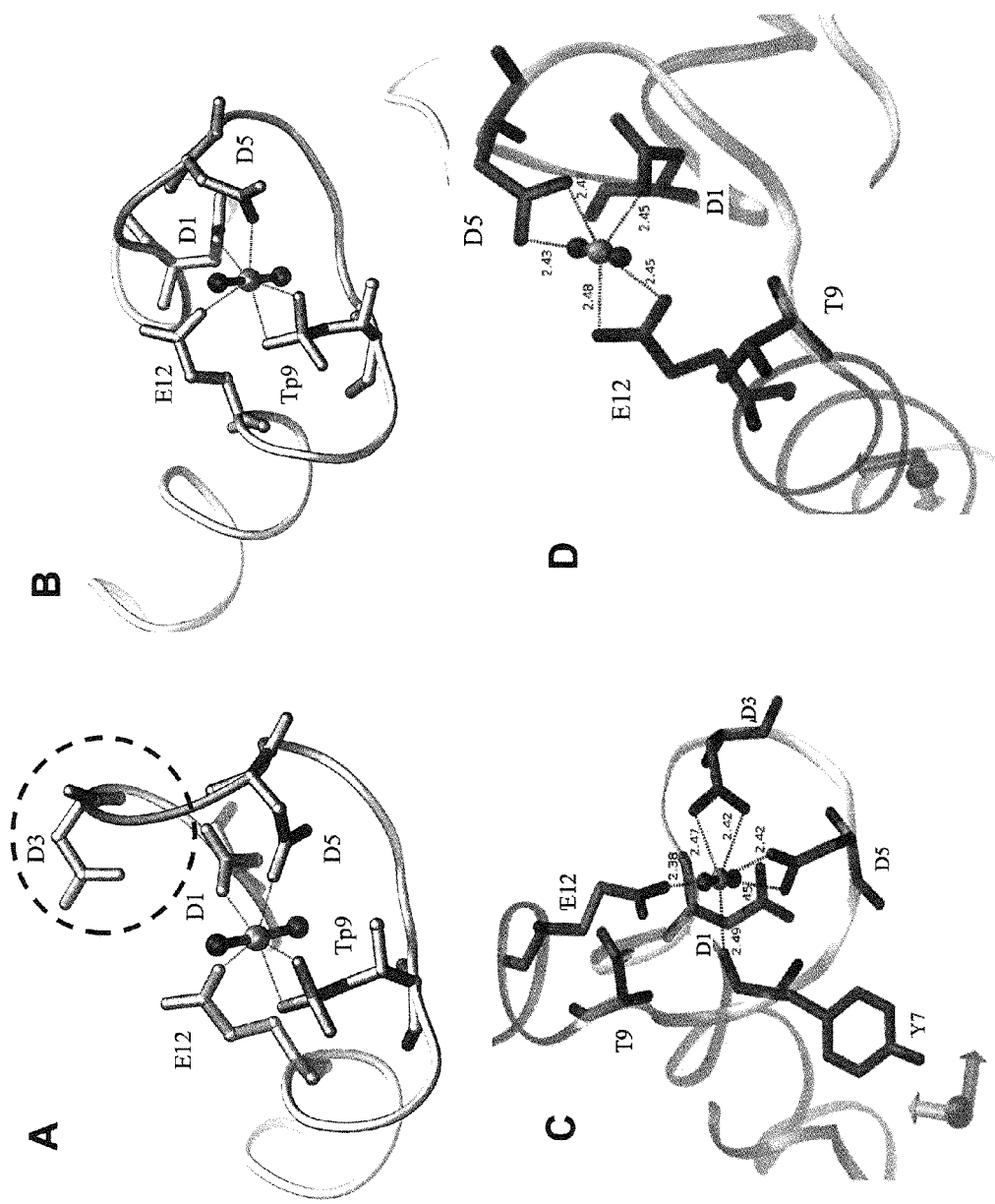

Construction and Characterization of Calmodulin Peptides CaMΔ, CaMΔ3 and CaMΔ-WT 1. Methods The recombinant peptides were produced in *E. coli*. A histidine-tag followed by the Tobacco Etch Virus protease (TEV) recognition sequence was introduced at the N-terminus, allowing the purification of the pepti using two subsequent chromatography steps on Ni-columns.

1.1 Engineering and Purification of Calmodulin Derived Peptides

The CaM1 construct containing the *Arabidopsis thaliana* sequence of calmodulin domain 1 was obtained as previously described (Pardoux et al., PLoS One, 2012, 7, e41922) and used as a template for new constructs. The CaM1 construct (nucleotide sequence SEQ ID NO: 39/amino acid sequence SEQ ID NO: 40) comprises the following mutations, by reference to CaM1 amino acid sequence: (1) C28Y mutation to allow the monitoring of uranyl- and calcium-binding and the determination of their binding affinities, by following tyrosine fluorescence emission at 302 nm, (2) T31A and K32A mutations to enable efficient phosphorylation of T30 by CK2, and (3) D58A and D60A mutations to inactivate the metal-binding site 2 of domain 1.

To obtain CaMΔ construct (nucleotide sequence SEQ ID NO: 16/amino acid sequence SEQ ID NO: 17), deletions of K23 and D24 were produced with the QuickChange site-directed mutagenesis kit (STRATAGENE) and specific primer pairs DGD S (SEQ ID NO: 41) and DGD AS (SEQ ID NO: 42), according to the manufacturer's instructions. The engineering plasmid was called pQE-CaMΔ.

To obtain CaMΔ3 construct (nucleotide sequence SEQ ID NO: 55/amino acid sequence SEQ ID NO: 56), deletion of D24 was produced with the QuickChange site-directed mutagenesis kit (STRATAGENE) and specific primer pairs S-Δ3Y (SEQ ID NO: 57) and AS-Δ3Y (SEQ ID NO: 58), according to the manufacturer's instructions. The engineering plasmid was called pQE-CaMΔ3.

We also produced CaMΔ-WT (nucleotide sequence SEQ ID NO: 59/amino acid sequence SEQ ID NO: 60). The protein sequence is the same than those of CaMΔ except that A31 and A32 were replaced by T31 and K32.

Recombinant fusion proteins expressed in *E. coli* strain M15Rep4 (QIAGEN) were grown at 37° C. in LB medium containing ampicillin (50 μg/mL) and kanamycin (50 μg/mL). Expression was induced by addition of 0.1 mM isopropyl-D-thiogalactoside once $OD_{600}$ reached 0.5, and the cultures were further incubated for 5 h at 37° C. Cellular extracts were obtained by French press lysis and a centrifugation step of 30 min at 15000 rpm, and were applied at a 1 mL/min flow rate on a 5 mL HiTrap Chelating Column (GE HEALTHCARE) in buffer A (50 mM Tris-HCl, 0.5 M NaCl, 25 mM imidazole buffer pH 7.5) containing 1 mM 4-(2-Aminoethyl)benzenesulfonyl fluoride hydrochloride (AEBSF). The proteins were eluted from the nickel resin at a 4 mL/min flow rate using buffer A supplemented with 150 mM imidazole. The proteins were dialyzed against buffer A and the His-Tags were removed by incubation overnight at 4° C. with TEV protease, followed by separation using a HiTrap Chelating Column. Recombinant proteins were dialyzed against 50 mM Tris-HCl, 150 mM NaCl, pH 7.5. The protein concentrations were measured according to the BC Assay (UPTIMA) with bovine serum albumin as standard. The proteins were concentrated using the Microcon filtration system (Amicon Millipore®), with a cut-off point of 3 kDa.

Phosphorylation of the peptide CaMΔ was performed as previously described in Pardoux et al., PLoS One, 2012, 7, e41922.

1.2 Tyrosine Fluorescence Titrations

The metal-binding affinity of the various peptides for calcium and uranyl was examined by monitoring the fluorescence intensity of the single tyrosine residue (Tyr28).

The uranyl solutions were prepared extemporaneously by diluting a 0.1 M stock solution of uranyl nitrate (pH 3.5, stored frozen at −20° C.) in the final buffer. Fluorescence titrations in the presence of uranyl were performed using a 10 μM peptide solution in MES (20 mM, pH 6) or Tris (20 mM, pH 7) buffer with 100 mM KCl and 100 μM iminodiacetate (IDA). Fluorescence titrations in the presence of calcium were performed in a 10 μM peptide solution in MES (20 mM, pH 6) or Tris (20 mM, pH 7) buffer with 100 mM KCl. To remove any trace of calcium from the samples, each sample solution was incubated 1 h with Chelex®-100 before uranyl or calcium addition.

Spectra were collected on a Cary Eclipse spectrofluorimeter at 25° C., with 270 nm excitation. Emission was observed from 290 to 350 nm. The excitation and emission slits were 10 nm. A 15 min equilibration time was respected before each measurement. The reported stability constants are averages of three experimental values.

Competition experiments between calmodulin-derived peptides CaM peptides and IDA were performed to determine the conditional dissociation constants of the peptide-uranyl complexes at pH 6 and pH 7. IDA has a moderate affinity for uranyl and forms three major complexes: $UO_2IDA$, $[UO_2(IDA)_2]^{2-}$, and $[(UO_2)_2(IDA)_2(OH)_2]^{2-}$. The conditional stability constants of these three species were calculated from the $pK_{as}$ and the stability constants at 25° C. and 0.1 M ionic strength given by Jiang et al. (Inorg. Chem., 2003, 42, 1233-1240). These three conditional stability constants were fixed in the spectral data analysis, which was performed using the program SPECFIT (Binstead et al., Specfit Global Analysis System Version 3.0.34, 2003). Identical values were obtained for the conditional stability constants of the $UO_2$-P complexes (where P stands for peptide), either considering that the $UO_2$-P complex emits or not. In the former case, the spectrum of the $UO_2$-P complex was calculated to be zero, as the fluorescence emission of tyrosine was totally quenched in the complex.

For titrations in the presence of calcium, the conditional dissociation constants ($K_d$) were determined by fitting the difference between fluorescence intensities measured in the presence (F) and in the absence (F0) of calcium, according to a one site saturation model: $\Delta F=(F_{max}\times[Ca])/(Kd+[Ca])$ using SigmaPlot 10.0 software (Systat Software). In this equation, $F_{max}$ corresponds to the maximum of fluorescence determined by the software.

1.3 Exposure of *E. coli* Cells Producing or not the CaMΔ Peptide to Uranyl Toxicity

*E. coli* cells were grown overnight in LB-MES 100 mM, pH 5.5. The cells where transferred to a LB-glucose (4 g/L) medium at pH 4.5, inoculated at 1/100 volume. IPTG was added at a $OD_{600nm}$=0.4. After 30 minutes, 50 μM uranyl (acetate)$_2$ or 100 μM Na-acetate was added to the medium. Cell growth was followed by measuring the absorption at 600 nm.

Figure 3:
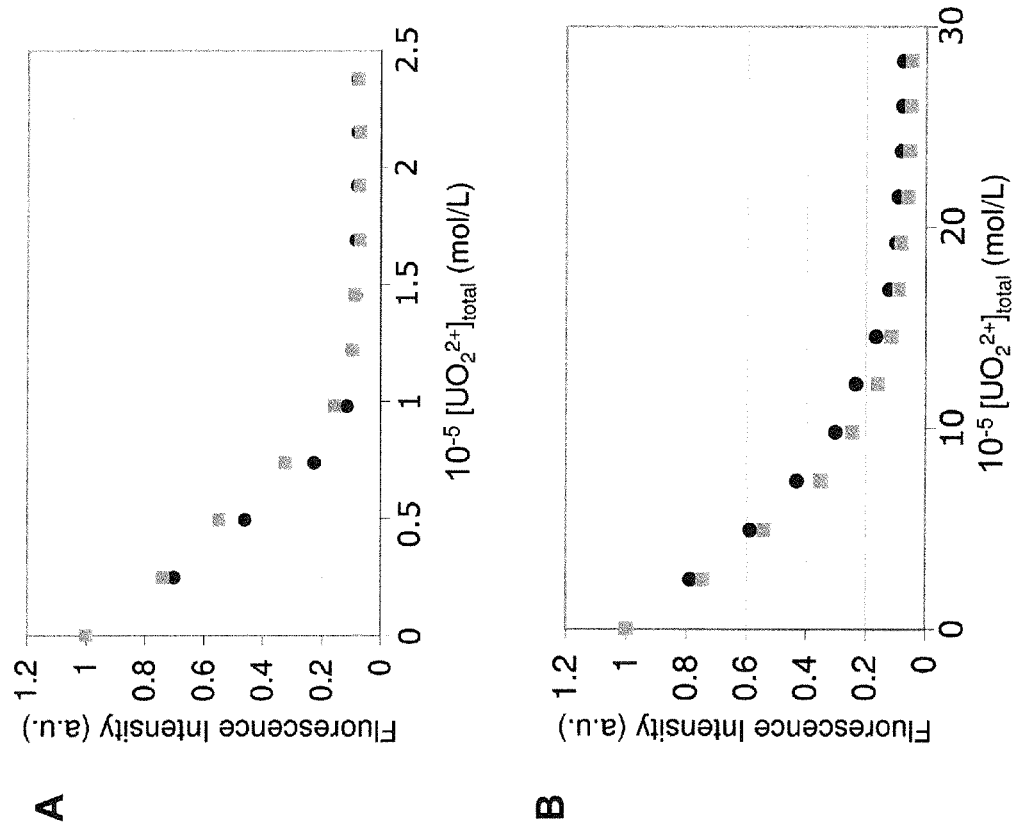

2. Results 2.1 Binding Affinity of the CaMΔ, CaMΔ-WT and CaMΔ3 Peptides for Uranyl The peptides were prepared at a 10 μM concentration in 20 mM MES pH 6 or Tris pH 7, with 0.1 M KCl and 100 μM IDA. Increasing concentrations of uranyl nitrate were added to the peptide solution, until the peptide to uranyl ratio was approximately 1:4. By using this stoichiometric ratio, the protein samples were not affected by uranyl addition (as monitored by UV-Vis absorption), which is crucial for the interpretation of the results. Addition of uranyl nitrate decreased the fluorescence signal emitted by the single tyrosine present in the peptides at position 7 of the metal-binding loop (FIG. 3). Tyrosine fluorescence quenching by uranyl has been reported in the literature for other proteins such as transferrin.

Conditional dissociations constants of the peptide—uranyl complexes (Kd) resulting from the competition experiments with IDA were determined at pH 6 and pH 7 for the CaMΔ peptide and at pH 6 for the CaMΔWT and CaMΔ3 peptides.

Conditional dissociation constants of 1.8 (±0.5) $10^{-10}$ M and 2 (±0.1) $10^{-10}$ M were calculated at pH 6 and pH 7 for the CaMΔ—uranyl complex. There is no significant effect of pH on the affinity of the peptide CaMΔ for uranyl. The affinity of the CaMΔ peptide is two orders of magnitude greater than that of the CaM 1 peptide, possessing a 12 amino acid long binding loop, which has a Kd of 25 $10^{-9}$ M at pH 6 (Pardoux et al., PLoS One, 2012, 7, e41922). Interestingly the peptide CaMΔ3, in which only one aspartate at position 3 of the loop has been deleted, has a much lower affinity for uranyl. A conditional dissociation constant of 130±10 $10^{-9}$M was obtained for uranyl at pH 6. The affinity of this peptide for uranyl is 722 times lower than that of the CaMΔ peptide. It is also lower than the affinity of CaM1 for uranyl. This experiment demonstrates that it is not sufficient to suppress (at least) one of the aspartate ligands to increase the affinity for uranyl, but that structural factors significantly affect the affinity of the peptide binding loop for uranyl.

Finally, a conditional dissociation constant of 2±0.1 $10^{-10}$M was obtained for the CaMΔ-WT peptide, differing from the CaMΔ peptide by residues at positions 10 and 11 of the metal binding loop (numbering according to the native sequence of 12 AA). A threonine and a lysine are present in this peptide instead of two alanines in the CaMΔ peptide. The affinity for uranyl is equivalent to that of CaMΔ.

The phosphorylated peptide CaMΔP presents similar binding affinities for uranyl, with conditional dissociation constants Kd=4 (±0.09) $10^{-10}$ M at pH 6 and Kd=1.3 (±0.3) $10^{-10}$ M at pH 7.

Moreover, both peptides have a very low affinity for calcium. Conditional dissociation constants in the millimolar range were observed for the CaMΔ-$Ca^{2+}$ complex at pH 6 (Kd>1 mM) and at pH 7 (Kd=8.7 mM). Similar dissociation constants were observed for the phosphorylated peptide CaMΔP with Kd of 7.8 mM at pH 6 and Kd=4.2 mM at pH 7.

2.2 Competition Experiments with Calcium

The selectivity of the two peptides (CaMΔ and CaMΔP) for uranyl as compared to calcium is of the order of $10^7$. To check if this selectivity is actually observed in a medium containing both uranyl and calcium, the binding isotherm of uranyl was measured in the presence of 10 mM $CaCl_2$ in the solution.

Figure 4:
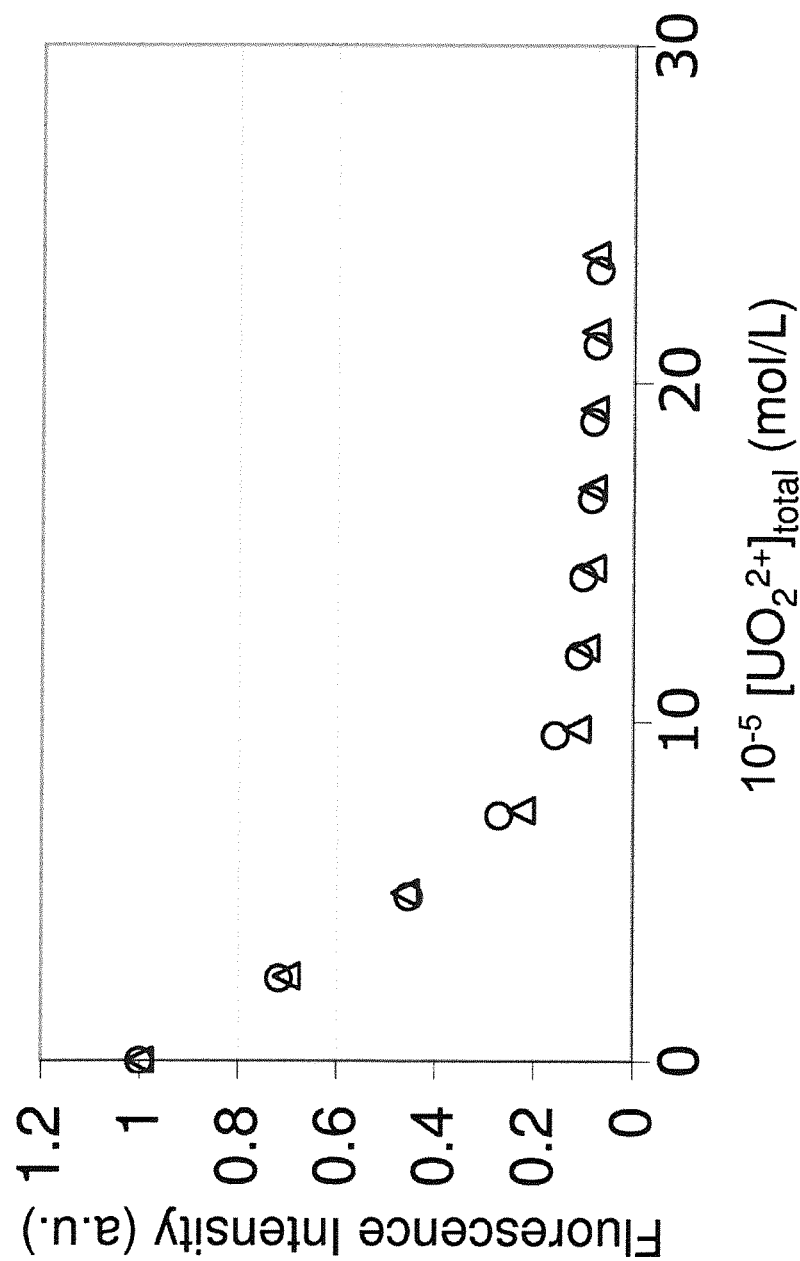

FIG. 4 shows the superimposition of binding thermograms corresponding to Tyr fluorescence quenching (i.e. uranyl binding) in the absence and in the presence of 10 mM $CaCl_2$. These results show that calcium has a very modest effect on uranyl titration.

The results of this competition experiment show that these peptides can be used for uranyl detection in the presence of large concentrations of calcium.

Figure 5:
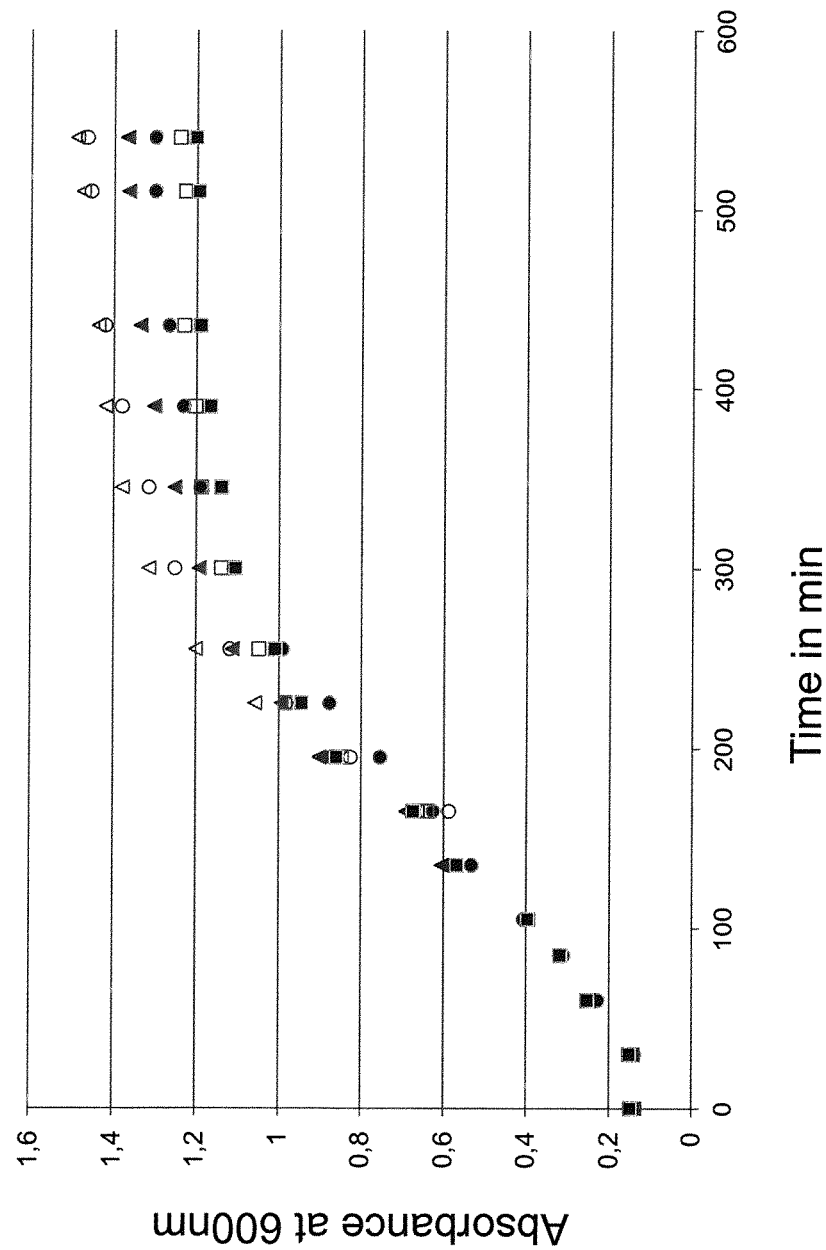

2.3 the Expression of the CaMΔ Peptide in *E. coli* Cells Decreases Uranyl Toxicity to the Cells FIG. 5 shows growth curves recorded with *E. coli* cells exposed either to 50 μM uranyl acetate, or to 100 μM Na acetate as a control, in LB glucose medium at pH 4.5. Exposure conditions are detailed in the Methods. The FIG. 5 shows that uranyl exposure stops *E. coli* growth rapidly (full signs as compared to empty signs) except for the cells expressing the CaMΔ peptide. The growth of the cells expressing the CaMΔ peptide is lower than that of the other strains. This may be due to a too strong protein overexpression. However, addition of uranyl didn't affect anymore the growth of this strain. These results suggest that the chelation of uranyl by the CaMΔ peptide protect the whole cells by reducing uranyl toxicity.

Conclusions

CaMΔ peptide presents an affinity for uranyl in the subnanomolar range and a very high selectivity towards calcium. It is expressed in high quantities in *E. coli* cells.

For these reasons, it is a promising tool for the development of biosensors (in vivo and in vitro) or efficient chelating systems in vitro.

Figure 10:
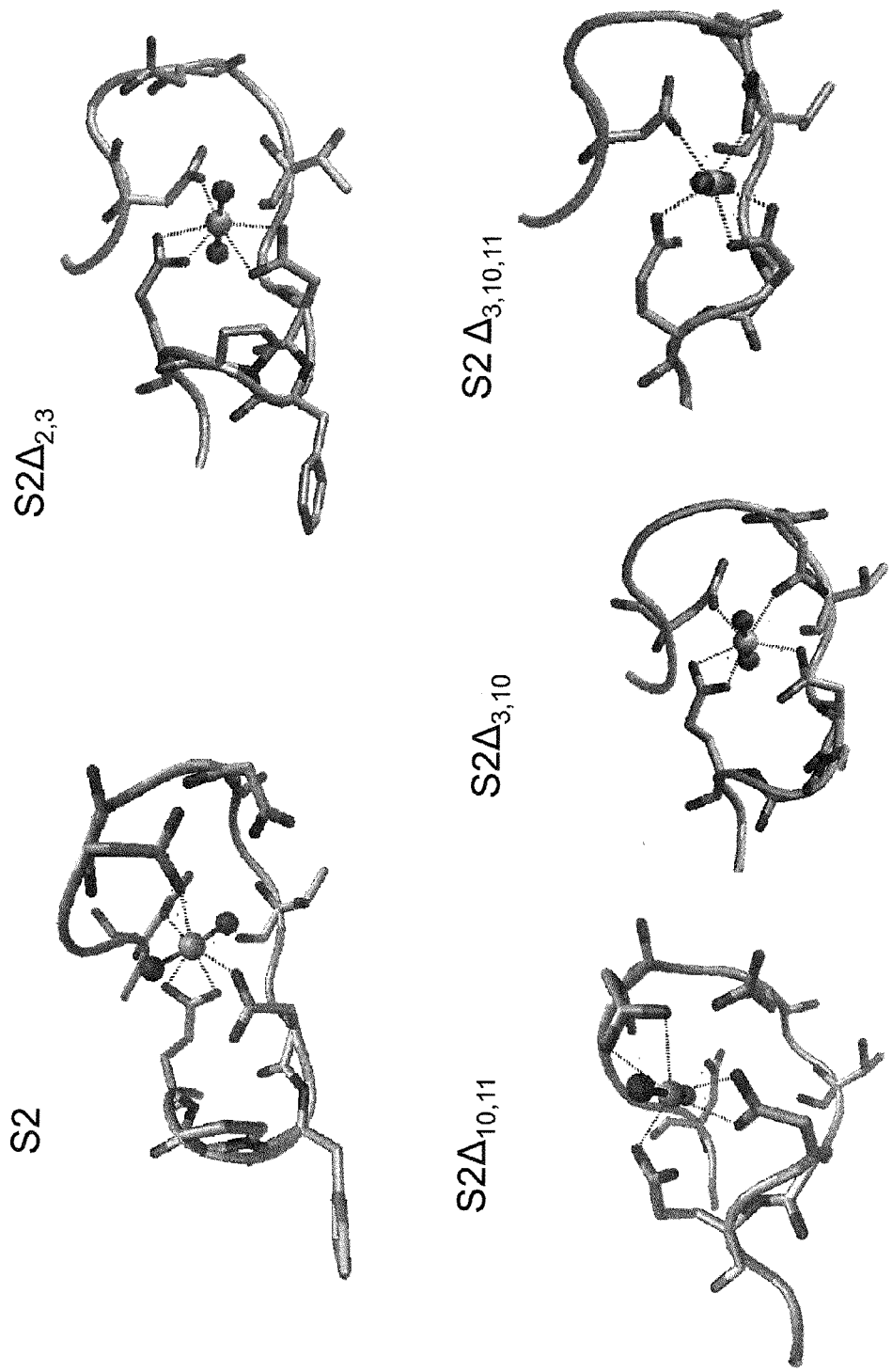
FIG. 10 shows structural models of the Ef-hand2 obtained by molecular dynamics simulations. This figure shows that uranyl coordination may be efficiently achieved in shorter binding loops, i.e. using deletion of at least two residues.

The use of the binding loop sequence of CaMΔ for the other sites of calmodulin may not be as efficient for selecting uranyl binding at these sites as at site one. Therefore, structural parameters that could increase the affinity of site 2 toward uranyl as well as its uranyl/calcium specificity were explored using molecular dynamics. Two indicative informations can be obtained using molecular dynamic simulations; the first one concerns the structural model; the second one concerns the stabilisation energy associated with uranyl binding on the protein. The structural models of the Ef-hand2 obtained by molecular dynamics simulations show that uranyl coordination may be efficiently achieved in shorter binding loops, i.e. using deletion of at least two residues (FIG. 10).

EXAMPLE 2

Construction and Characterization of Calmodulin Derived Cameleon Biosensors

1. Methods 1.1 Construction of Expression Vector for Cameleon Biosensors

Cloning steps were made with standard methods using XL1Blue cells as *E. coli* strain. All mutations were made using a QuickChange site-directed mutagenesis kit (Stratagene) and specific primer pairs according to the manufacturer.

The gene coding for the cameleon biosensor WT (denoted eCFP-CaM-Linker-M13-eYFP) was constructed in three steps. The gene encoding the wild-type CaM from *A. thaliana* fused with a linker and the CaM-binding peptide of myosin light-chain kinase (M13) was synthetized by Eurofins MWG and cloned into the pQE30 plasmid (QIAGEN) between Sac I and Sal I restriction sites.

Then, the enhanced Cyan Fluorescent Protein (eCFP) gene containing the TEV protease recognition site upstream of the coding sequence of eCFP was PCR-amplified using the S-TEV-eCFP-BamHI (SEQ ID NO: 43) and AS-eCFP-SacI (SEQ ID NO: 44) primers and cloned upstream the CaM-linker-M13 gene, between BamH I and Sac I restriction sites.

Finally, the enhanced Yellow Fluorescent Protein (eYFP) was PCR-amplified using the S-eYFP-SalI (SEQ ID NO: 45) and AS-eYFP-HindIII (SEQ ID NO: 46) primers and cloned downstream the CaM-linker-M13 gene, between the Sal I and Hind III restriction sites. Both genes contained no stop codon except for the eYFP gene. The cameleon biosensor WT corresponds to the cDNA of SEQ ID NO: 47 and the protein of SEQ ID NO: 48.

The construction of expression vector for the cameleon biosensor Δ was made by using the cameleon biosensor WT gene as a template and primers S-Δ (SEQ ID NO: 49) and AS-Δ (SEQ ID NO: 50). The constructions of expression vectors for the cameleon biosensor WT-S2M or for the cameleon biosensor Δ-S2M (S2M corresponding to the inactivation of site 2 of the domain 1) were made using as a template the cameleon biosensor WT gene or the cameleon biosensor Δ gene respectively and primers S-S2M (SEQ ID NO: 51) and AS-S2M (SEQ ID NO: 52). The cameleon biosensor Δ corresponds to the cDNA of SEQ ID NO: 34 and the protein of SEQ ID NO: 35. The cameleon biosensor WT-S2M corresponds to the cDNA of SEQ ID NO: 53 and the protein of SEQ ID NO: 54. The cameleon biosensor Δ-S2M corresponds to the cDNA of SEQ ID NO: 36 and the protein of SEQ ID NO: 37.

1.2 Expression of the Cameleon Biosensors

The recombinant vectors pQE30 containing the biosensor genes were introduced in the *E. coli* strain M15Rep4. Recombinant fusion proteins were expressed as follows: the overexpression strain was grown at 37° C. in LB medium containing ampicillin (50 μg/mL) and kanamycin (50 μg/mL) until $OD_{600}$ reached 0.5. Expression was then induced by addition of 0.1 mM isopropyl-D-thiogalactoside (IPTG) and the cultures were further incubated for 20 h at 17C. Cells were collected by centrifugation 20 min at 5000 rpm, and the bacterial pellet was frozen and stored at −80° C.

1.3 Purification of the Cameleon Biosensors

Bacteria were resuspended in buffer A (50 mM Tris-HCl, 0.5 M NaCl, 25 mM imidazole pH 7.5) containing 1 mM 4-(2-Aminoethyl)benzenesulfonyl fluoride hydrochloride (AEBSF)+15 g/mL DNAse1+30 mM MgSO$_4$. The cellular extracts were obtained by French Press lysis and a centrifugation step of 30 min at 15 000 rpm. The cellular extracts were applied on a 5 mL HiTrap™ Column (GE Healthcare) in buffer A at 1 mL/min flow rate. The proteins were eluted from the nickel resin at 4 mL/min flow rate using an imidazole gradient. The proteins were dialyzed against buffer A and the His-Tags were removed by incubation overnight at 4° C. in presence of the TEV protease followed by separation using HiTrap Chelating Column. Gel Filtration was performed for further purification of the proteins using a 26/600 Superdex 200 column (GE HealthCare) and 50 mM Tris-HCl buffer, pH 7.5, supplemented with 150 mM NaCl. The protein concentrations were measured according to the BC Assay from Uptima with bovine serum albumin as standard. The proteins were concentrated using Microcon® filtration system (Amicon Millipore®, with a cut off of 10 kDa).

1.4 FRET Measurement

Fluorescence experiments were performed using an Infinite 1000 (TECAN). Cameleon biosensor WT proteins were first incubated with an excess of ethylenediaminetetraacetic acid (EDTA) and dialyzed overnight against 50 mM Tris-Cl pH 7 containing Chelex® resin. This step is used to remove calcium likely to be present in the different CaM-binding sites. For each measurement, 1 µM of protein was mixed in 200 µL of 50 mM Tris-Cl pH 7 buffer (treated with Chelex®) at 25° C. CaCl$_2$ or uranyl nitrate were added at varying concentrations between 0 and 10 µM. Excitation was performed at 440 nm and the emission spectrum recorded between 450 and 570 nm.

2. Results

Figure 6:
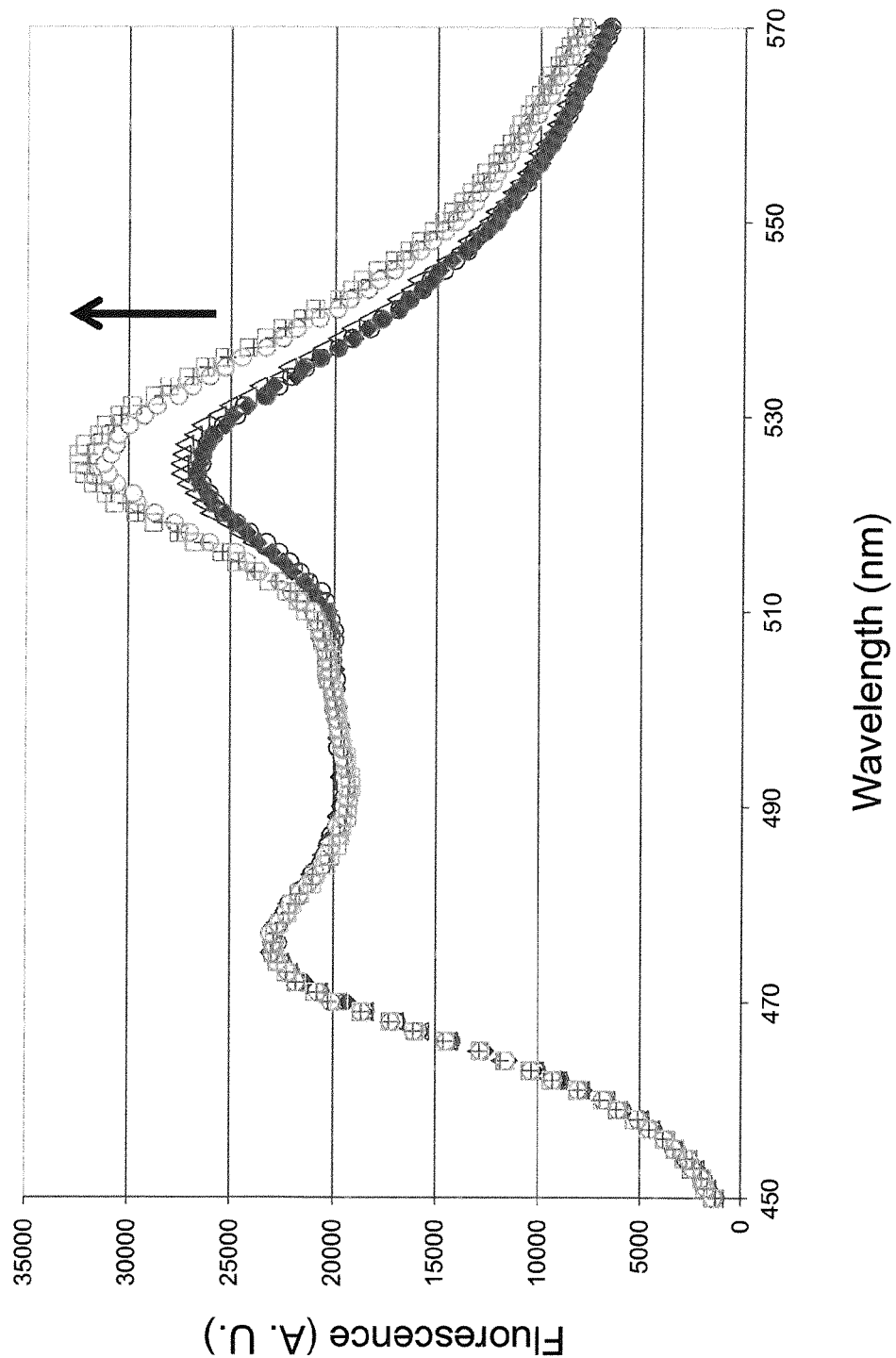
Figure 7:
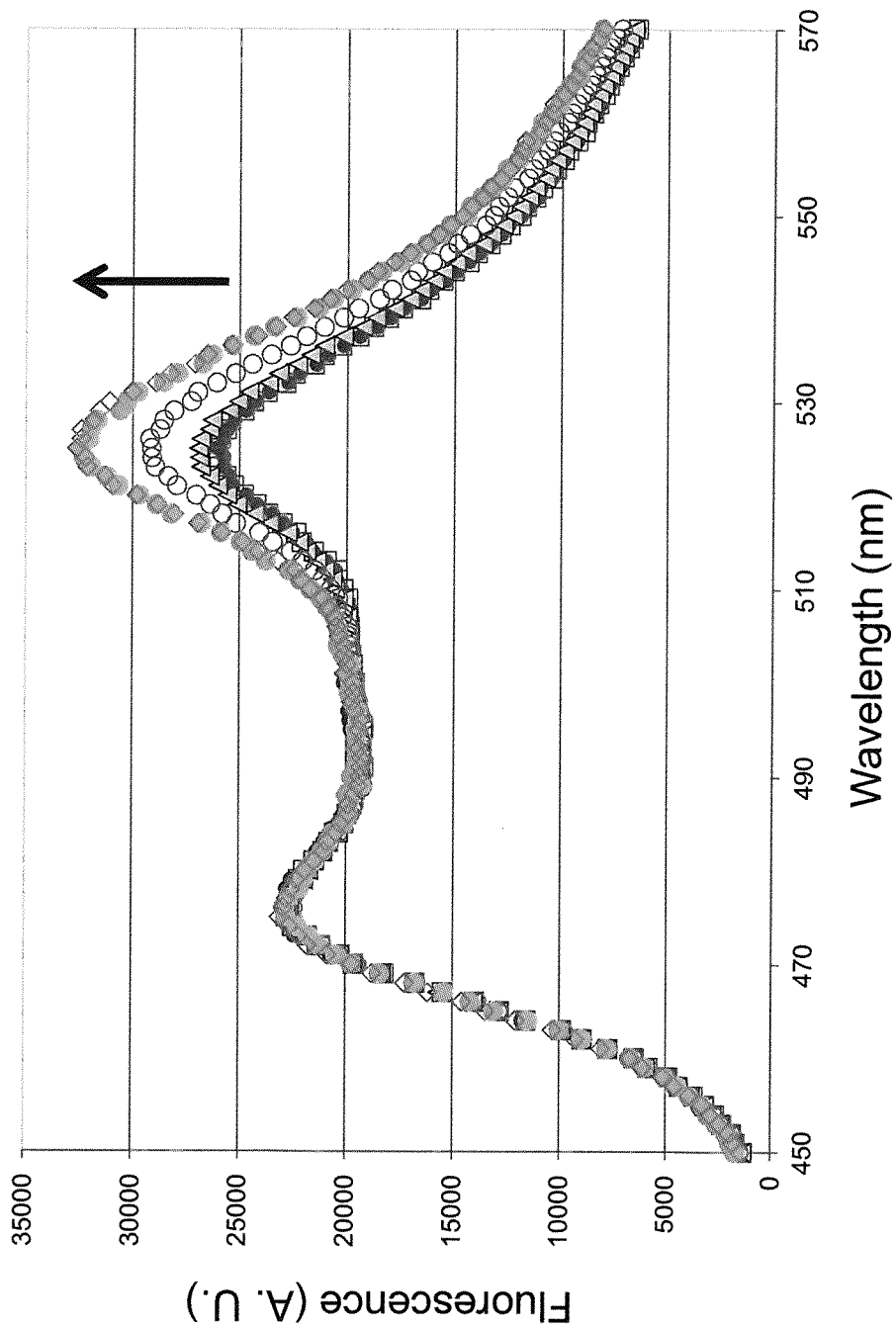

The results obtained with the cameleon biosensor WT protein (FIGS. 6 and 7, the spectra were normalized at 476 nm) show that this biosensor is able to do some FRET in presence of calcium, and that the maximum of FRET is obtained at 8 µM of calcium and above. Similar results are obtained with 8 µM of uranyl nitrate, showing that the cameleon biosensor obtained with the WT calmodulin shows similar sensitivities for calcium and uranyl.

EXAMPLE 3

Uranyl Chelation by CaMΔ Immobilized on a Metallic Surface

This example illustrates the possibility to use peptides derived from calmodulin immobilized on a solid support to chelate uranyl from a solution.

1. Methods

Figure 8:
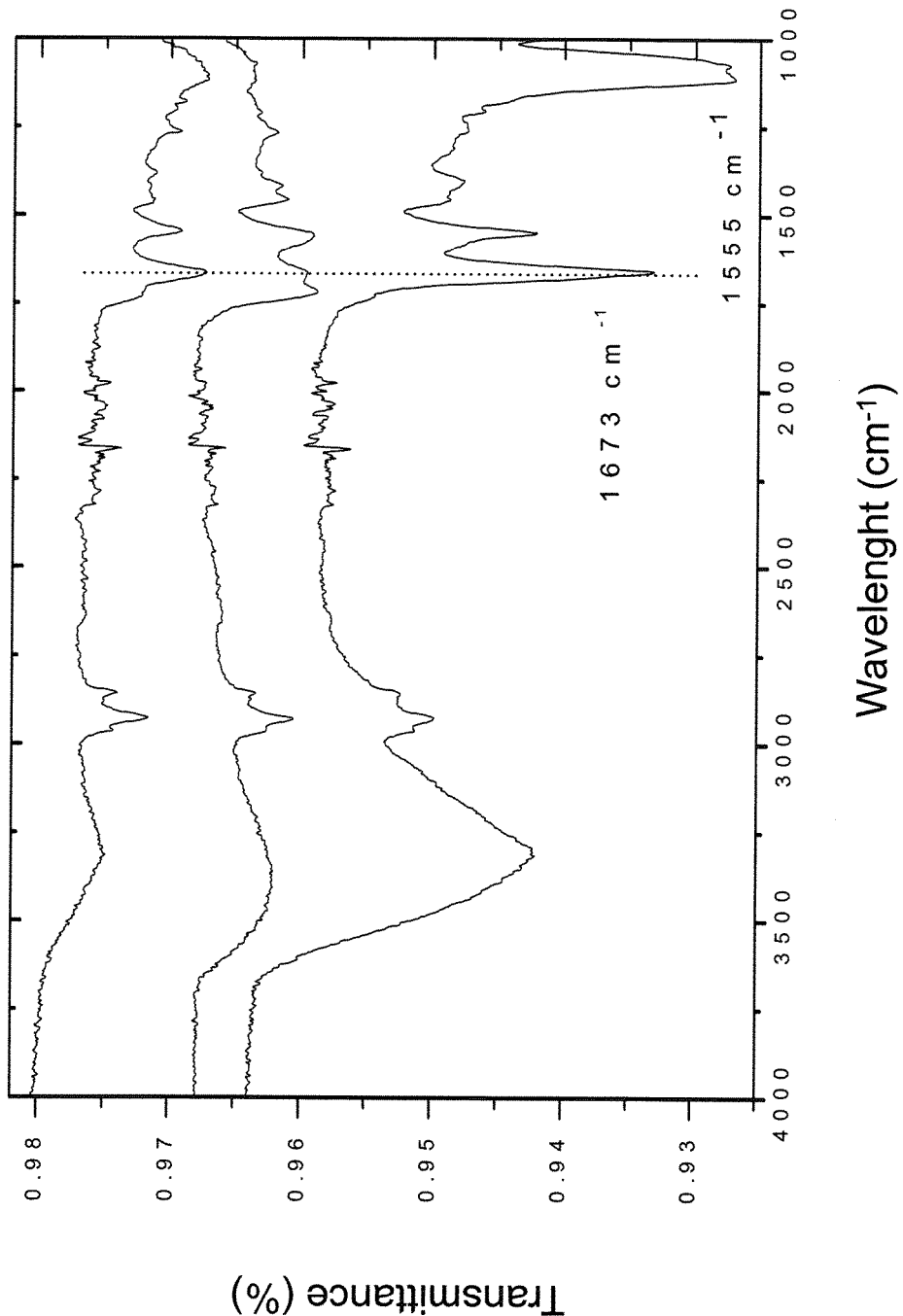
FIG. 8 shows the transmission ATR-FTIR spectra of the gold strip covered with a 5 nm layer of polyacrylic acid and the CaMΔ(upper spectrum), with the polyacrylic acid layer only (middle spectrum) and with a 50 nm layer of polyacrylic acid and the CaMΔ(lower spectrum).

The peptide CaMΔ was grafted on a gold strip surface modified by a 5 to 200 nm thick layer of polyacrylic acid, using activation via succinimide esters. A solution of CaMΔ at 100 g/mL in MES buffer 20 mM was used. Stable grafting of the protein was verified by Fourier transform infrared spectroscopy monitoring of the presence of the two amide I and amide II bands characteristic for proteins (FIG. 8). The protein was grafted on one half of the gold strip, the other half being used as a control area to identify possible non-specific adsorption of uranyl. The interaction with uranyl was performed by a 2 hours dipping in an uranyl chloride solution (in ultrapure water) followed by thorough rinsing with ultrapure water (18 MΩ). X-ray photoelectron spectrometry (XPS) was used to identify the presence of nitrogen and uranyl at the gold strip surface.

2. Results

Figure 9:
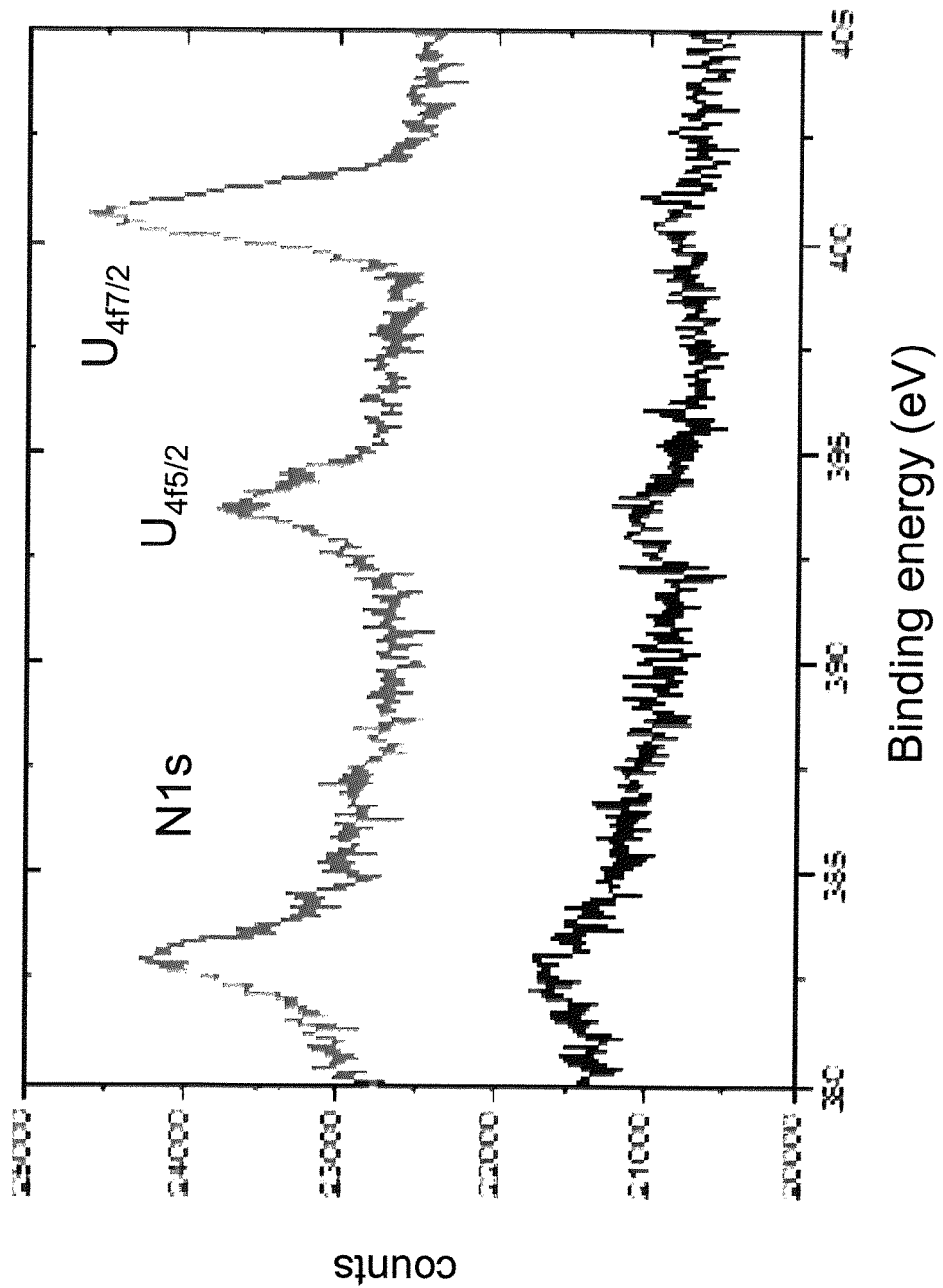
FIG. 9 shows XPS spectra recorded on the grafted gold strip. The upper spectrum is recorded in a spot exposed to the protein and the lower spectrum is recorded on a spot that was not contacted with the protein solution.

FIG. 8 shows the FTIR transmission spectra recorded with the gold strip covered either with the polyacrylic acid alone (middle spectrum) or with protein grafted to polyacrylic acid layers of 5 nm (upper spectrum) and 50 nm (lower spectrum). The bands at 1673 and 1555 cm$^{-1}$ are representative of the presence of the protein. These bands are observed in the upper and lower spectra. They are more intense in the lower spectrum, showing the impact of the polyacrylic layer thickness on the protein load onto the gold strip. These data show that CaMΔ was successfully grafted onto the gold strip. FIG. 9 shows the XPS spectra recorded on the gold strip: the upper spectrum was recorded at a spot containing protein and the lower spectrum was recorded on a spot corresponding to the gold strip without protein. The band at ~382.5 eV corresponds to the presence of nitrogen, while the bands at ~394 eV and 401 eV correspond to the presence of uranium. The presence of uranium is only observed concomitant to the presence of nitrogen (upper spectrum), indicating that uranyl is immobilized by the protein. These results show that specific uranyl adsorption by CaMΔ occurs when CaMΔ is immobilized on a solid metal support. These results show that CaMΔ may be used for uranyl chelation from water, for depollution applications.

TABLE

Amino acid and nucleotide sequences

| | Name | Sequence |
|---|---|---|
| SEQ ID NO: 1 | *Arabidopsis thaliana* CaM3 | ATGGCGGATCAGCTCACCGACGATCAGATCTCTGAGTTTAA GGAAGCTTTCAGCTTATTCGACAAGGATGGTGATGGTTGCA TTACCACCAAGGAGCTGGGTACTGTGATGCGTTCCCTTGGA CAAAACCCAACCGAAGCAGAGCTTCAAGACATGATCAACGA AGTGGATGCTGATGGTAACGGTACCATTGATTTCCCAGAGT TCTTGAACCTTATGGCTCGTAAGATGAAGGACACCGACTCT GAGGAAGAGCTCAAGGAAGCATTCCGGGTTTTCGACAAGGA CCAGAACGGTTTCATCTCAGCAGCTGAGCTCCGCCATGTGA TGACAAACCTTGGCGAGAAGCTTACTGATGAAGAAGTTGAT GAGATGATCAAGGAAGCTGATGTTGATGGTGATGGTCAGAT TAACtACGAAGAGTTTGTTAAGGTCATGATGGCTAAGTGAC T |
| SEQ ID NO: 2 | *Arabidopsis thaliana* CaM3 | MADQLTDDQISEFKEAFSLFDKDGDGCITTKELGTVMRSLG QNFTEAELQDMINEVDADGNGTIDEPEFLNLMARKMKDTDS EEELKEAFRVFDKDQNGFISAAELRHVMTNLGEKLTDEEVD EMIKEADVDGDGQINYEEFVKVMMAK |

TABLE-continued

Amino acid and nucleotide sequences

| Name | Sequence |
|---|---|
| SEQ ID NO: 3 CaM3 EF-hand1 loop | DKDGDGCITTKE |
| SEQ ID NO: 4 CaM3 EF-hand2 loop | DADGNGTIDFPE |
| SEQ ID NO: 5 CaM3 EF-hand3 loop | DKDQNGFISAAE |
| SEQ ID NO: 6 CaM3 EF-hand4 loop | DVDGDGQINYEE |
| SEQ ID NO: 7 EF-hand1 loop ΔK2D3/ΔD1K2 | DGDGCITTKE |
| SEQ ID NO: 8 EF-hand1 loop ΔK2D3/ΔD1K2 + C7Y | DGDGYITTKE |
| SEQ ID NO: 9 EF-hand1 loop ΔK2D3/ΔD1K2 + C7Y + T10A + K11A | DGDGYITAAE |
| SEQ ID NO: 10 EF-hand2 loop ΔA2D3/ΔD1A2 | DGNGTIDFPE |
| SEQ ID NO: 11 EF-hand2 loop ΔA2D3/ΔD1A2 + T7Y | DGNGYIDFPE |
| SEQ ID NO: 12 EF-hand2 loop ΔA2D3/ΔD1A2 + N5D | DGDGTIDFPE |
| SEQ ID NO: 13 EF-hand2 loop ΔA2D3/ΔD1A2 + T7Y + N5D | DGDGYIDFPE |
| SEQ ID NO: 14 EF-hand3 loop ΔK2D3/ΔD1K2 | DQNGFISAAE |
| SEQ ID NO: 15 EF-hand4 loop ΔV2D3/ΔD1V2 | DGDGQINYEE |
| SEQ ID NO: 16 CaMΔ | TCC ATG GCG GAT CAG CTC ACC GAC GAT CAG ATC TCT GAG TTT AAG GAA GCT TTC AGC TTA TTC GAC GGT GAT GGT TaC ATT ACC GCC GCG GAG CTG GGT ACT GTG ATG CGT TCC CTT GGA CAA AAC CCA ACC GAA GCA GAG CTT CAA GAC ATG ATC AAC GAA GTG GcT GCT GcT GGT AAC GGT ACC ATT GAT TTC CCA GAG TTC TTG AAC CTT ATG GCT CGT AAG TGA |
| SEQ ID NO: 17 CaMΔ | SMADQLTDDQISEFKEAFSLEDGDGYITAAELGTVMRSLGQ NPTEAELQDMINEVAAAGNGTIDEPEFLNLMARK |
| SEQ ID NO: 18 Calmodulin variant from Cameleon biosensor Δ | MADQLTDDQISEFKEAFSLEDGDGCITTKELGTVMRSLGQN PTEAELQDMINEVDADGNGTIDEPEFLNLMARKMKDTDSEE ELKEAFRVFDKDQNGFISAAELRHVMTNLGEKLTDEEVDEM IKEADVDGDGQINYEEFVKVMMAK |
| SEQ ID NO: 19 Calmodulin variant from Cameleon biosensor Δ-S2M | MADQLTDDQISEFKEAFSLFDGDGCITTKELGTVMRSLGQN PTEAELQDMINEVAAAGNGTIDEPEFLNLMARKMKDTDSEE ELKEAFRVFDKDQNGFISAAELRHVMTNLGEKLTDEEVDEM IKEADVDGDGQINYEEFVKVMMAK |
| SEQ ID NO: 20 Calmodulin variant (Δ sites 1, 2, 3, 4) | MADQLTDDQISEFKEAFSLFDGDGCITTKELGTVMRSLGQN PTEAELQDMINEVDGNGTIDFPEFLNLMARKMKDTDSEEEL KEAFRVFDQNGFISAAELRHVMTNLGEKLTDEEVDEMIKEA DGDGQINYEEFVKVMMAK |
| SEQ ID NO: 21 M13 | AAACGTCGCTGGCTTTATTGCGGTGAGCGCGGC CAACCGCTTTAAAAAAATTAGCTCGAGCGGCGCGCTG |
| SEQ ID NO: 22 M13 | KRRWKKNFIAVSAANRFKKISSSGAL |
| SEQ ID NO: 23 skMLCK | KRRWKKNFIAVSAANRFKKISSSGA |
| SEQ ID NO: 24 MLCKp | RRKWQKTGHAVRAIGRL |
| SEQ ID NO: 25 smMLCK | ARRKWQKTGHAVRAIGRLSS |

TABLE-continued

Amino acid and nucleotide sequences

| Name | Sequence |
|---|---|
| SEQ ID NO: 26 wasp venom | VNWKKIGQHILSV |
| SEQ ID NO: 27 p21 | KRRQTSMTDFYHSKRRLIFSKRKP |
| SEQ ID NO: 28 melittin | QQRKRKIWSILAPLGTTLVKLVAGIG |
| SEQ ID NO: 29 spectrin | KTASPWKSARLMVTIVATENSIKE |
| SEQ ID NO: 30 CaMKI | AKSKWKQAFNATAVVRHMRKLQ |
| SEQ ID NO: 31 CaMKII | LKKFNARRKLKGAILTTMLATRNFS |
| SEQ ID NO: 32 CaMKK | RFPNGFRKRHGMAKVLILTDLRPIRRV |
| SEQ ID NO: 33 peptidel | LKWKKLLKLLKKLLKLG |
| SEQ ID NO: 34 Cameleon biosensor Δ | TCCATGGTGAGCAAGGGCGAGGAGCTGTTCACCGGGGTGGT GCCCATCCTGGTCGAGCTGGACGGCGACGTAAACGGCCACA GGTTCAGCGTGTCCGGCGAGGGCGAGGGCGATGCCACCTAC GGCAAGCTGACCCTGAAGTTCATCTGCACCACCGGCAAGCT GCCCGTGCCCTGGCCCACCCTCGTGACCACCCTGACCTGGG GCGTGCAGTGCTTCAGCCGCTACCCCGACCACATGAAGCAG CACGACTTCTTCAAGTCCGCCATGCCCGAAGGCTACGTCCA GGAGCGTACCATCTTCTTCAAGGACGACGGCAACTACAAGA CCCGCGCCGAGGTGAAGTTCGAGGGCGACACCCTGGTGAAC CGCATCGAGCTGAAGGGCATCGACTTCAAGGAGGACGGCAA CATCCTGGGGCACAAGCTGGAGTACAACTACATCAGCCACA ACGTCTATATCACCGCCGACAAGCAGAAGAACGGCATCAAG GCCCACTTCAAGATCCGCCACAACATCGAGGACGGCAGCGT GCAGCTCGCCGACCACTACCAGCAGAACACCCCCATCGGCG ACGGCCCCGTGCTGCTGCCCGACAACCACTACCTGAGCACC CAGTCCGCCCTGAGCAAAGACCCCAACGAGAAGCGCGATCA CATGGTCCTGCTGGAGTTCGTGACCGCCGCCGAGCTCATGG CGGATCAGTTGACCGACGATCAGATCTCTGAATTTAAGGAA GCCTTCAGCTTATTCGACGGTGATGGTTGCATTACCACCAA GGAACTGGGTACTGTGATGCGTTCCCTGGGCCAAAACCCGA CCGAAGCAGAGCTGCAAGACATGATCAACGAAGTGGATGCG GATGGTAACGGTACCATTGATTTCCCGGAATTCTTGAACCT GATGGCCCGTAAGATGAAAGACACCGACAGCGAGGAAGAGC TGAAAGAAGCCTTCCGCGTTTTCGACAAAGACCAGAACGGT TTCATCAGCGCAGCGGAACTGCGCCATGTGATGACCAACCT GGGCGAAAAACTGACGGATGAAGAAGTTGATGAGATGATCA AAGAAGCGGATGTGGATGGTGATGGTCAGATTAACTACGAA GAGTTTGTTAAGGTGATGATGGCGAAAGGCGGTGGCGGTAG CAAACGTCGCTGGAAAAAAAACTTTATTGCGGTGAGCGCGG CCAACCGCTTTAAAAAAATTAGCTCGAGCGGCGCGCTGGTC GACATGGTGAGCAAGGGCGAGGAGCTGTTCACCGGGGTGGT GCCCATCCTGGTCGAGCTGGACGGCGACGTAAACGGCCACA AGTTCAGCGTGTCCGGCGAGGGCGAGGGCGATGCCACCTAC GGCAAGCTGACCCTGAAGTTCATCTGCACCACCGGCAAGCT GCCCGTGCCCTGGCCCACCCTCGTGACCACCTTCGGCTACG GCGTGCAGTGCTTCGCCCGCTACCCCGACCACATGAAGCAG CACGACTTCTTCAAGTCCGCCATGCCCGAAGGCTACGTCCA GGAGCGCACCATCTTCTTCAAGGACGACGGCAACTACAAGA CCCGCGCCGAGGTGAAGTTCGAGGGCGACACCCTGGTGAAC CGCATCGAGCTGAAGGGCATCGACTTCAAGGAGGACGGCAA CATCCTGGGGCACAAGCTGGAGTACAACTACAACAGCCACA ACGTCTATATCATGGCCGACAAGCAGAAGAACGGCATCAAG GTGAACTTCAAGATCCGCCACAACATCGAGGACGGCAGCGT GCAGCTCGCCGACCACTACCAGCAGAACACCCCCATCGGCG ACGGCCCCGTGCTGCTGCCCGACAACCACTACCTGAGCTAC CAGTCCGCCCTGAGCAAAGACCCCAACGAGAAGCGCGATCA CATGGTCCTGCTGGAGTTCGTGACCGCCGCCGGGATCACTC TCGGCATGGACGAGCTGTACAAGTAA |
| SEQ ID NO: 35 Cameleon biosensor Δ | SMVSKGEELFTGVVPILVELDGDVNGHRFSVSGEGEGDATY GKLTLKFICTTGKLPVPWPTLVTTLTWGVQCFSRYPDHMKQ HDFFKSAMPEGYVQERTIFFKDDGNYKTRAEVKFEGDTLVN RIELKGIDPKEDGNILGHKLEYNYISHNVYITADKQKNGIK AHFKIRHNIEDGSVQLADHYQQNTPIGDGPVLLPDNHYLST QSALSKDPNEKRDHMVLLEFVTAAELMADQLTDDQISEFKE AFSLEDGDGCITTKELGTVMRSLGQNPTEAELQDMINEVDA DGNGTIDFPEFLNLMARKMKDTDSEEELKEAFRVFDKDQNG FISAAELRHVMTNLGEKLTDEEVDEMIKEADVDGDGQINYE EFVKVMMAKGGGGSKRRWKKNFIAVSAANRFKKISSSGALv dMVSKGEELFTGVVPILVELDGDVNGHKFSVSGEGEGDATY |

TABLE-continued

Amino acid and nucleotide sequences

| Name | Sequence |
|---|---|
| | GKLTLKFICTTGKLPVPWPTLVTTFGYGVQCFARYPDHMKQ<br>HDFFKSAMPEGYVQERTIFFKDDGNYKTRAEVKFEGDTLVN<br>RIELKGIDFKEDGNILGHKLEYNYNSHNVYIMADKQKNGIK<br>VNFKIRHNIEDGSVQLADHYQQNTPIGDGPVLLPDNHYLSY<br>QSALSKDPNEKRDHMVLLEFVTAAGITLGMDELYK |
| SEQ ID NO: 36 Cameleon biosensor Δ-S2M | TCCATGGTGAGCAAGGGCGAGGAGCTGTTCACCGGGGTGGT<br>GCCCATCCTGGTCGAGCTGGACGGCGACGTAAACGGCCACA<br>GGTTCAGCGTGTCCGGCGAGGGCGAGGGCGATGCCACCTAC<br>GGCAAGCTGACCCTGAAGTTCATCTGCACCACCGGCAAGCT<br>GCCCGTGCCCTGGCCCACCCTCGTGACCACCCTGACCTGGG<br>GCGTGCAGTGCTTCAGCCGCTACCCCGACCACATGAAGCAG<br>CACGACTTCTTCAAGTCCGCCATGCCCGAAGGCTACGTCCA<br>GGAGCGCACCATCTTCTTCAAGGACGACGGCAACTACAAGA<br>CCCGCGCCGAGGTGAAGTTCGAGGGCGACACCCTGGTGAAC<br>CGCATCGAGCTGAAGGGCATCGACTTCAAGGAGGACGGCAA<br>CATCCTGGGGCACAAGCTGGAGTACAACTACATCAGCCACA<br>ACGTCTATATCACCGCCGACAAGCAGAAGAACGGCATCAAG<br>GCCCACTTCAAGATCCGCCACAACATCGAGGACGGCAGCGT<br>GCAGCTCGCCGACCACTACCAGCAGAACACCCCCATCGGCG<br>ACGGCCCCGTGCTGCTGCCCGACAACCACTACCTGAGCACC<br>CAGTCCGCCCTGAGCAAAGACCCCAACGAGAAGCGCGATCA<br>CATGGTCCTGCTGGAGTTCGTGACCGCCGCCGAGCTCATGG<br>CGGATCAGTTGACCGACGATCAGATCTCTGAATTTAAGGAA<br>GCCTTCAGCTTATTCGACGGTGATGGTTGCATTACCACCAA<br>GGAACTGGGTACTGTGATGCGTTCCCTGGGCCAAAACCCGA<br>CCGAAGCAGAGCTGCAAGACATGATCAACGAAGTGGCTGCG<br>GCTGGTAACGGTACCATTGATTTCCCGGAATTCTTGAACCT<br>GATGGCCCGTAAGATGAAAGACACCGACAGCGAGGAAGAGC<br>TGAAAGAAGCCTTCCGCGTTTTCGACAAAGACCAGAACGGT<br>TTCATCAGCGCAGCGGAACTGCGCCATGTGATGACCAACCT<br>GGGCGAAAAACTGACGGATGAAGAAGTTGATGAGATGATCA<br>AAGAAGCGGATGTGGATGGTGATGGTCAGATTAACTACGAA<br>GAGTTTGTTAAGGTGATGATGGCGAAAGGCGGTGGCGGTAG<br>CAAACGTCGCTGGAAAAAAAACTTTATTGCGGTGAGCGCGG<br>CCAACCGCTTTAAAAAAATTAGCTCGAGCGGCGCGCTGGTC<br>GACATGGTGAGCAAGGGCGAGGAGCTGTTCACCGGGGTGGT<br>GCCCATCCTGGTCGAGCTGGACGGCGACGTAAACGGCCACA<br>AGTTCAGCGTGTCGGCGAGGGCGAGGGCGATGCCACCTAC<br>GGCAAGCTGACCCTGAAGTTCATCTGCACCACCGGCAAGCT<br>GCCCGTGCCCTGGCCCACCCTCGTGACCACCTTCGGCTACG<br>GCGTGCAGTGCTTCGCCCGCTACCCCGACCACATGAAGCAG<br>CACGACTTCTTCAAGTCCGCCATGCCCGAAGGCTACGTCCA<br>GGAGCGCACCATCTTCTTCAAGGACGACGGCAACTACAAGA<br>CCCGCGCCGAGGTGAAGTTCGAGGGCGACACCCTGGTGAAC<br>CGCATCGAGCTGAAGGGCATCGACTTCAAGGAGGACGGCAA<br>CATCCTGGGGCACAAGCTGGAGTACAACTACAACAGCCACA<br>ACGTCTATATCATGGCCGACAAGCAGAAGAACGGCATCAAG<br>GTGAACTTCAAGATCCGCCACAACATCGAGGACGGCAGCGT<br>GCAGCTCGCCGACCACTACCAGCAGAACACCCCCATCGGCG<br>ACGGCCCCGTGCTGCTGCCCGACAACCACTACCTGAGCTAC<br>CAGTCCGCCCTGAGCAAAGACCCCAACGAGAAGCGCGATCA<br>CATGGTCCTGCTGGAGTTCGTGACCGCCGCCGGGATCACTC<br>TCGGCATGGACGAGCTGTACAAGTAA |
| SEQ ID NO: 37 Cameleon biosensor Δ-S2M | SMVSKGEELFTGVVPILVELDGDVNGHRFSVSGEGEGDATY<br>GKLTLKFICTTGKLPVPWPTLVTTLTWGVQCFSRYPDHMKQ<br>HDFFKSAMPEGYVQERTIFFKDDGNYKTRAEVKFEGDTLVN<br>RIELKGIDFKEDGNILGHKLEYNYISHNVYITADKQKNGIK<br>AHFKIRHNIEDGSVQLADHYQQNTPIGDGPVLLPDNHYLST<br>QSALSKDPNEKRDHMVLLEFVTAAELMADQLTDDQISEFKE<br>AFSLFDGDGCITTKELGTVMRSLGQNPTEAELQDMINEVAA<br>AGNGTIDEPEFLNLMARKMKDTDSEEELKEAFRVEDKDQNG<br>FISAAELRHVMTNLGEKLTDEEVDEMIKEADVDGDGQINYE<br>EFVKVMMAKGGGGSKRRWKKNFIAVSAANRFKKISSSGALv<br>dMVSKGEELFTGVVPILVELDGDVNGHKESVSGEGEGDATY<br>GKLTLKFICTTGKLPVPWPTLVTTFGYGVQCFARYPDHMKQ<br>HDFFKSAMPEGYVQERTIFFKDDGNYKTRAEVKFEGDTLVN<br>RIELKGIDFKEDGNILGHKLEYNYNSHNVYIMADKQKNGIK<br>VNFKIRHNIEDGSVQLADHYQQNTPIGDGPVLLPDNHYLSY<br>QSALSKDPNEKRDHMVLLEFVTAAGITLGMDELYK |
| SEQ ID NO: 38 Cameleon biosensor ΔΔΔΔ | SMVSKGEELFTGVVPILVELDGDVNGHRFSVSGEGEGDATY<br>GKLTLKFICTTGKLPVPWPTLVTTLTWGVQCFSRYPDHMKQ<br>HDFFKSAMPEGYVQERTIFFKDDGNYKTRAEVKFEGDTLVN<br>RIELKGIDFKEDGNILGHKLEYNYISHNVYITADKQKNGIK |

TABLE-continued

Amino acid and nucleotide sequences

| Name | Sequence |
|---|---|
| | AHFKIRHNIEDGSVQLADHYQQNTPIGDGPVLLPDNHYLST QSALSKDPNEKRDHMVLLEFVTAAELMADQLTDDQISEFKE AFSLEDGDGCITTKELGTVMRSLGQNPTEAELQDMINEVDG NGTIDEPEFLNLMARKMKDTDSEEELKEAFRVEDQNGFISA AELRHVMTNLGEKLTDEEVDEMIKEADGDGQINYEEFVKVM MAKGGGGSKRRWKKNFIAVSAANRFKKISSSGALvdMVSKG EELFTGVVPILVELDGDVNGHKFSVSGEGEGDATYGKLTLK FICTTGKLPVPWPTLVTTEGYGVQCFARYPDHMKQHDFFKS AMPEGYVQERTIFFKDDGNYKTRAEVKFEGDTLVNRIELKG IDFKEDGNILGHKLEYNYNSHNVYIMADKQKNGIKVNFKIR HNIEDGSVQLADHYQQNTPIGDGPVLLPDNHYLSYQSALSK DPNEKRDHMVLLEFVTAAGITLGMDELYK |
| SEQ ID NO: 39 CaM1 | TCC ATG GCG GAT CAG CTC ACC GAC GAT CAG ATC TCT GAG TTT AAG GAA GCT TTC AGC TTA TTC GAC AAG GAT GGT GAT GGT TaC ATT ACC GCC GCG GAG CTG GGT ACT GTG ATG CGT TCC CTT GGA CAA AAC CCA ACC GAA GCA GAG CTT CAA GAC ATG ATC AAC GAA GTG GcT GCT GcT GGT AAC GGT ACC ATT GAT TTC CCA GAG TTC TTG AAC CTT ATG GCT CGT AAG TGA |
| SEQ ID NO: 40 CaM1 | SMADQLTDDQISEFKEAFSLFDKDGDGYITAAELGTVMRSL GQNPTEAELQDMINEVAAAGNGTIDFPEFLNLMARK |
| SEQ ID NO: 41 Primer DGD S | GAAGCTTTCAGCTTATTCGACGGTGATGGTTACATTACCGC CGCG |
| SEQ ID NO: 42 Primer DGD AS | CGCGGCGGTAATCTAACCATCACCGTCGAATAAGCTGAAAG CTTC |
| SEQ ID NO: 43 Primer S-TEV-eCFP-BamHI | GAGA GGATCC GAG AAC CTG TAC TTC CAG TCC ATG GTG AGC AAG GGC GAG GAG |
| SEQ ID NO: 44 Primer AS-eCFP-SacI | TAAA GAGCTC GGCGGCGGTCACGAACTCCAGCA |
| SEQ ID NO: 45 Primer S-eYFP-SalI | TATA GTCGAC ATG GTG AGC AAG GGC GAG GAG |
| SEQ ID NO: 46 Primer AS-eYFP-HindIII | GGGC AAGCTT TTA CTT GTA CAG CTC GTC CAT GCC G |
| SEQ ID NO: 47 Cameleon biosensor WT | TCCATGGTGAGCAAGGGCGAGGAGCTGTTCACCGGGGTGGT GCCCATCCTGGTCGAGCTGGACGGCGACGTAAACGGCCACA GGTTCAGCGTGTCCGGCGAGGGCGAGGGCGATGCCACCTAC GGCAAGCTGACCCTGAAGTTCATCTGCACCACCGGCAAGCT GCCCGTGCCCTGGCCCACCCTCGTGACCACCCTGACCTGGG GCGTGCAGTGCTTCAGCCGCTACCCCGACCACATGAAGCAG CACGACTTCTTCAAGTCCGCCATGCCCGAAGGCTACGTCCA GGAGCGTACCATCTTCTTCAAGGACGACGGCAACTACAAGA CCCGCGCCGAGGTGAAGTTCGAGGGCGACACCCTGGTGAAC CGCATCGAGCTGAAGGGCATCGACTTCAAGGAGGACGGCAA CATCCTGGGGCACAAGCTGGAGTACAACTACATCAGCCACA ACGTCTATATCACCGCCGACAAGCAGAAGAACGGCATCAAG GCCCACTTCAAGATCCGCCACAACATCGAGGACGGCAGCGT GCAGCTCGCCGACCACTACCAGCAGAACACCCCCATCGGCG ACGGCCCCGTGCTGCTGCCCGACAACCACTACCTGAGCACC CAGTCCGCCCTGAGCAAAGACCCCAACGAGAAGCGCGATCA CATGGTCCTGCTGGAGTTCGTGACCGCCGCCGAGCTCATGG CGGATCAGTTGACCGACGATCAGATCTCTGAATTTAAGGAA GCCTTCAGCTTATTCGACAAAGATGGTGATGGTTGCATTAC CACCAAGGAACTGGGTACTGTGATGCGTTCCCTGGGCCAAA ACCCGACCGAAGCAGAGCTGCAAGACATGATCAACGAAGTG GATGCGGATGGTAACGGTACCATTGATTTCCCCGGAATTCTT GAACCTGATGGCCCGTAAGATGAAAGACACCGACAGCGAGG AAGACCTGAAACAAGCCTTCCGCGTTTTCGACAAAGACCAG AACGGTTTCATCAGCGCAGCGGAACTGCGCCATGTGATGAC CAACCTGGGCGAAAAACTGACGGATGAAGAAGTTGATGAGA TGATCAAAGAAGCGGATGTGGATGGTGATGGTCAGATTAAC TACGAAGAGTTTGTTAAGGTGATGATGGCGAAAGGCGGTGG CGGTAGCAAACGTCGCTGGAAAAAAAACTTTATTGCGGTGA GCGCGGCCAACCGCTTTAAAAAAATTAGCTCGAGCGGCGCG CTGGTCGACATGGTGAGCAAGGGCGAGGAGCTGTTCACCGG GGTGGTGCCCATCCTGGTCGAGCTGGACGGCGACGTAAACG GCCACAAGTTCAGCGTGTCCGGCGAGGGCGAGGGCGATGCC |

TABLE-continued

Amino acid and nucleotide sequences

| Name | Sequence |
|---|---|
| | ACCTACGGCAAGCTGACCCTGAAGTTCATCTGCACCACCGG |
| | CAAGCTGCCCGTGCCCTGGCCCACCCTCGTGACCACCTTCG |
| | GCTACGGCGTGCAGTGCTTCGCCCGCTACCCCGACCACATG |
| | AAGCAGCACGACTTCTTCAAGTCCGCCATGCCCGAAGGCTA |
| | CGTCCAGGAGCGCACCATCTTCTTCAAGGACGACGGCAACT |
| | ACAAGACCCGCGCCGAGGTGAAGTTCGAGGGCGACACCCTG |
| | GTGAACCGCATCGAGCTGAAGGGCATCGACTTCAAGGAGGA |
| | CGGCAACATCCTGGGGCACAAGCTGGAGTACAACTACAACA |
| | GCCACAACGTCTATATCATGGCCGACAAGCAGAAGAACGGC |
| | ATCAAGGTGAACTTCAAGATCCGCCACAACATCGAGGACGG |
| | CAGCGTGCAGCTCGCCGACCACTACCAGCAGAACACCCCCA |
| | TCGGCGACGGCCCCGTGCTGCTGCCCGACAACCACTACCTG |
| | AGCTACCAGTCCGCCCTGAGCAAAGACCCCAACGAGAAGCG |
| | CGATCACATGGTCCTGCTGGAGTTCGTGACCGCCGCCGGGA |
| | TCACTCTCGGCATGGACGAGCTGTACAAGTAA |
| SEQ ID NO: 48 Cameleon biosensor WT | SMVSKGEELFTGVVPILVELDGDVNGHRFSVSGEGEGDATY GKLTLKFICTTGKLPVPWPTLVTTLTWGVQCFSRYTDHMKQ HDFFKSAMPEGYVQERTIFFKDDGNYKTRAEVKFEGDTLVN RIELKGIDEKEDGNILGHKLEYNYISHNVYITADKQKNGIK AHEKIRHNIEDGSVQLADHYQQNTPIGDGPVLLPDNHYLST QSALSKDPNEKRDHMVLLEFVTAAELMADQLTDDQISEFKE AFSLFDKDGDGCITTKELGTVMRSLGQNPTEAELQDMINEV DADGNGTIDEPEFLNLMARKMKDTDSEEELKEAFRVEDKDQ NGFISAAELRHVMTNLGEKLTDEEVDEMIKEADVDGDGQIN YEEFVKVMMAKGGGGSKRRWKKNFIAVSAANRFKKISSSGA LvdMVSKGEELFTGVVPILVELDGDVNGHKESVSGEGEGDA TYGKLTLKFICTTGKLPVPWPTLVTTEGYGVQCFARYPDHM KQHDFFKSAMPEGYVQERTIFFKDDGNYKTRAEVKFEGDTL VNRIELKGIDFKEDGNILGHKLEYNYNSHNVYIMADKQKNG IKVNFKIRHNIEDGSVQLADHYQQNTPIGDGPVLLPDNHYL SYQSALSKDPNEKRDHMVLLEFVTAAGITLGMDYK |
| SEQ ID NO: 49 Primer S-Δ | GGAAGCCTTCAGCTTATTCGACGGTGATGGTTGCATTACC |
| SEQ ID NO: 50 Primer AS-Δ | GGTAATGCAACCATCACCGTCGAATAAGCTGAAGGCTTCC |
| SEQ ID NO: 51 Primer S-S2M | GGT ACC GTT ACC AGC AGC AGC CAC TTC GTT GAT C |
| SEQ ID NO: 52 Primer AS-S2M | GAT CAA CGA AGT GGC TGC TGC TGG TAA CGG TAC C |
| SEQ ID NO: 53 Cameleon biosensor WT-S2M | TCCATGGTGAGCAAGGGCGAGGAGCTGTTCACCGGGGTGGT GCCCATCCTGGTCGAGCTGGACGGCGACGTAAACGGCCACA GGTTCAGCGTGTCCGGCGAGGGCGAGGGCGATGCCACCTAC GGCAAGCTGACCCTGAAGTTCATCTGCACCACCGGCAAGCT GCCCGTGCCCTGGCCCACCCTCGTGACCACCCTGACCTGGG GCGTGCAGTGCTTCAGCCGCTACCCCGACCACATGAAGCAG CACGACTTCTTCAAGTCCGCCATGCCCGAAGGCTACGTCCA GGAGCGTACCATCTTCTTCAAGGACGACGGCAACTACAAGA CCCGCGCCGAGGTGAAGTTCGAGGGCGACACCCTGGTGAAC CGCATCGAGCTGAAGGGCATCGACTTCAAGGAGGACGGCAA CATCCTGGGGCACAAGCTGGAGTACAACTACATCAGCCACA ACGTCTATATCACCGCCGACAAGCAGAAGAACGGCATCAAG GCCCACTTCAAGATCCGCCACAACATCGAGGACGGCAGCGT GCAGCTCGCCGACCACTACCAGCAGAACACCCCCATCGGCG ACGGCCCCGTGCTGCTGCCCGACAACCACTACCTGAGCACC CAGTCCGCCCTGAGCAAAGACCCCAACGAGAAGCGCGATCA CATGGTCCTGCTGGAGTTCGTGACCGCCGCCGAGCTCATGG CGGATCAGTTGACCGACGATCAGATCTCTGAATTTAAGGAA GCCTTCAGCTTATTCGACAAAGATGGTGATGGTTGCATTAC CACCAAGGAACTGGGTACTGTGATGCGTTCCCTGGGCCAAA ACCCGACCGAAGCAGAGCTGCAAGACATGATCAACGAAGTG GCTGCGGCTGGTAACGGTACCATTGATTTCCCGGAATTCTT GAACCTGATGGCCCGTAAGATGAAAGACACCGACAGCGAGG AAGAGCTGAAAGAAGCCTTCCGCGTTTTCGACAAAGACCAG AACGGTTTCATCAGCGCAGCGGAACTGCGCCATGTGATGAC CAACCTGGGCGAAAAACTGACGGATGAAGAAGTTGATGAGA TGATCAAAGAAGCGGATGTGGATGGTGATGGTCAGATTAAC TACGAAGAGTTTGTTAAGGTGATGATGGCGAAAGGCGGTGG CGGTAGCAAACGTCGCTGGAAAAAAAACTTTATTGCGGTGA GCGCGGCCAACCGCTTTAAAAAAATTAGCTCGAGCGGCGCG CTGGTCGACATGGTGAGCAAGGGCGAGGAGCTGTTCACCGG GGTGGTGCCCATCCTGGTCGAGCTGGACGGCGACGTAAACG GCCACAAGTTCAGCGTGTCCGGCGAGGGCGAGGGCGATGCC |

TABLE-continued

Amino acid and nucleotide sequences

| Name | Sequence |
|---|---|
| | ACCTACGGCAAGCTGACCCTGAAGTTCATCTGCACCACCGG<br>CAAGCTGCCCGTGCCCTGGCCCACCCTCGTGACCACCTTCG<br>GCTACGGCGTGCAGTGCTTCGCCCGCTACCCCGACCACATG<br>AAGCAGCACGACTTCTTCAAGTCCGCCATGCCCGAAGGCTA<br>CGTCCAGGAGCGCACCATCTTCTTCAAGGACGACGGCAACT<br>ACAAGACCCGCGCCGAGGTGAAGTTCGAGGGCGACACCCTG<br>GTGAACCGCATCGAGCTGAAGGGCATCGACTTCAAGGAGGA<br>CGGCAACATCCTGGGGCACAAGCTGGAGTACAACTACAACA<br>GCCACAACGTCTATATCATGGCCGACAAGCAGAAGAACGGC<br>ATCAAGGTGAACTTCAAGATCCGCCACAACATCGAGGACGG<br>CAGCGTGCAGCTCGCCGACCACTACCAGCAGAACACCCCCA<br>TCGGCGACGGCCCCGTGCTGCTGCCCGACAACCACTACCTG<br>AGCTACCAGTCCGCCCTGAGCAAAGACCCCAACGAGAAGCG<br>CGATCACATGGTCCTGCTGGAGTTCGTGACCGCCGCCGGGA<br>TCACTCTCGGCATGGACGAGCTGTACAAGTAA |
| SEQ ID NO: 54 Cameleon biosensor WT-S2M | SMVSKGEELFTGVVPILVELDGDVNGHRFSVSGEGEGDATY<br>GKLTLKFICTTGKLPVPWPTLVTTLTWGVQCFSRYPDHMKQ<br>HDFFKSAMPEGYVQERTIFFKDDGNYKTRAEVKFEGDTLVN<br>RIELKGIDFKEDGNILGHKLEYNYISHNVYITADKQKNGIK<br>AHFKIRHNIEDGSVQLADHYQQNTPIGDGPVLLPDNHYLST<br>QSALSKDPNEKRDHMVLLEFVTAAELMADQLTDDQISEFKE<br>AFSLFDKDGDGCITTKELGTVMRSLGQNPTEAELQDMINEV<br>AAAGNGTIDEPEFLNLMARKMKDTDSEEELKEAFRVEDKDQ<br>NGFISAAELRHVMTNLGEKLTDEEVDEMIKEADVDGDGQIN<br>YEEFVKVMMAKGGGGSKRRWKKNFIAVSAANRFKKISSSGA<br>LvdMVSKGEELFTGVVPILVELDGDVNGHKESVSGEGEGDA<br>TYGKLTLKFICTTGKLPVPWPTLVTTEGYGVQCFARYPDHM<br>KQHDFFKSAMPEGYVQERTIFFKDDGNYKTRAEVKFEGDTL<br>VNRIELKGIDEKEDGNILGHKLEYNYNSHNVYTMADKQKNG<br>IKVNFKIRHNIEDGSVQLADHYQQNTPIGDGPVLLFTNHYL<br>SYQSALSKDPNEKRDHMVLLEFVTAAGITLGMDELYK |
| SEQ ID NO: 55 CaMΔ3 | TCC ATG GCG GAT CAG CTC ACC GAC GAT CAG<br>ATC TCT GAG TTT AAG GAA GCT TTC AGC TTA<br>TTC GAC AAG GGT GAT GGT TaC ATT ACC GCC<br>GCG GAG CTG GGT ACT GTG ATG CGT TCC CTT<br>GGA CAA AAC CCA ACC GAA GCA GAG CTT CAA<br>GAC ATG ATC AAC GAA GTG GcT GCT GcT GGT<br>AAC GGT ACC ATT GAT TTC CCA GAG TTC TTG<br>AAC CTT ATG GCT CGT AAG TGA |
| SEQ ID NO: 56 CaMΔ3 | SMADQLTDDQISEFKEAFSLFDKGDGYITAAELGTVMRSLG<br>QNPTEAELQDMINEVAAAGNGTIDEPEFLNLMARK |
| SEQ ID NO: 57 Primer S-Δ3Y | TTCAGCTTATTCGACAAGGGTGATGGTTACATTACC |
| SEQ ID NO: 58 Primer AS-Δ3Y | GGTAATGTAACCATCACCCTTGTCGAATAAGCTGAA |
| SEQ ID NO: 59 CaMΔ-WT | TCC ATG GCG GAT CAG CTC ACC GAC GAT CAG<br>ATC TCT GAG TTT AAG GAA GCT TTC AGC TTA<br>TTC GAC GGT GAT GGT TaC ATT ACC ACC AAG<br>GAG CTG GGT ACT GTG ATG CGT TCC CTT GGA<br>CAA AAC CCA ACC GAA GCA GAG CTT CAA GAC<br>ATG ATC AAC GAA GTG GcT GCT GcT GGT AAC<br>GGT ACC ATT GAT TTC CCA GAG TTC TTG AAC<br>CTT ATG GCT CGT AAG TGA |
| SEQ ID NO: 60 CaMΔ-WT | SMADQLTDDQISEFKEAFSLFDGDGYITTKELGTVMRSLGQ<br>NPTEAELQDMINEVAAAGNGTIDEPEFLNLMARK |
| SEQ ID NO: 61 Cameleon Biosensor Δ1 Δ3 | SMVSKGEELFTGVVPILVELDGDVNGHRFSVSGEGEGDATY<br>GKLTLKFICTTGKLPVPWPTLVTTLTWGVQCFSRYPDHMKQ<br>HDFFKSAMPEGYVQERTIFFKDDGNYKTRAEVKFEGDTLVN<br>RIELKGIDFKEDGNILGHKLEYNYISHNVYITADKQKNGIK<br>AHFKIRHNIEDGSVQLADHYQQNTPIGDGPVLLPDNHYLST<br>QSALSKDPNEKRDHMVLLEFVTAAelMADQLTDDQISEFKE<br>AFSLEDGDGCITTKELGTVMRSLGQNPTEAELQDMINEVDA<br>DGNGTIDEPEFLNLMARKMKDTDSEEELKEAFRVEDQNGFI<br>SAAELRHVMTNLGEKLTDEEVDEMIKEADVDGDGQINYEEF<br>VKVMMAKGGGGSKRRWKKNFIAVSAANRFKKISSSGALvdM<br>VSKGEELFTGVVPILVELDGDVNGHKESVSGEGEGDATYGK<br>LTLKFICTTGKLPVPWPTLVTTEGYGVQCFARYPDHMKQHD<br>FFKSAMPEGYVQERTIFFKDDGNYKTRAEVKFEGDTLVNRI |

TABLE-continued

Amino acid and nucleotide sequences

| Name | Sequence |
|---|---|
| | ELKGIDFKEDGNILGHKLEYNYNSHNVYIMADKQKNGIKVN<br>FKIRHNIEDGSVQLADHYQQNTPIGDGPVLLPDNHYLSYQS<br>ALSKDPNEKRDBMVLLEFVTAAGITLGMDELYK |
| SEQ ID NO: 62 Cameleon Biosensor Δ1 Δ3 | TCCATGGTGAGCAAGGGCGAGGAGCTGTTCACCGGGGTGGT<br>GCCCATCCTGGTCGAGCTGGACGGCGACGTAAACGGCCACA<br>GGTTCAGCGTGTCCGGCGAGGGCGAGGGCGATGCCACCTAC<br>GGCAAGCTGACCCTGAAGTTCATCTGCACCACCGGCAAGCT<br>GCCCGTGCCCTGGCCCACCCTCGTGACCACCCTGACCTGG<br>GCGTGCAGTGCTTCAGCCGCTACCCCGACCACATGAAGCAG<br>CACGACTTCTTCAAGTCCGCCATGCCCGAAGGCTACGTCCA<br>GGAGCGTACCATCTTCTTCAAGGACGACGGCAACTACAAGA<br>CCCGCGCCGAGGTGAAGTTCGAGGGCGACACCCTGGTGAAC<br>CGCATCGAGCTGAAGGGCATCGACTTCAAGGAGGACGGCAA<br>CATCCTGGGGCACAAGCTGGAGTACAACTACATCAGCCACA<br>ACGTCTATATCACCGCCGACAAGCAGAAGAACGGCATCAAG<br>GCCCACTTCAAGATCCGCCACAACATCGAGGACGGCAGCGT<br>GCAGCTCGCCGACCACTACCAGCAGAACACCCCCATCGGCG<br>ACGGCCCCGTGCTGCTGCCCGACAACCACTACCTGAGCACC<br>CAGTCCGCCCTGAGCAAAGACCCCAACGAGAAGCGCGATCA<br>CATGGTCCTGCTGGAGTTCGTGACCGCCGCCGAGCTCATGG<br>CGGATCAGTTGACCGACGATCAGATCTCTGAATTTAAGGAA<br>GCCTTCAGCTTATTCGACGGTGATGGTTGCATTACCACCAA<br>GGAACTGGGTACTGTGATGCGTTCCCTGGGCCAAAACCCGA<br>CCGAAGCAGAGCTGCAAGACATGATCAACGAAGTGGATGCG<br>GATGGTAACGGTACCATTGATTTCCCGGAATTCTTGAACCT<br>GATGGCCCGTAAGATGAAAGACACCGACAGCGAGGAAGAGC<br>TGAAAGAAGCCTTCCGCGTTTTCGACCAGAACGGTTTCATC<br>AGCGCAGCGGAACTGCGCCATGTGATGACCAACCTGGGCGA<br>AAAACTGACGGATGAAGAAGTTGATGAGATGATCAAAGAAG<br>CGGATGTGGATGGTGATGGTCAGATTAACTACGAAGAGTTT<br>GTTAAGGTGATGATGGCGAAAGGCGGTGGCGGTAGCAAACG<br>TCGCTGGAAAAAAAACTTTATTGCGGTGAGCGCGGCCAACC<br>GCTTTAAAAAAATTAGCTCGAGCGGCGCGCTGGTCGACATG<br>GTGAGCAAGGGCGAGGAGCTGTTCACCGGGGTGGTGCCCAT<br>CCTGGTCGAGCTGGACGGCGACGTAAACGGCCACAAGTTCA<br>GCGTGTCCGGCGAGGGCGAGGGCGATGCCACCTACGGCAAG<br>CTGACCCTGAAGTTCATCTGCACCACCGGCAAGCTGCCCGT<br>GCCCTGGCCCACCCTCGTGACCACCTTCGGCTACGGCGTGC<br>AGTGCTTCGCCCGCTACCCCGACCACATGAAGCAGCACGAC<br>TTCTTCAAGTCCGCCATGCCCGAAGGCTACGTCCAGGAGCG<br>CACCATCTTCTTCAAGGACGACGGCAACTACAAGACCCGCG<br>CCGAGGTGAAGTTCGAGGGCGACACCCTGGTGAACCGCATC<br>GAGCTGAAGGGCATCGACTTCAAGGAGGACGGCAACATCCT<br>GGGGCACAAGCTGGAGTACAACTACAACAGCCACAACGTCT<br>ATATCATGGCCGACAAGCAGAAGAACGGCATCAAGGTGAAC<br>TTCAAGATCCGCCACAACATCGAGGACGGCAGCGTGCAGCT<br>CGCCGACCACTACCAGCAGAACACCCCCATCGGCGACGGCC<br>CCGTGCTGCTGCCCGACAACCACTACCTGAGCTACCAGTCC<br>GCCCTGAGCAAAGACCCCAACGAGAAGCGCGATCACATGGT<br>CCTGCTGGAGTTCGTGACCGCCGCCGGGATCACTCTCGGCA<br>TGGACGAGCTGTACAAGTAA |
| SEQ ID NO: 63 Cameleon Biosensor Δ1 Δ2 Δ3 | SMVSKGEELFTGVVPILVELDGDVNGHRFSVSGEGEGDATY<br>GKLTLKFICTTGKLPVPWPTLVTTLTWGVQCFSRYPDHMKQ<br>HDFFKSAMPEGYVQERTIFFKDDGNYKTRAEVKFEGDTLVN<br>RIELKGIDFKEDGNILGHKLEYNYISHNVYITADKQKNGIK<br>AHFKIRHNIEDGSVQLADHYQQNTPIGDGPVLLFTNHYLST<br>QSALSKDPNEKRDHMVLLEFVTAAelMADQLTDDQISEFKE<br>AFSLFDGDGCITTKELGTVMRSLGQNPTEAELQDMINEVDG<br>NGTIDFPEFLNLMARKMKDTDSEEELKEAFRVFDQNGFISA<br>AELRHVMTNLGEKLTDEEVDEMIKEADVDGDGQINYEEFVK<br>VMMAKGGGGSKRRWKKNFIAVSAANRFKKISSSGALvdMVS<br>KGEELFTGVVPILVELDGDVNGHKFSVSGEGEGDATYGKLT<br>LKFICTTGKLPVPWPTLVTTEGYGVQCFARYPDHMKQHDFF<br>KSAMPEGYVQERTIFFKDDGNYKTRAEVKFEGDTLVNRIEL<br>KGIDEKEDGNILGHKLEYNYNSHNVYIMADKQKNGIKVNEK<br>IRHNIEDGSVQLADHYQQNTPIGDGPVLLPDNHYLSYQSAL<br>SKDPNEKRDHMVLLEFVTAAGITLGMDELYK |
| SEQ ID NO: 64 Cameleon Biosensor Δ1 Δ2 Δ3 | TCCATGGTGAGCAAGGGCGAGGAGCTGTTCACCGGGGTGGT<br>GCCCATCCTGGTCGAGCTGGACGGCGACGTAAACGGCCACA<br>GGTTCAGCGTGTCCGGCGAGGGCGAGGGCGATGCCACCTAC<br>GGCAAGCTGACCCTGAAGTTCATCTGCACCACCGGCAAGCT<br>GCCCGTGCCCTGGCCCACCCTCGTGACCACCCTGACCTGG<br>GCGTGCAGTGCTTCAGCCGCTACCCCGACCACATGAAGCAG |

TABLE-continued

Amino acid and nucleotide sequences

| Name | Sequence |
|---|---|
| | CACGACTTCTTCAAGTCCGCCATGCCCGAAGGCTACGTCCA |
| | GGAGCGTACCATCTTCTTCAAGGACGACGGCAACTACAAGA |
| | CCCGCGCCGAGGTGAAGTTCGAGGGCGACACCCTGGTGAAC |
| | CGCATCGAGCTGAAGGGCATCGACTTCAAGGAGGACGGCAA |
| | CATCCTGGGGCACAAGCTGGAGTACAACTACATCAGCCACA |
| | ACGTCTATATCACCGCCGACAAGCAGAAGAACGGCATCAAG |
| | GCCCACTTCAAGATCCGCCACAACATCGAGGACGGCAGCGT |
| | GCAGCTCGCCGACCACTACCAGCAGAACACCCCCATCGGCG |
| | ACGGCCCCGTGCTGCTGCCCGACAACCACTACCTGAGCACC |
| | CAGTCCGCCCTGAGCAAAGACCCCAACGAGAAGCGCGATCA |
| | CATGGTCCTGCTGGAGTTCGTGACCGCCGCCGAGCTCATGG |
| | CGGATCAGTTGACCGACGATCAGATCTCTGAATTTAAGGAA |
| | GCCTTCAGCTTATTCGACGGTGATGGTTGCATTACCACCAA |
| | GGAACTGGGTACTGTGATGCGTTCCCTGGGCCAAAACCCGA |
| | CCGAAGCAGAGCTGCAAGACATGATCAACGAAGTGGATGGT |
| | AACGGTACCATTGATTTCCCGGAATTCTTGAACCTGATGGC |
| | CCGTAAGATGAAAGACACCGACAGCGAGGAAGAGCTGAAAG |
| | AAGCCTTCCGCGTTTTCGACCAGAACGGTTTCATCAGCGCA |
| | GCGGAACTGCGCCATGTGATGACCAACCTGGGCGAAAAACT |
| | GACGGATGAAGAAGTTGATGAGATGATCAAAGAAGCGGATG |
| | TGGATGGTGATGGTCAGATTAACTACGAAGAGTTTGTTAAG |
| | GTGATGATGGCGAAAGGCGGTGGCGGTAGCAAACGTCGCTG |
| | GAAAAAAAACTTTATTGCGGTGAGCGCGGCCAACCGCTTTA |
| | AAAAAATTAGCTCGAGCGGCGCGCTGGTCGACATGGTGAGC |
| | AAGGGCGAGGAGCTGTTCACCGGGGTGGTGCCCATCCTGGT |
| | CGAGCTGGACGGCGACGTAAACGGCCACAAGTTCAGCGTGT |
| | CCGGCGAGGGCGAGGGCGATGCCACCTACGGCAAGCTGACC |
| | CTGAAGTTCATCTGCACCACCGGCAAGCTGCCCGTGCCCTG |
| | GCCCACCCTCGTGACCACCTTCGGCTACGGCGTGCAGTGCT |
| | TCGCCCGCTACCCCGACCACATGAAGCAGCACGACTTCTTC |
| | AAGTCCGCCATGCCCGAAGGCTACGTCAGGAGCGCACCAT |
| | CTTCTTCAAGGACGACGGCAACTACAAGACCCGCGCCGAGG |
| | TGAAGTTCGAGGGCGACACCCTGGTGAACCGCATCGAGCTG |
| | AAGGGCATCGACTTCAAGGAGGACGGCAACATCCTGGGGCA |
| | CAAGCTGGAGTACAACTACAACAGCCACAACGTCTATATCA |
| | TGGCCGACAAGCAGAAGAACGGCATCAAGGTGAACTTCAAG |
| | ATCCGCCACAACATCGAGGACGGCAGCGTGCAGCTCGCCGA |
| | CCACTACCAGCAGAACACCCCCATCGGCGACGGCCCCGTGC |
| | TGCTGCCCGACAACCACTACCTGAGCTACCAGTCCGCCCTG |
| | AGCAAAGACCCCAACGAGAAGCGCGATCACATGGTCCTGCT |
| | GGAGTTCGTGACCGCCGCCGGGATCACTCTCGGCATGGACG |
| | AGCTGTACAAGTAA |
| SEQ ID NO: 65 Cameleon Biosensor N-ter | SMVSKGEELFTGVVPILVELDGDVNGHRFSVSGEGEGDATY GKLTLKFICTTGKLPVPWPTLVTTLTWGVQCFSRYPDHMKQ HDFFKSAMPEGYVQERTIFFKDDGNYKTRAEVKFEGDTLVN RIELKGIDFKEDGNILGHKLEYNYISHNVYITADKQKNGIK AHFKIRHNIEDGSVQLADHYQQNTPIGDGPVLLPDNHYLST QSALSKDPNEKRDHMVLLEFVTAAelpMADQLTDDQISEFK EAFSLFDKDGDGCITTKELGTVMRSLGQNPTEAELQDMINE VDADGNGTIDEPEFLNLMARKpvdMVSKGEELFTGVVPILV ELDGDVNGHKFSVSGEGEGDATYGKLTLKFICTTGKLPVPW PTLVTTEGYGVQCFARYPDHMKQHDFFKSAMPEGYVQERTI FFKDDGNYKTRAEVKFEGDTLVNRIELKGIDEKEDGNILGH KLEYNYNSHNVYIMADKQKNGIKVNFKIRHNIEDGSVQLAD HYQQNTPIGDGPVLLPDNHYLSYQSALSKDPNEKRDHMVLL EFVTAAGITLGMDELYK |
| SEQ ID NO: 66 Cameleon Biosensor N-ter | TCCATGGTGAGCAAGGGCGAGGAGCTGTTCACCGGGGTGGT GCCCATCCTGGTCGAGCTGGACGGCGACGTAAACGGCCACA GGTTCAGCGTGTCCGGCGAGGGCGAGGGCGATGCCACCTAC GGCAAGCTGACCCTGAAGTTCATCTGCACCACCGGCAAGCT GCCCGTGCCCTGGCCCACCCTCGTGACCACCCTGACCTGGG GCGTGCAGTGCTTCAGCCGCTACCCCGACCACATGAAGCAG CACGACTTCTTCAAGTCCGCCATGCCCGAAGGCTACGTCCA GGAGCGTACCATCTTCTTCAAGGACGACGGCAACTACAAGA CCCGCGCCGAGGTGAAGTTCGAGGGCGACACCCTGGTGAAC CGCATCGAGCTGAAGGGCATCGACTTCAAGGAGGACGGCAA CATCCTGGGGCACAAGCTGGAGTACAACTACATCAGCCACA ACGTCTATATCACCGCCGACAAGCAGAAGAACGGCATCAAG GCCCACTTCAAGATCCGCCACAACATCGAGGACGGCAGCGT GCAGCTCGCCGACCACTACCAGCAGAACACCCCCATCGGCG ACGGCCCCGTGCTGCTGCCCGACAACCACTACCTGAGCACC CAGTCCGCCCTGAGCAAAGACCCCAACGAGAAGCGCGATCA CATGGTCCTGCTGGAGTTCGTGACCGCCGCCGAGCTCccgA TGGCGGATCAGTTGACCGACGATCAGATCTCTGAATTTAAG |

TABLE-continued

Amino acid and nucleotide sequences

| Name | Sequence |
|---|---|
| | GAAGCCTTCAGCTTATTCGACAAGGATGGTGATGGTTGCAT<br>TACCACCAAGGAACTGGGTACTGTGATGCGTTCCCTGGGCC<br>AAAACCCGACCGAAGCAGAGCTGCAAGACATGATCAACGAA<br>GTGGATGCGGATGGTAACGGTACCATTGATTTCCCGGAATT<br>CTTGAACCTGATGGCCCGTAAGccgGTCGACATGGTGAGCA<br>AGGGCGAGGAGCTGTTCACCGGGGTGGTGCCCATCCTGGTC<br>GAGCTGGACGGCGACGTAAACGGCCACAAGTTCAGCGTGTC<br>CGGCGAGGGCGAGGGCGATGCCACCTACGGCAAGCTGACCC<br>TGAAGTTCATCTGCACCACCGGCAAGCTGCCCGTGCCCTGG<br>CCCACCCTCGTGACCACCTTCGGCTACGGCGTGCAGTGCTT<br>CGCCCGCTACCCCGACCACATGAAGCAGCACGACTTCTTCA<br>AGTCCGCCATGCCCGAAGGCTACGTCCAGGAGCGCACCATC<br>TTCTTCAAGGACGACGGCAACTACAAGACCCGCGCCGAGGT<br>GAAGTTCGAGGGCGACACCCTGGTGAACCGCATCGAGCTGA<br>AGGGCATCGACTTCAAGGAGGACGGCAACATCCTGGGGCAC<br>AAGCTGGAGTACAACTACAACAGCCACAACGTCTATATCAT<br>GGCCGACAAGCAGAAGAACGGCATCAAGGTGAACTTCAAGA<br>TCCGCCACAACATCGAGGACGGCAGCGTGCAGCTCGCCGAC<br>CACTACCAGCAGAACACCCCCATCGGCGACGGCCCCGTGCT<br>GCTGCCCGACAACCACTACCTGAGCTACCAGTCCGCCCTGA<br>GCAAAGACCCCAACGAGAAGCGCGATCACATGGTCCTGCTG<br>GAGTTCGTGACCGCCGCCGGGATCACTCTCGGCATGGACGA<br>GCTGTACAAGTAA |
| SEQ ID NO: 67 Cameleon Biosensor Δ1 Δ2 | SMVSKGEELFTGVVPILVELDGDVNGHRFSVSGEGEGDATY<br>GKLTLKFICTTGKLPVPWPTLVTTLTWGVQCFSRYPDHMKQ<br>HDFFKSAMPEGYVQERTIFFKDDGNYKTRAEVKFEGDTLVN<br>RIELKGIDFKEDGNILGHKLEYNYISHNVYITADKQKNGIK<br>AHFKIRHNIEDGSVQLADHYQQNTPIGDGPVLLPDNHYLST<br>QSALSKDPNEKRDHMVLLEFVTAAELMADQLTDDQISEFKE<br>AFSLEDGDGCITTKELGTVMRSLGQNPTEAELQDMINEVDG<br>NGTIDFPEFLNLMARKMKDTDSEEELKEAFRVFDKDQNGFI<br>SAAELRHVMTNLGEKLTDEEVDEMIKEADVDGDGQINYEEF<br>VKVMMAKGGGGSKRRWKKNFIAVSAANRFKKISSSGALVDM<br>VSKGEELFTGVVPILVELDGDVNGHKFSVSGEGEGDATYGK<br>LTLKFICTTGKLPVPWPTLVTTFGYGVQCFARYPDHMKQHD<br>FFKSAMPEGYVQERTIFFKDDGNYKTRAEVKFEGDTLVNRI<br>ELKGIDFKEDGNILGHKLEYNYNSHNVYIMADKQKNGIKVN<br>FKIRHNIEDGSVQLADHYQQNTPIGDGPVLLPDNHYLSYQS<br>ALSKDPNEKRDHMVLLEFVTAAGITLGMDELYK |
| SEQ ID NO: 68 Cameleon Biosensor Δ1 Δ2 | TCCATGGTGAGCAAGGGCGAGGAGCTGTTCACCGGGGTGGT<br>GCCCATCCTGGTCGAGCTGGACGGCGACGTAAACGGCCACA<br>GGTTCAGCGTGTCCGGCGAGGGCGAGGGCGATGCCACCTAC<br>GGCAAGCTGACCCTGAAGTTCATCTGCACCACCGGCAAGCT<br>GCCCGTGCCCTGGCCCACCCTCGTGACCACCCTGACCTGGG<br>GCGTGCAGTGCTTCAGCCGCTACCCCGACCACATGAAGCAG<br>CACGACTTCTTCAAGTCCGCCATGCCCGAAGGCTACGTCCA<br>GGAGCGTACCATCTTCTTCAAGGACGACGGCAACTACAAGA<br>CCCGCGCCGAGGTGAAGTTCGAGGGCGACACCCTGGTGAAC<br>CGCATCGAGCTGAAGGGCATCGACTTCAAGGAGGACGGCAA<br>CATCCTGGGGCACAAGCTGGAGTACAACTACATCAGCCACA<br>ACGTCTATATCACCGCCGACAAGCAGAAGAACGGCATCAAG<br>GCCCACTTCAAGATCCGCCACAACATCGAGGACGGCAGCGT<br>GCAGCTCGCCGACCACTACCAGCAGAACACCCCCATCGGCG<br>ACGGCCCCGTGCTGCTGCCCGACAACCACTACCTGAGCACC<br>CAGTCCGCCCTGAGCAAAGACCCCAACGAGAAGCGCGATCA<br>CATGGTCCTGCTGGAGTTCGTGACCGCCGCCGAGCTCATGG<br>CGGATCAGTTGACCGACGATCAGATCTCTGAATTtaAGGAA<br>GCCTTCAGCTTATTCGACGGTGATGGTTGCATTACCACCAA<br>GGAACTGGGTACTGTGATGCGTTCCCTGGGCCAAAACCCGA<br>CCGAAGCAGAGCTGCAAGACATGATCAACGAAGTGGATGGT<br>AACGGTACCATTGATTTCCCGGAATTCTTGAACCTGATGGC<br>CCGTAAGATGAAAGACACCGACAGCGAGGAAGAGCTGAAAG<br>AAGCCTTCCGCGTTTTCGACAAAGACCAGAACGGTTTCATC<br>AGCGCAGCGGAACTGCGCCATGTGATGACCAACCTGGGCGA<br>AAAACTGACGGATGAAGAAGTTGATGAGATGATCAAAGAAG<br>CGGATGTGGATGGTGATGGTCAGATTAACTACGAAGAGTTT<br>GTTAAGGTGATGATGGCGAAAGGCGGTGGCGGTAGCAAACG<br>TCGCTGGAAAAAAaCTTTATTGCGGTGAGCGCGGCCAACC<br>GCTTTAAAAAAATTAGCTCGAGCGGCGCTGGTCGACAtg<br>gtGAGCAAGGGCgaggagcTGtTCACCGGGgtggtgCCCAT<br>CctggtCGAgctgGaCGGCGAcgtAAACGGCCACAagtTCA<br>GcgtgTCCGGCgAGGGCgagGGCGatgCCAcCTACGGCAAG<br>CTGaCCcTGAAGTTCATCTGCACCACCGGCAAGCTGCCCgt<br>GCCctgGCCCACCCTcgtgaCCACCTTCGGCtACGGCgtgC |

TABLE-continued

Amino acid and nucleotide sequences

| Name | Sequence |
| --- | --- |
| | AgtgCtTCGCCCGCTACCCCGACCACATGAAGCAGCACGAC<br>TTCTTCAAGTCCGCCAtgCCCGAAGGCTACGTCCAGGAGCG<br>CACCATCTTCTTCAAGGACGACGGCAACTACAAGACCCGCG<br>CCGAGGTGAAGTTCGAGGGCGACACCCTGgtGAACCGCATC<br>GAGCTGAAGGGCATCGACTTCAAGGAGGACGGCAACATCCT<br>GGGGCACAAGCTGGAGTACAACTACAACAGCCACAACGTCT<br>ATATCATGGCCGACAAGCAGAAGAACGGCATCAAGGTGAAC<br>TTCAAGATCCGCCACAACATCGAGGACGGCAGCGTGCAGCT<br>CGCCGACCACTACCAGCAGAACACCCCCATCGGCGACGGCC<br>CCGTGCTGCTGCCCGACAACCACTACCTGAGCTACCAGTCC<br>GCCCTGAGCAAAGACCCCAACGAGAAGCGCGATCACATGGT<br>CCTGCTGGAGTTCGTGACCGCCGCCGGGATCacTCTCGGCA<br>TGGACGaGCTGTACAAGTAA |
| SEQ ID NO: 69 EF-hand1 loop +<br>C7Y + T10A + K11A | DKDGDGYITAAE |
| SEQ ID NO: 70 EF-hand1 loop<br>ΔD1T10 | KDGDGCITKE |
| SEQ ID NO: 71 EF-hand1 loop<br>ΔD1K11 | KDGDGCITTE |
| SEQ ID NO: 72 EF-hand1 loop<br>ΔD3T10 | DKGDGCITKE |
| SEQ ID NO: 73 EF-hand1 loop<br>ΔD3K11 | DKGDGCITTE |
| SEQ ID NO: 74 EF-hand1 loop<br>ΔD1T10K11 | KDGDGCITE |
| SEQ ID NO: 75 EF-hand1 loop<br>ΔD3T10K11 | DKGDGCITE |
| SEQ ID NO: 76 EF-hand2 loop<br>ΔD1F10 | ADGNGTIDPE |
| SEQ ID NO: 77 EF-hand2 loop<br>ΔD1P11 | ADGNGTIDFE |
| SEQ ID NO: 78 EF-hand2 loop<br>ΔD3F10 | DAGNGTIDPE |
| SEQ ID NO: 79 EF-hand2 loop<br>ΔD3P11 | DAGNGTIDFE |
| SEQ ID NO: 80 EF-hand2 loop<br>ΔD1F10P11 | ADGNGTIDE |
| SEQ ID NO: 81 EF-hand2 loop<br>ΔD3F10P11 | DAGNGTIDE |
| SEQ ID NO: 82 EF-hand3 loop<br>ΔD1A10 | KDQNGFISAE |
| SEQ ID NO: 83 EF-hand3 loop<br>ΔD1A11 | KDQNGFISAE |
| SEQ ID NO: 84 EF-hand3 loop<br>ΔD3A10 | DKQNGFISAE |
| SEQ ID NO: 85 EF-hand3 loop<br>ΔD3A11 | DKQNGFISAE |
| SEQ ID NO: 86 EF-hand3 loop<br>ΔD1A10A11 | KDQNGFISE |
| SEQ ID NO: 87 EF-hand3 loop<br>ΔD3A10A11 | DKQNGFISE |
| SEQ ID NO: 88 EF-hand4 loop<br>ΔD1Y10 | VDGDGQINEE |
| SEQ ID NO: 89 EF-hand4 loop<br>ΔD1E11 | VDGDGQINYE |

TABLE-continued

Amino acid and nucleotide sequences

| Name | Sequence |
|---|---|
| SEQ ID NO: 90 EF-hand4 loop ΔD3Y10 | DVGDGQINEE |
| SEQ ID NO: 91 EF-hand4 loop ΔD3E11 | DVGDGQINYE |
| SEQ ID NO: 92 EF-hand4 loop ΔD1Y10E11 | VDGDGQINE |
| SEQ ID NO: 93 EF-hand4 loop ΔD3Y10E11 | DVGDGQINE |

The invention claimed is:

1. A polypeptide comprising at least one helix-loop-helix calcium-binding (EF-hand) motif with deletion of two amino acid residues in the 12-amino-acid calcium-binding loop sequence selected from the group consisting of deletion in positions 1 and 2, and deletion in positions 2 and 3, wherein said polypeptide binds uranyl.

2. The polypeptide of claim 1, wherein said EF-hand motif(s) are derived from signaling EF-hand protein(s) of the calmodulin superfamily selected from the group consisting of calmodulin and troponin C.

3. The polypeptide of claim 1, which comprises two or four EF-hand motifs, wherein at least one EF-hand motif comprises said deletion in the calcium-binding loop sequence, and the other EF-hand motif(s) comprise said deletion or not.

4. The polypeptide of claim 2, which is a calmodulin domain 1 variant comprising two EF-hand motifs, respectively from the EF-hand1 and the EF-hand2 of calmodulin protein(s).

5. The polypeptide of claim 3, which comprises an amino acid sequence selected from the group consisting of SEQ ID NO: 17, 18, 20 and 60.

6. A fusion protein comprising a polypeptide according to claim 1 fused to another protein moiety.

7. The fusion protein of claim 6, which is a cameleon protein comprising tandem fusions of a fluorescence-donor protein, a polypeptide which comprises two or four EF-hand motifs, wherein at least one EF-hand motif comprises said deletion in the calcium-binding loop sequence and the other EF-hand motif(s) comprise said deletion or not, and a fluorescence-acceptor protein.

8. The fusion protein of claim 7, which comprises a sequence selected from the group consisting of SEQ ID NO: 35, 38, 61, 63 and 67.

9. The polypeptide of claim 1 or a fusion protein comprising a polypeptide according to claim 1 fused to another protein moiety, which is immobilized onto a solid support.

10. A polynucleotide encoding the polypeptide of claim 1.

11. A host cell comprising with the polynucleotide of claim 10, wherein the host cell is not an organism.

12. A non-human transgenic organism comprising the polynucleotide of claim 10.

13. A method of detecting uranium contamination in a sample comprising contacting the sample with a uranyl chelating agent comprising:
  i. the polypeptide of claim 1,
  ii. a fusion protein comprising a polypeptide according to claim 1 fused to another protein moiety,
  iii. a host cell comprising a polynucleotide encoding the polypeptide of claim 1 or a fusion protein comprising a polypeptide according to claim 1 fused to another protein moiety, or
  iv. A non-human transgenic organism comprising a polynucleotide encoding the polypeptide of claim 1 or a fusion protein comprising a polypeptide according to claim 1 fused to another protein moiety, and detecting the presence of uranyl chelation in the sample.

14. A method of decontaminating or bio-remediating a sample containing uranium comprising contacting the sample with a uranyl chelating agent comprising:
  i. the polypeptide of claim 1,
  ii. a fusion protein comprising a polypeptide according to claim 1 fused to another protein moiety,
  iii. a host cell comprising a polynucleotide encoding the polypeptide of claim 1 or a fusion protein comprising a polypeptide according to claim 1 fused to another protein moiety, or
  iv. A non-human transgenic organism comprising a polynucleotide encoding the polypeptide of claim 1 or a fusion protein comprising a polypeptide according to claim 1 fused to another protein moiety.

15. The polypeptide of claim 3, which consists of an amino acid sequence selected from the group consisting of SEQ ID NO: 17, 18, 20 and 60.

16. The fusion protein of claim 7, which consists of a sequence selected from the group consisting of SEQ ID NO: 35, 38, 61, 63 and 67.

17. A polynucleotide encoding a fusion protein comprising the polypeptide according to claim 1 fused to another protein moiety.

* * * * *